(12) United States Patent
Newberry

(10) Patent No.: US 9,968,289 B2
(45) Date of Patent: ***May 15, 2018

(54) SYSTEM AND METHOD FOR DETECTING A SEPSIS CONDITION

(71) Applicant: Sanmina Corporation, San Jose, CA (US)

(72) Inventor: Robert Steven Newberry, New Hope, AL (US)

(73) Assignee: SANMINA CORPORATION, San Jose, CA (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/680,991

(22) Filed: Aug. 18, 2017

(65) Prior Publication Data

US 2018/0020964 A1    Jan. 25, 2018

Related U.S. Application Data

(63) Continuation-in-part of application No. 15/622,941, filed on Jun. 14, 2017, now Pat. No. 9,788,767, and a continuation-in-part of application No. 15/490,813, filed on Apr. 18, 2017, and a continuation-in-part of application No. 15/489,391, filed on Apr. 17, 2017, and a continuation-in-part of application No. 15/485,816, filed on Apr. 12, 2017, and a continuation-in-part of application No. 15/400,916, filed on Jan. 6, 2017, and a continuation-in-part of
(Continued)

(51) Int. Cl.
*A61B 5/1455* (2006.01)
*A61B 5/00* (2006.01)
*A61B 5/0205* (2006.01)
*A61B 5/01* (2006.01)
*A61B 5/145* (2006.01)
*A61B 5/08* (2006.01)
*A61B 5/024* (2006.01)

(52) U.S. Cl.
CPC ............ *A61B 5/412* (2013.01); *A61B 5/0075* (2013.01); *A61B 5/01* (2013.01); *A61B 5/0205* (2013.01); *A61B 5/14532* (2013.01); *A61B 5/14551* (2013.01); *A61B 5/7275* (2013.01); *A61B 5/746* (2013.01); *A61B 5/02416* (2013.01); *A61B 5/0816* (2013.01); *A61B 2560/0214* (2013.01); *A61B 2560/0228* (2013.01)

(58) Field of Classification Search
None
See application file for complete search history.

(56) References Cited

U.S. PATENT DOCUMENTS 7,941,199 B2   5/2011  Kiani
8,224,411 B2   7/2012  Al-Ali et al.
(Continued)

*Primary Examiner* — Eric Winakur
*Assistant Examiner* — Marjan Fardanesh
(74) *Attorney, Agent, or Firm* — Loza & Loza, LLP; Julio M. Loza; Jessica W. Smith

(57) ABSTRACT

A biosensor includes an optical sensor circuit that emits light directed at skin tissue of a patient at a plurality of wavelengths. A first and second spectral response of light reflected from the tissue is obtained around a first wavelength in a UV range and a second wavelength in an IR range. A measurement of nitric oxide (NO) is then determined from the spectral responses. A risk of septic condition is obtained using the measurement of NO.

24 Claims, 44 Drawing Sheets

Related U.S. Application Data application No. 15/404,117, filed on Jan. 11, 2017, and a continuation-in-part of application No. 15/462,700, filed on Mar. 17, 2017, application No. 15/680,991, which is a continuation-in-part of application No. 14/866,500, filed on Sep. 25, 2015.

(60) Provisional application No. 62/463,104, filed on Feb. 24, 2017, provisional application No. 62/457,138, filed on Feb. 9, 2017.

(56) References Cited

U.S. PATENT DOCUMENTS

| | | |
|---|---|---|
| 8,385,996 B2 | 2/2013 | Smith et al. |
| 2011/0275978 A1* | 11/2011 | Hyde .................... A61K 33/00 604/20 |
| 2012/0010683 A1* | 1/2012 | Keswarpu ................ A61N 5/06 607/88 |

* cited by examiner

700

702
Determine spectral response at a first wavelength in UV range

704
Determine spectral response at a second wavelength

706
Determine concentration level of NO using the spectral response at the first and second wavelength

3302 Obtain baseline NO measurement in blood vessels of a healthy general population

3304 Obtain NO measurement in blood vessels of a general population with a diagnosis of sepsis

3306 Obtain predetermined thresholds based on NO measurements

3308 Configure biosensor with predetermined thresholds

4202 Obtain non-invasive, continuous NO measurement in blood vessels

4204 Display NO measurement

4206 Compare to predetermined thresholds

4208 Display relative pain level using NO measurement

FIG. 42

SYSTEM AND METHOD FOR DETECTING A SEPSIS CONDITION

CROSS REFERENCE TO RELATED APPLICATIONS

The present application claims priority under 35 U.S.C. § 119(e) to U.S. Provisional Application No. 62/463,104 entitled, "SYSTEM AND METHOD FOR MONITORING NITRIC OXIDE LEVELS USING A NON-INVASIVE, MULTI-BAND BIOSENSOR," filed Feb. 24, 2017, and hereby expressly incorporated by reference herein.

The present application claims priority under 35 U.S.C. § 120 as a continuation in part to U.S. patent application Ser. No. 15/622,941 entitled, "SYSTEM AND METHOD FOR MONITORING NITRIC OXIDE LEVELS USING A NON-INVASIVE, MULTI-BAND BIOSENSOR," filed Jun. 14, 2017, and hereby expressly incorporated by reference herein.

The present application claims priority under 35 U.S.C. § 120 as a continuation in part application to U.S. patent application Ser. No. 15/490,813 entitled, "SYSTEM AND METHOD FOR HEALTH MONITORING USING A NON-INVASIVE, MULTI-BAND BIOSENSOR 500," filed Apr. 18, 2017 and hereby expressly incorporated by reference herein.

The present application claims priority under 35 U.S.C. § 120 as a continuation in part application to U.S. patent application Ser. No. 15/489,391 entitled, "SYSTEM AND METHOD FOR A BIOSENSOR 500 MONITORING AND TRACKING BAND," filed Apr. 17, 2017 and hereby expressly incorporated by reference herein.

The present application claims priority under 35 U.S.C. § 120 as a continuation in part application to U.S. patent application Ser. No. 15/485,816 entitled, "SYSTEM AND METHOD FOR A DRUG DELIVERY AND BIOSENSOR 500 PATCH," filed Apr. 12, 2017 and hereby expressly incorporated by reference herein.

The present application claims priority under 35 U.S.C. § 120 as a continuation in part application to U.S. patent application Ser. No. 15/400,916 entitled, "SYSTEM AND METHOD FOR HEALTH MONITORING INCLUDING A REMOTE DEVICE," filed Jan. 6, 2017 and hereby expressly incorporated by reference herein.

The present application claims priority under 35 U.S.C. § 120 as a continuation in part application to U.S. patent application Ser. No. 15/404,117 entitled, "SYSTEM AND METHOD FOR HEALTH MONITORING INCLUDING A USER DEVICE AND BIOSENSOR," filed Jan. 11, 2017 and hereby expressly incorporated by reference herein.

The present application claims priority under 35 U.S.C. § 120 as a continuation in part application to U.S. patent application Ser. No. 15/462,700 entitled, "SYSTEM AND METHOD FOR ATOMIZING AND MONITORING A DRUG CARTRIDGE DURING INHALATION TREATMENTS," filed Mar. 17, 2017 and hereby expressly incorporated by reference herein, which claims priority under 35 U.S.C. §119(e) to U.S. Provisional Application No. 62/457,138 entitled, "SYSTEM AND METHOD FOR ATOMIZING AND MONITORING A DRUG CARTRIDGE DURING INHALATION TREATMENTS," filed Feb. 9, 2017, and hereby expressly incorporated by reference herein.

The present application claims priority under 35 U.S.C. § 120 as a continuation in part to U.S. patent application Ser. No. 14/866,500 entitled, "SYSTEM AND METHOD FOR GLUCOSE MONITORING," filed Sep. 25, 2015, and hereby expressly incorporated by reference herein.

FIELD

This application relates to a system and methods of non-invasive, autonomous health monitoring, and in particular a system and method for health monitoring to detect a sepsis condition in a patient.

BACKGROUND

Sepsis is a serious medical condition caused by the body's response to an infection. Bacterial infections are the most common cause of sepsis, but sepsis can also be caused by fungal, parasitic, or viral infections. Toxins produced by an untreated or inadequately treated infection circulate in the bloodstream causing damage, for example, to the brain, heart, lungs, kidneys and liver. Severe sepsis can result in septic shock, a medical emergency in which the organs and tissues of the body are not receiving an adequate flow of blood. Sepsis is more common and more dangerous in persons who are very young or very old, have a compromised immune system, are already very sick, often in a hospital's intensive care unit, have wounds or injuries, such as burns, have invasive devices, such as intravenous catheters or breathing tubes. Such at risk patients are not continuously monitored or tested for sepsis and often not until symptoms appear. Since sepsis is very dangerous and may escalate to life threatening conditions quickly, it would be advantageous to have a device and method for noninvasively and continuously monitoring at risk patients.

It has been shown that sepsis results in large amounts of nitric oxide (NO) released into the blood. The overproduction of NO during sepsis induces excessive vascular relaxation and a profound hypotension that is also a characteristic feature of sepsis. Various invasive methods have been developed for measurement of nitric oxide (NO) levels using one or more types of techniques to remove cells from various types of bodily fluids. The methods usually require drawing blood from a blood vessel using a needle and syringe. The blood sample is then transported to a lab for analysis to determine NO levels using physical or chemical measurements. For example, in one current method, a blood sample is inserted into a semi-permeable vessel including an NO reacting substance that traps NO diffusing thereinto. A physical or chemical detection method is then used to measure the levels of NO in the blood sample.

These known in vitro measurements of NO levels have disadvantages. The process of obtaining blood samples is time consuming, inconvenient and painful to a patient. It may also disrupt sleep of the patient. The measurements of the NO levels are not continuous and may only be updated by taking another blood sample.

One current non-invasive method is known for measuring oxygen saturation in blood vessels using pulse oximeters. Pulse oximeters detect oxygen saturation of hemoglobin by using, e.g., spectrophotometry to determine spectral absorbencies and determining concentration levels of oxygen based on Beer-Lambert law principles. In addition, pulse oximetry may use photoplethysmography (PPG) methods for the assessment of oxygen saturation in pulsatile arterial blood flow. The subject's skin at a 'measurement location' is illuminated with two distinct wavelengths of light and the relative absorbance at each of the wavelengths is determined. For example, a wavelength in the visible red spectrum (for example, at 660 nm) has an extinction coefficient of hemoglobin that exceeds the extinction coefficient of oxihemoglobin. At a wavelength in the near infrared spectrum (for example, at 940 nm), the extinction coefficient of oxihemoglobin exceeds the extinction coefficient of hemoglobin. The pulse oximeter filters the absorbance of the pulsatile fraction of the blood, i.e. that due to arterial blood (AC components), from the constant absorbance by nonpulsatile venous or capillary blood and other tissue pigments (DC components), to eliminate the effect of tissue absorbance to measure the oxygen saturation of arterial blood. A practical application of this technique is pulse oximetry, which utilizes a noninvasive sensor to measure oxygen saturation ($SpO_2$) and pulse rate and can output representative plethysmographic waveforms. Such PPG techniques are heretofore been limited to determining oxygen saturation using wavelengths in the infrared spectrum.

As such, there is a need for a patient monitoring system and method that includes a continuous and non-invasive biosensor configured to monitor concentration levels of NO in blood flow in vivo for detection of a sepsis.

SUMMARY

According to a first aspect, a biosensor for detecting a sepsis condition includes a photoplethysmography (PPG) circuit configured to obtain at least a first spectral response of light reflected from skin tissue of a patient, wherein the light includes a first wavelength in an ultraviolet (UV) range. The biosensor also includes a processing circuit configured to obtain a measurement of nitric oxide (NO) using the first spectral response. The processing circuit is further configured to compare the measurement of NO to one or more predetermined thresholds and generate an indication of a risk of sepsis based on the comparison.

According to a second aspect, a biosensor is configured to monitor one or more health conditions. The biosensor includes a sensor circuit configured to generate at least a first spectral response for light with a first wavelength in an ultraviolet (UV) range reflected from skin tissue of a patient and generate at least a second spectral response for light detected around a second wavelength reflected from the skin tissue of the patient. The biosensor further includes a processing circuit configured to determine a first mode of operation for monitoring a risk of sepsis and obtain a measurement of nitric oxide (NO) in pulsating arterial blood flow using the first spectral response and the second spectral response. The processing circuit is further configured to compare the measurement of NO to one or more predetermined thresholds based on the first mode of operation and generate an indication of the risk of sepsis based on the comparison. The processing circuit is further configured to determine a second mode of operation for determining a diabetic risk indicator, to compare the measurement of NO to one or more predetermined thresholds based on the second mode of operation and to obtain a base insulin resistance factor that indicates a diabetic risk indicator. The processing circuit is further configured to determine a third mode of operation for monitoring a blood glucose concentration level detected from an insulin response and obtain the blood glucose concentration level detected from an insulin response using the measurement of NO and a calibration table.

In a third aspect, a method for detecting a sepsis condition includes obtaining a first spectral response of light reflected from skin tissue of a patient, wherein the light includes a first wavelength in an ultraviolet (UV) range and obtaining a second spectral response of light reflected from skin tissue of a patient, wherein the light includes a second wavelength of 660 nm or greater. The method further includes obtaining a measurement of nitric oxide (NO) in pulsating arterial blood flow using the first spectral response and the second spectral response, comparing the measurement of NO to one or more predetermined thresholds, and generating an indication of a risk of sepsis based on the comparison.

BRIEF DESCRIPTION OF THE DRAWINGS

FIG. 7 illustrates a logical flow diagram of an exemplary embodiment of a method for measuring nitric oxide (NO) in blood vessels.

FIG. 33 illustrates a logical flow diagram of an embodiment of a method for determining predetermined thresholds for health alert indicators for sepsis.

FIG. 42 illustrates a logical flow diagram of an embodiment of a method for determining a pain level using the biosensor.

DETAILED DESCRIPTION

Figure 1B:
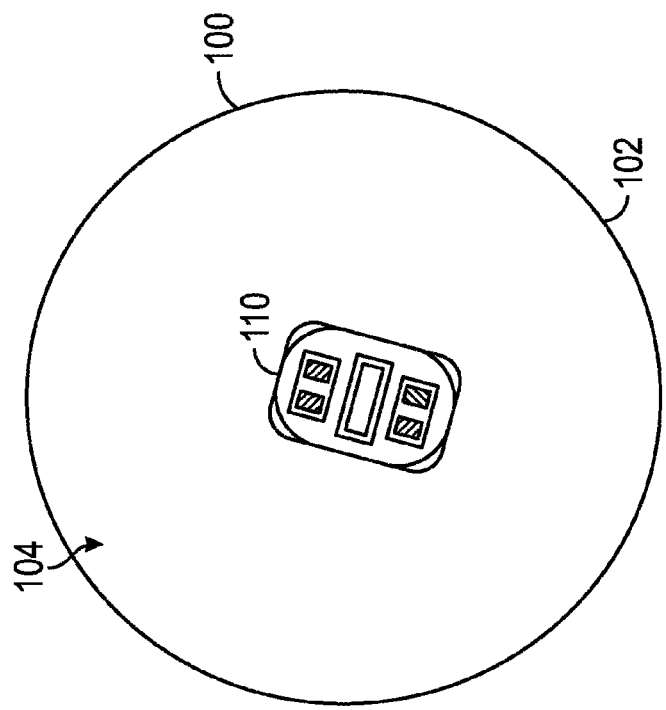
FIG. 1B illustrates another perspective view of an embodiment of a biosensor.

The word "exemplary" or "embodiment" is used herein to mean "serving as an example, instance, or illustration." Any implementation or aspect described herein as "exemplary" or as an "embodiment" is not necessarily to be construed as preferred or advantageous over other aspects of the disclosure. Likewise, the term "aspects" does not require that all aspects of the disclosure include the discussed feature, advantage, or mode of operation.

Embodiments will now be described in detail with reference to the accompanying drawings. In the following description, numerous specific details are set forth in order to provide a thorough understanding of the aspects described herein. It will be apparent, however, to one skilled in the art, that these and other aspects may be practiced without some or all of these specific details. In addition, well known steps in a method of a process may be omitted from flow diagrams presented herein in order not to obscure the aspects of the disclosure. Similarly, well known components in a device may be omitted from figures and descriptions thereof presented herein in order not to obscure the aspects of the disclosure.

Nitric oxide (NO) is produced by a group of enzymes called nitric oxide synthases. These enzymes convert arginine into citrulline, producing NO in the process. Oxygen and NADPH are necessary co-factors. There are three isoforms of nitric oxide synthase (NOS) named according to their activity or the tissue type in which they were first described. The isoforms of NOS are neural NOS (or nNOS, type 1), inducible NOS (or iNOS, type 2), and endothelial NOS (or eNOS, type 3). These enzymes are also sometimes referred to by number, so that nNOS is known as NOS1, iNOS is known as NOS2, and eNOS is NOS3. Despite the names of the enzymes, all three isoforms can be found in variety of tissues and cell types. Two of the enzymes (nNOS and eNOS) are constitutively expressed in mammalian cells and synthesize NO in response to increases in intracellular calcium levels. In some cases, however, they are able to increase NO production independently of calcium levels in response to stimuli such as shear stress.

In most cases NO production increases in proportion to the amount of calories or food consumed. Normally this is derived from the eNOS type NO production, and the body uses the NO first as a vasodilator and also as a protective oxidation layer to prevent undesired oxides from passing thru the cells in the blood vessels walls. The amount of NO released in this case is measured in small pulses and builds up as part of the normal digestion process. In the case of type 1 or type 2 diabetics, the normal levels of eNOS are abnormally low as found in recent clinical studies.

However iNOS activity is independent of the level of calcium in the cell, and all forms of the NOS isoforms are dependent on the binding of calmodulin. Increases in cellular calcium lead to increase in levels of calmodulin and the increased binding of calmodulin to eNOS and nNOS leads to a transient increase in NO production by these enzymes. By contrast iNOS is able to bind tightly to calmodulin even at extremely low concentrations of calcium. Therefore iNOS activity does not respond to changes in calcium levels in the cell. As a result of the production of NO by iNOS, it lasts much longer than other forms of isoforms of NOS and tends to produce much higher concentrations of NO in the body. This is likely the reason that iNOS levels are known to be elevated in dementia & Alzheimer's patents and have increased calcium deposits in their brain tissue.

Inducible iNOS levels are highly connected with sepsis infections which typically lead to large levels of NO in the blood stream, which in turns leads to organ failure. Lastly abnormal amounts of nNOS levels are typically associated with issues with blood pressure regulation, neurotransmission issues and penal erection. Thus, the overproduction or underproduction of NO levels may be associated with many different health conditions. These health conditions may be detected by measuring NO levels in tissue and/or in the blood stream of a patient.

Overview of Detection of Sepsis

The signs and symptoms of sepsis may be subtle. The unacceptably low survival rate of severe sepsis indicates that current patient diagnosis strategies are lacking in timeliness and accuracy. SIRS (systemic inflammatory response syndrome) refers to the systemic activation of the body's immune response, such as from sepsis. SIRS is manifested by, for example, the presence of more than one of a temperature greater than 38° C. or less than 36° C.; a heart rate greater than 90 beats/min.; and a respiration rate greater than 20 breaths/min. However, these symptoms may occur too late for an early diagnosis and treatment of sepsis. And sepsis has an 8% mortality rate compounded per hour left untreated.

Conventional tests for sepsis give insufficient advance warning of deteriorating patient health or the onset of potentially serious physiological conditions resulting from sepsis. In conventional tests, blood samples must be taken and blood tests performed to confirm the diagnosis of sepsis. For example, blood tests for sepsis include: CBC complement, CFC, serum lactate levels. These types of blood tests are invasive, non-continuous, costly, and time consuming. Since sepsis is very dangerous and may escalate to be life threatening conditions quickly, this diagnosis process is not sufficient for early warning of sepsis.

It has been shown that sepsis causes an increased amount of nitrous oxide (NO) to be released into the blood stream. The role of nitric oxide in sepsis is described in the article entitled, "Nitric oxide in septic shock," by Michael A. Tiitheradge, Biochimica et Biophysica Acta 1411 (1999) 437-455, which is hereby incorporated by reference herein. As described in the article, a patient in septic shock has hepatic glucose production that causes extreme levels of lactate and amino acids. This in turn accelerates production of Nitric Oxide or related Nitrate compounds to critical levels within the body. The overproduction of NO during sepsis induces excessive vascular relaxation and a profound hypotension that is also a characteristic feature of sepsis.

In one or more embodiments herein, an early warning system and method is described for detection of a risk of sepsis. A biosensor detects NO levels in vivo in the blood stream of a patient. The biosensor includes an optical sensor circuit configured to determine NO levels in arteries, vessels and/or surrounding tissue of a patient. The biosensor may also detect temperature as well as other vital signs indicative of sepsis, such as pulse rate and respiration rate. The biosensor includes a visible or audible indicator that signals NO levels and/or other vital signs indicative of sepsis or the possible onset of sepsis. The biosensor thus provides a noninvasive and continuous monitoring tool for early warning of a patient's condition and allows for more immediate medical intervention.

Embodiment of the Biosensor

In an embodiment, the biosensor includes an optical sensor photoplethysmography (PPG) circuit configured to transmit light at a plurality of wavelengths directed at skin tissue of a patient. The patient may include any living organism, human or non-human. The PPG circuit detects the light reflected from the skin tissue and generates spectral responses at the plurality of wavelengths. The processing circuit is configured to obtain a measurement of NO levels from the spectral responses at the plurality of wavelengths using one or more measurement techniques described herein.

Figure 1A:
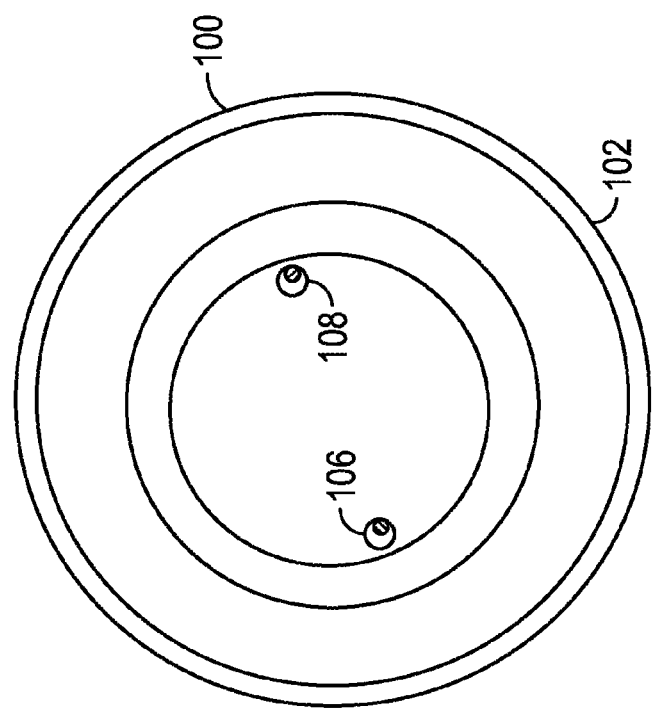
FIG. 1A illustrates a perspective view of an embodiment of a biosensor.

FIG. 1A and FIG. 1B illustrate a perspective view of an embodiment of the biosensor 100. FIG. 1A illustrates a perspective front view of the biosensor 100 while FIG. 1B illustrates a perspective back view of the biosensor 100. In this embodiment, the biosensor 100 is included in a disposable patch form factor 102. The patch 102 may include an adhesive backing 104 such that it may adhere to a patient's skin. The patch 102 may alternatively be secured through other means, such as tape, etc.

The patch includes an optical sensor photoplethysmography (PPG) circuit 110. The PPG circuit is configured to emit light at a plurality of wavelengths that is directed at skin tissue of the patient. The PPG circuit 110 uses one or more photodetectors to detect light reflected from the skin tissue and generates a spectral response for each of the plurality of wavelengths. A processing circuit in the biosensor 100 is configured to obtain a measurement of NO levels from the spectral responses at the plurality of wavelengths using one or more measurement techniques described herein. The NO levels may be continuously monitored by the biosensor 100. For example, the biosensor 100 may obtain the NO measurements a plurality of times over a predetermined time period, such as multiple times per second or per minute. The measurements over the predetermined time period may be averaged to obtain an NO level. The NO level is used to determine a risk of sepsis by comparing the NO level with one or more thresholds indicative of sepsis.

The biosensor 100 further includes a health alert indicator to provide a warning of possible risk of sepsis. The health alert indicator in this embodiment includes a first LED 106. When symptoms of sepsis are detected, the first LED 106 may illuminate to provide a warning. For example, the first LED 106 may illuminate a first color (e.g. green) to indicate no or little risk of sepsis has been detected while a second color (e.g. red) may indicate that symptoms have been detected indicating a risk of sepsis. The biosensor 100 may also measure other patient vitals such as pulse or heart rate, e.g. beats per minute (bpm), respiration rate and temperature. These measurements or vital signs may also be considered when determining whether to provide a warning of a risk of sepsis.

Due to its compact form factor, the patch 102 may be attached on various skin surfaces of a patient, including on a forehead, arm, wrist, abdominal area, chest, leg, hand, etc. The patch 102 in an embodiment is designed to be disposable, e.g. designed to be used on a single patient. For example, the biosensor 100 may include a battery with a relatively short life span of 24-48 hours.

In use, the biosensor 100 is activated and the adhesive backing 104 is peeled and attached to a single patient for monitoring. A second LED 108 may indicate activation of the biosensor 100. For example, when the second LED 108 is illuminated, it indicates that the biosensor 100 is activated and monitoring the patient. When the second LED 108 is not lit, it indicates that monitoring has stopped. When monitoring is complete for that single patient or the battery of the biosensor has lost charge, the patch 102 is removed and thrown away.

Figure 2:
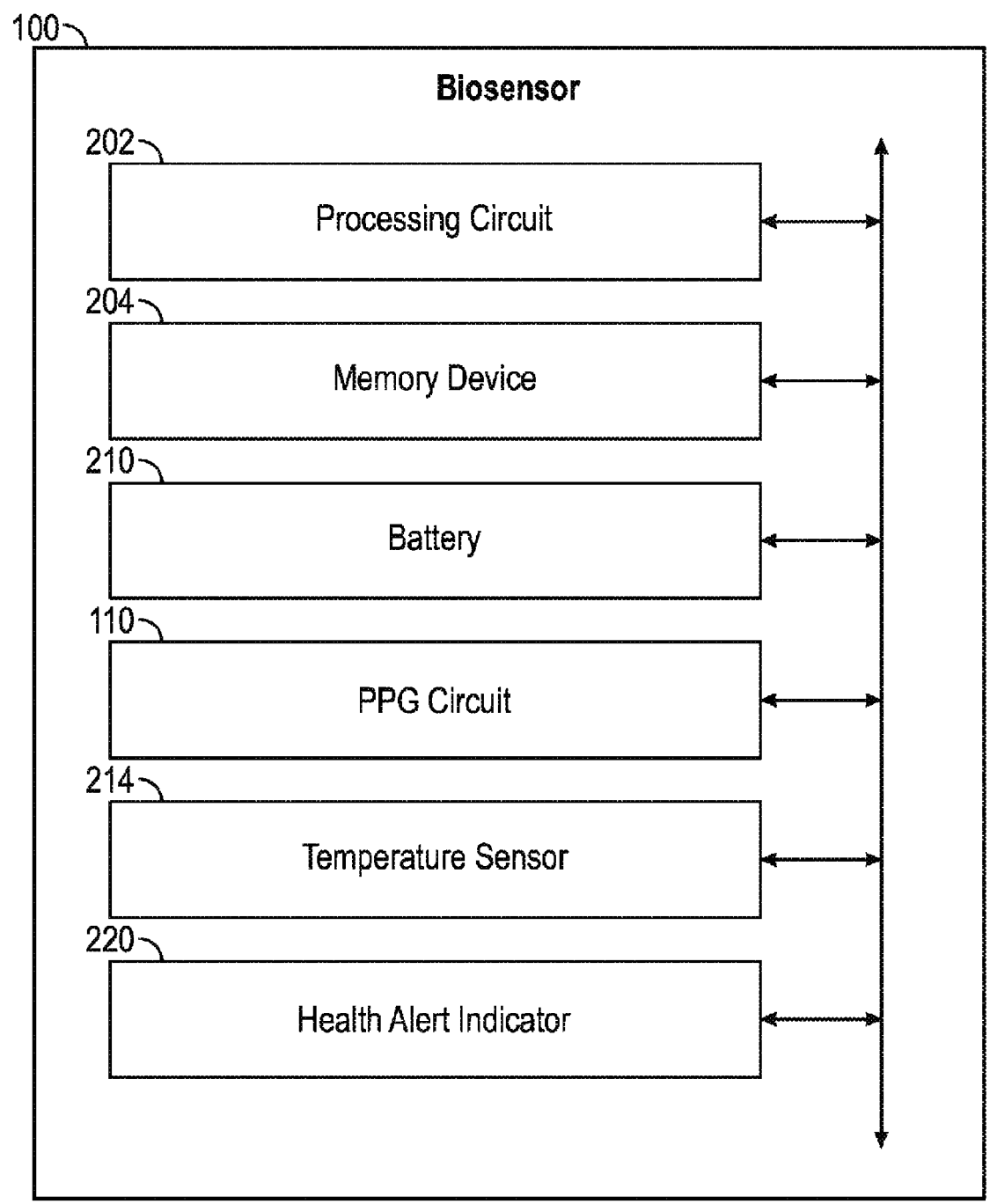
FIG. 2 illustrates a schematic block diagram of exemplary components in an embodiment of the biosensor.

FIG. 2 illustrates a schematic block diagram of exemplary components in an embodiment of the biosensor 100. In this embodiment, the biosensor 100 is designed to be disposable and manufactured at a relatively low cost. The biosensor 100 includes the PPG circuit 110 as described in more detail herein. The PPG circuit 110 may be configured to detect oxygen saturation (SaO2 or SpO2) levels in blood flow, as well as heart rate and respiration rate. In addition, the PPG circuit 110 is configured to detect concentration levels of NO using one or more measurement techniques as described in more detail herein.

The biosensor 100 also includes one or more processing circuits 202 communicatively coupled to a memory device 204. In one aspect, the memory device 204 may include one or more non-transitory processor readable memories that store instructions which when executed by the one or more processing circuits 202, causes the one or more processing circuits 202 to perform one or more functions described herein. The processing circuit 202 may be co-located with one or more of the other circuits of the biosensor 100 in a same physical circuit board or located separately in a different circuit board or encasement. The biosensor 100 is battery operated and includes a battery 210, such as a lithium ion battery. In an embodiment, the battery 210 is designed to include a short lifespan of 24-48 hours.

The biosensor 100 may also include a temperature sensor 214 configured to detect a temperature of a patient. For example, the temperature sensor 214 may include an array of sensors (e.g., 16×16 pixels) positioned on the back of the patch 102 with the PPG circuit 110 such that the array of sensors are adjacent to the skin of the patient. The array of sensors is configured to detect a temperature of the patient from the skin. The temperature sensor 214 may also be used to calibrate the PPG circuit 110.

The biosensor 100 also includes a health alert indicator 220. The health alert indicator 220 may include one or more LEDs or a display.

Figure 3:
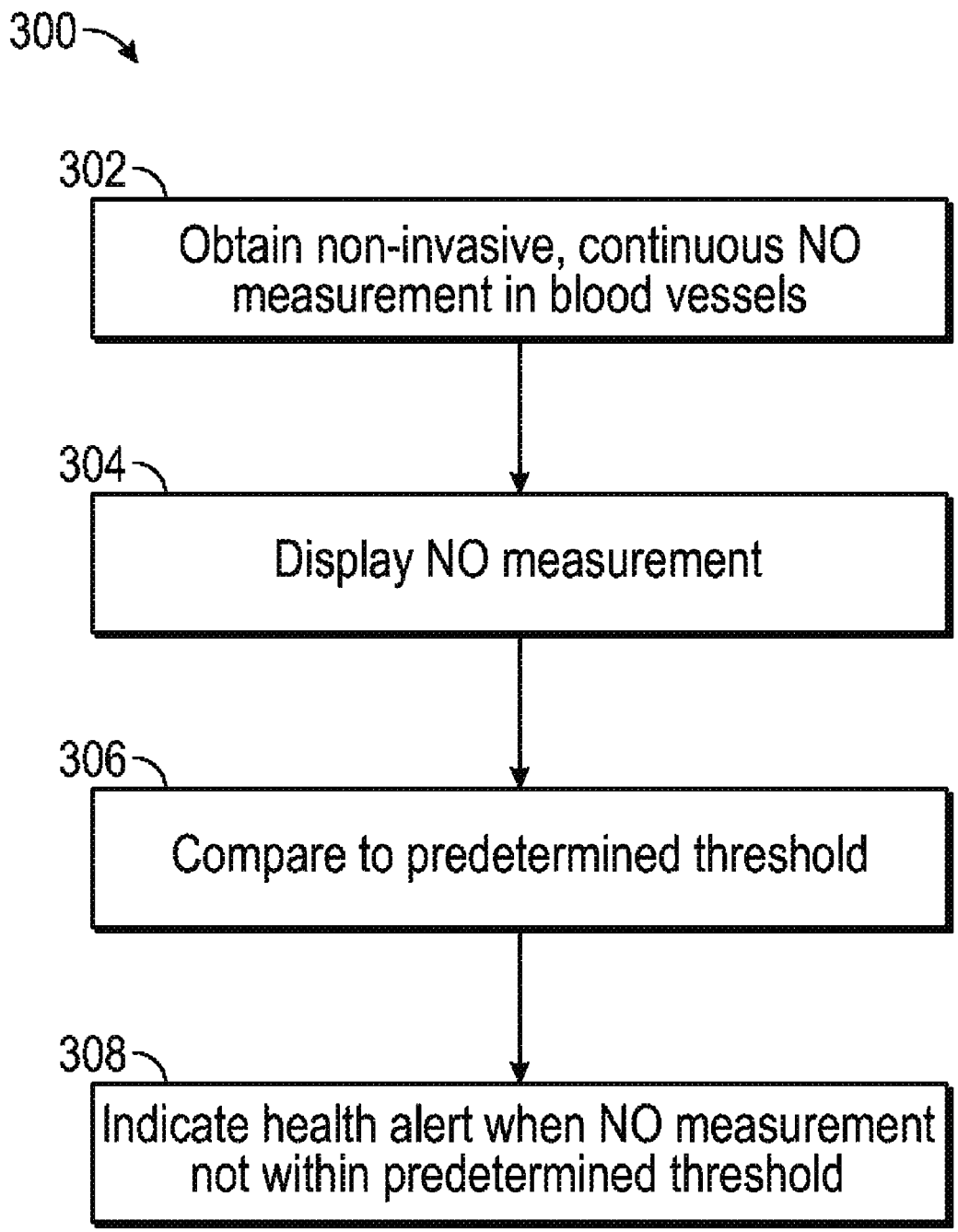
FIG. 3 illustrates a logical flow diagram of an exemplary embodiment of a method for detecting a risk of sepsis by the biosensor.

FIG. 3 illustrates a logical flow diagram of an exemplary embodiment of a method 300 for detecting a risk of sepsis by the biosensor 100. The biosensor 100 non-invasively obtains an NO measurement related to the concentration of NO in blood vessels at 302. An indication of the NO measurement may be displayed at 304. For example, the patch 102 may include a row of LEDs that are illuminated to indicate the level of the NO concentration level. Alternatively, the patch 102 may include an LED configured to illuminate in one or more colors or hues to indicate the level of NO concentration.

The NO measurement of the patient is compared to predetermined levels at 306. For example, the predetermined threshold may be based on a range of average or mean NO measurements of a sample healthy population without a sepsis condition. The NO measurement of an individual patient may then be compared to the normal range derived from the sample healthy population. Depending on the comparison, the NO measurement may be determined within normal ranges. Alternatively, the NO measurement may be determined to be higher than the predetermined normal ranges or not within predetermined threshold indicative of a risk of sepsis. An indication of a health alert may then be displayed when the NO measurement is not within a predetermined threshold indicative of a risk of sepsis at 308.

Figure 4A:
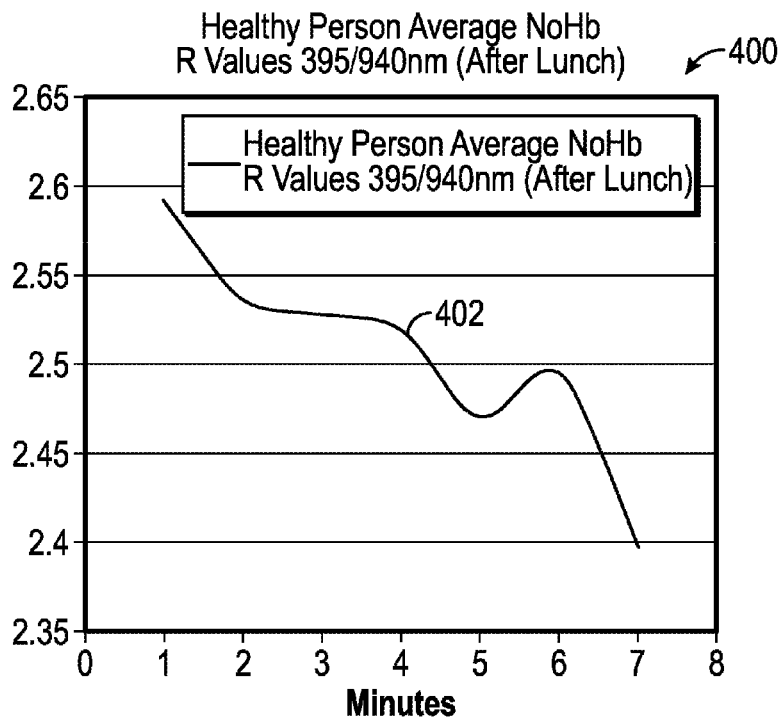
FIG. 4A illustrates a schematic diagram of a graph of actual clinical data obtained using an embodiment of the biosensor.
Figure 4B:
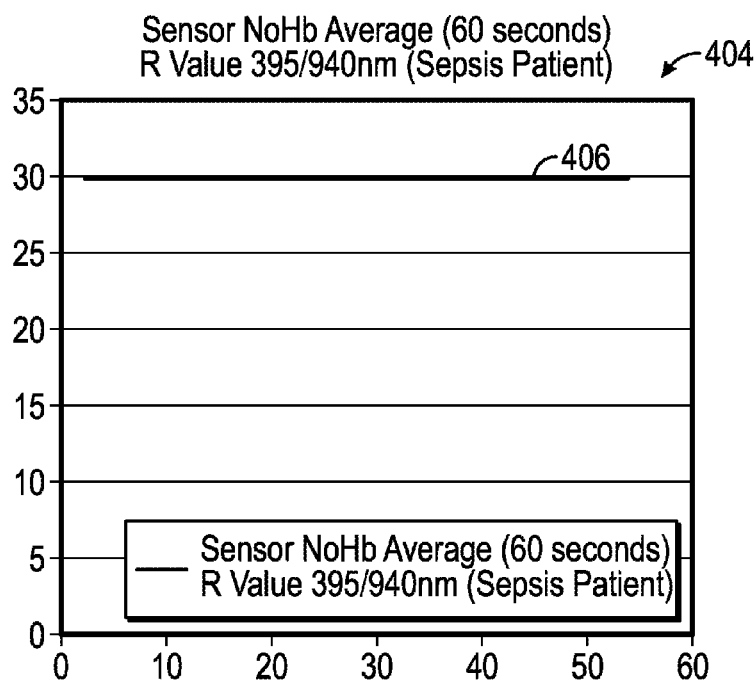
FIG. 4B illustrates a schematic diagram of another graph of actual clinical data obtained using an embodiment of the biosensor.

FIGS. 4A and 4B illustrate schematic diagrams of graphs of actual clinical data obtained using an embodiment of the biosensor 100. FIG. 4A illustrates a graph 400 of a measurement of NO levels for a normal healthy patient. The NO measurement is obtained from a ratio R or R value 402. The R value 402 is obtained from a spectral response in the ultraviolet (UV) range at 395 nm and a spectral response in the infrared (IR) range at 940 nm.

In unexpected results, the UV range from 380 nm to 410 nm, and in particular at 390 nm, has been determined to have a high absorption coefficient for NO. The NO levels in vivo in blood vessels may thus be measured without a need for a blood sample or lab analytics. In this graph 400, the average R value 402 for the healthy patient ranges from 2.6 to 2.4. In general, it has been determined from initial clinical trials that the average R value may range from 0.1 to 8 for a patient without a sepsis condition. In addition, it was determined that an average R value of 30 or higher is indicative of a patient with a sepsis condition and that an average R value of 8-30 was indicative of a risk of sepsis in the patient. In general, an R value of 2-3 times a baseline R value was indicative of a risk of sepsis in the patient.

FIG. 4B illustrates a schematic diagram of a graph 404 of actual clinical data obtained using an embodiment of the biosensor 100 from a patient with a diagnosis of sepsis. The graph 404 illustrates a measurement of NO levels for the patient with sepsis. The NO measurement is obtained from a ratio R or R value 406. The R value 406 is obtained from a spectral response in the UV range and a spectral response in the IR range. In one aspect, the first wavelength in the UV range is from 380-410 nm and in this example, is from an LED with a wavelength of 395 nm. As seen in the graph, R value 406 is around 30 for the patient with sepsis.

Nitric oxide (NO) is found in the blood stream in a gaseous form and also bonded to a plurality of types of hemoglobin species. The measured NO concentration levels obtained using the UV range from 380-410 include measurements of NO in gaseous form as well as the NO bonded to the plurality of types of hemoglobin species in the blood vessels. The measured NO concentration levels may thus include NO in various isoforms, in gaseous form or bonded to a plurality of types of hemoglobin species. The NO measurement levels obtained as described herein are thus more sensitive and have a greater dynamic range than other methods for measuring NO levels based on a single species of hemoglobin, such as methemoglobin (HbMet). The NO measurements herein may also provide an earlier detection of increases in NO in blood vessels than measurements based on HbMet alone. In addition, the NO measurements may also extend to ranges beyond hemoglobin saturation levels.

Figure 5:
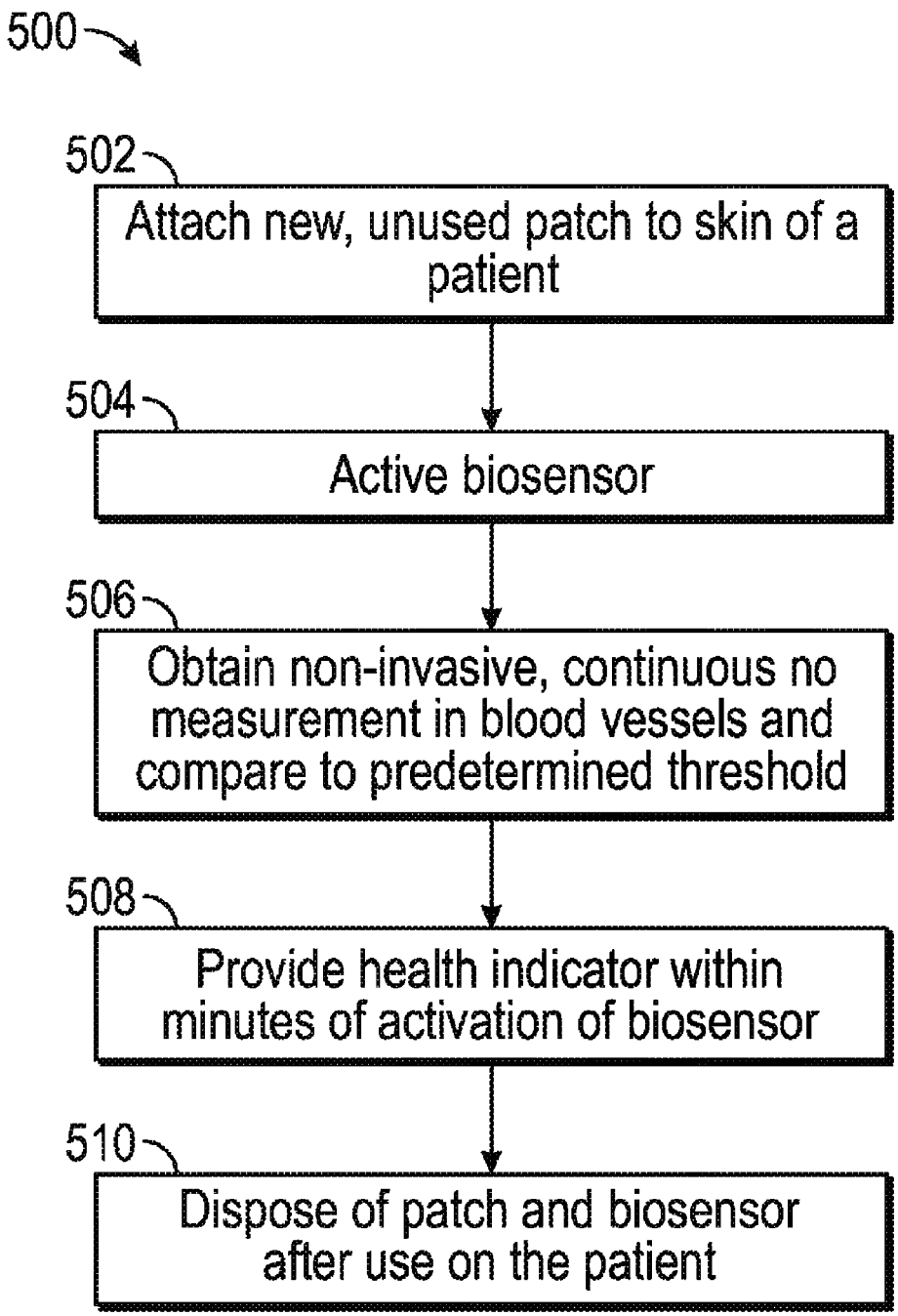
FIG. 5 illustrates illustrates a logical flow diagram of an embodiment of a method for use of the disposable patch.

FIG. 5 illustrates a logical flow diagram of an embodiment of a method 500 for use of the disposable patch 102. In this embodiment, the biosensor 100 is included in a disposable patch form factor 102. A new, unused patch 102 is attached to skin tissue of a patient at 502. The patch 102 may include an adhesive backing 104 such that it may adhere to a patient's skin. The patch 102 may additionally or alternatively be secured through other means, such as tape, band, etc.

The biosensor 100 is activated at 504. For example, a pull tab may be implemented between the battery 210 and biosensor 100 and/or an activation button may be implemented to activate the biosensor 100. The biosensor 100 non-invasively monitors an NO measurement related to the concentration of NO in blood vessels at 506. The NO measurement of the patient is compared to one or more predetermined thresholds. For example, the predetermined thresholds may be derived based on measurements of a sample healthy general population. A mean or range of average values for the NO measurement from the sample healthy population may then be used to set the predetermined thresholds. The NO measurement of the patient may then be compared to the predetermined thresholds derived from the sample healthy population.

Within minutes of activation, the patch 102 may determine the NO measurement and provide a health indicator at 508. Depending on the comparison of the NO measurement to the one or more predetermined thresholds, the health indicator may signal that the NO measurement is within predetermined normal ranges. Alternatively, the health indicator may signal that the NO measurement is not within than the predetermined thresholds, e.g. outside normal ranges or in a range indicative of a patient with sepsis. The health indicator then provides a warning or alert of a risk of sepsis.

To lower costs, the health indicator may include one or more LEDs on the patch 102. For example, the patch 102 may include a row of LEDs that are illuminated to indicate the level of the NO concentration. Alternatively, the patch 102 may include an LED configured to illuminate in one or more colors or hues to indicate the level of NO concentration, a first color to indicate normal ranges and a second color to indicate not within normal ranges. In another embodiment, the patch 102 may include a display that provides a visual indication of the NO concentration.

When monitoring of the single patient is complete, the patch 102 including the biosensor 100 is disposed of. The patch 102 is thus designed and manufactured for a single use on a single patient for a short duration of time, e.g. 24-48 hours.

The disposable patch form factor 102 has several advantages including a low cost (such as under $10). The patch 102 is easy to use with a simple visible indicator. The patch may be sold for hospital or home use to provide a health indicator within minutes. For example, the patch 102 may be used in triage at hospitals or clinics, or the patch 102 may be used at home to monitor an at risk patient to determine a possible infection or risk of sepsis.

Embodiment—PPG Circuit

Figure 6:
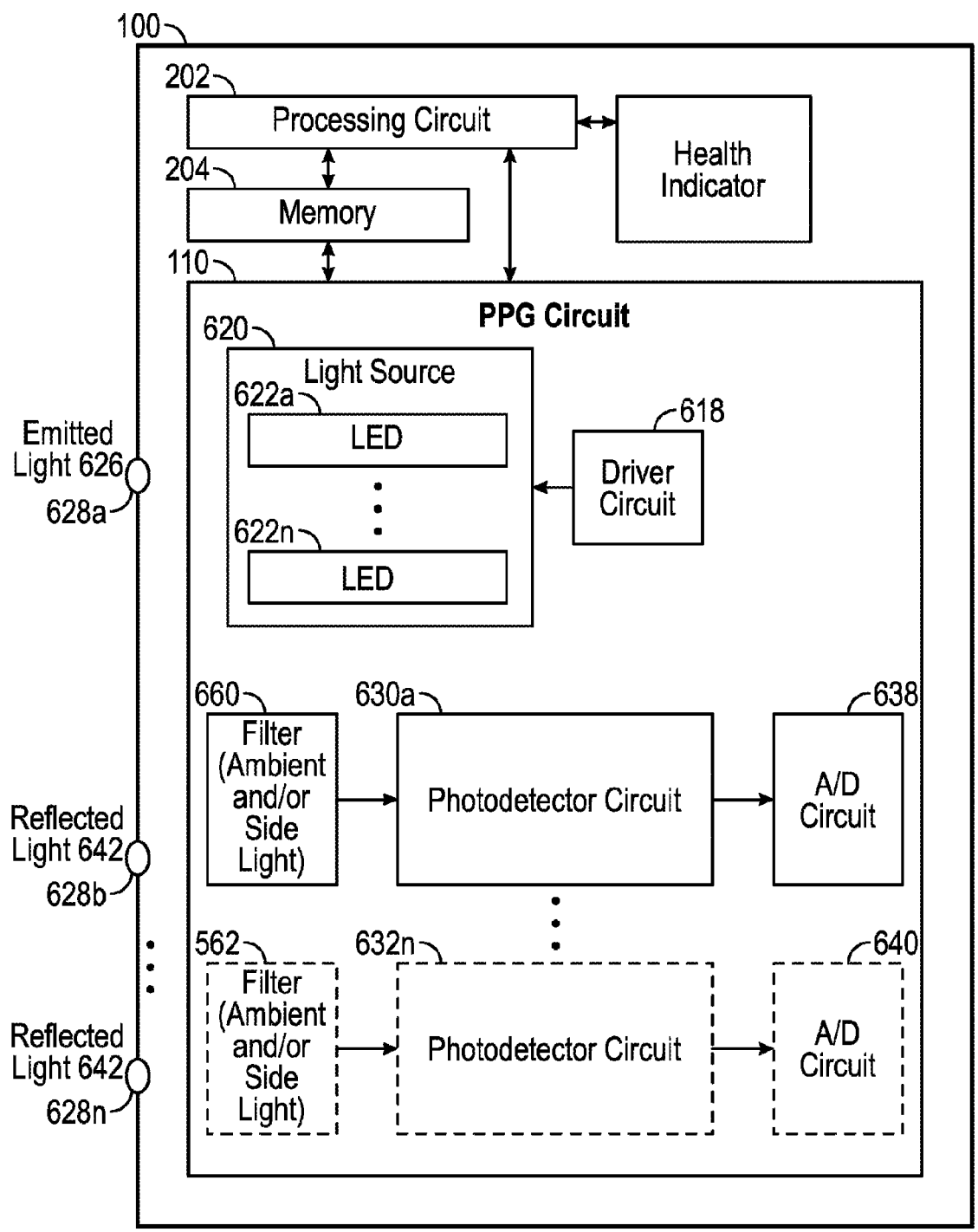
FIG. 6 illustrates a schematic block diagram illustrating an embodiment of the PPG circuit in more detail.

FIG. 6 illustrates a schematic block diagram illustrating an embodiment of the PPG circuit 110 in more detail. The PPG circuit 110 includes a light source 620 configured to emit a plurality of wavelengths of light across various spectrums. For example, the light source 620 mat include a plurality of LEDs 622a-n. The PPG circuit 110 is configured to direct the emitted light at an outer or epidermal layer of skin tissue of a patient through at least one aperture 628a. The plurality of LEDs 622a-n are configured to emit light in one or more spectrums, including infrared (IR) light, ultraviolet (UV) light, near IR light or visible light, in response to driver circuit 618. For example, the biosensor 100 may include a first LED 622a that emits visible light and a second LED 622b that emits infrared light and a third LED 622c that emits UV light, etc. In another embodiment, one or more of the light sources 622a-n may include tunable LEDs or lasers operable to emit light over one or more frequencies or ranges of frequencies or spectrums in response to driver circuit 618.

In an embodiment, the driver circuit 618 is configured to control the one or more LEDs 622a-n to generate light at one or more frequencies for predetermined periods of time. The driver circuit 618 may control the LEDs 622a-n to operate concurrently or consecutively. The driver circuit 618 is configured to control a power level, emission period and frequency of emission of the LEDs 622a-n. The biosensor 100 is thus configured to emit one or more wavelengths of light in one or more spectrums that is directed at the surface or epidermal layer of the skin tissue of a patient.

The PPG circuit 110 further includes one or more photodetector circuits 630a-n. For example, a first photodetector circuit 630 may be configured to detect visible light and the second photodetector circuit 630 may be configured to detect IR light. Alternatively, both photodetectors 630a-n may be configured to detect light across multiple spectrums and the signals obtained from the photodetectors are added or averaged. The first photodetector circuit 630 and the second photodetector circuit 630 may also include a first filter 660 and a second filter 662 configured to filter ambient light and/or scattered light. For example, in some embodiments, only light reflected at an approximately perpendicular angle to the skin surface of the patient is desired to pass through the filters. The first photodetector circuit 630 and the second photodetector circuit 632 are coupled to a first A/D circuit 638 and a second A/D circuit 640. Alternatively, a single A/D circuit may be coupled to each of the photodetector circuits 630a-n.

In another embodiment, a single photodetector circuit 630 may be implemented operable to detect light over multiple spectrums or frequency ranges. The one or more photodetector circuits 630 include one or more types of spectrometers or photodiodes or other type of circuit configured to detect an intensity of light as a function of wavelength to obtain a spectral response. In use, the one or more photodetector circuits 630 detect the intensity of light reflected from skin tissue of a patient that enters one or more apertures 628b-n of the biosensor 100. In another example, the one or more photodetector circuits 630 detect the intensity of light due to transmissive absorption (e.g., light transmitted through tissues such as a fingertip or ear lobe). The one or more photodetector circuits 630a-n then obtain a spectral response of the reflected or transmissive light by measuring an intensity of the light at one or more wavelengths.

In another embodiment, the light source 620 may include a broad spectrum light source, such as a white light to infrared (IR) or near IR LED 622, that emits light with wavelengths from e.g. 350 nm to 2500 nm. Broad spectrum light sources 620 with different ranges may be implemented. In an aspect, a broad spectrum light source 620 is implemented with a range across 100 nm wavelengths to 2000 nm range of wavelengths in the visible, IR and/or UV frequencies. For example, a broadband tungsten light source 620 for spectroscopy may be used. The spectral response of the reflected light is then measured across the wavelengths in the broad spectrum, e.g. from 350 nm to 2500 nm, concurrently. In an aspect, a charge coupled device (CCD) spectrometer may be configured in the photodetector circuit 630 to measure the spectral response of the detected light over the broad spectrum.

Embodiment—PPG Measurement of NO Levels

One or more of the embodiments of the biosensor 100 described herein is configured to detect a concentration level or indicator of NO within arterial blood flow using photoplethysmography (PPG) techniques. The biosensor 100 may detect NO concentration levels as well as peripheral oxygen ($SpO_2$ or $SaO_2$) saturation, concentration of one or more other substances as well as patient vitals, such as pulse rate and respiration rate. Because blood flow to the skin can be modulated by multiple other physiological systems, the PPG sensor 110 may also be used to monitor hypovolemia and other circulatory conditions.

In use, the biosensor 100 performs PPG techniques using the PPG circuit 110 to detect the concentration levels of one or more substances in blood flow. In one aspect, the biosensor 100 receives reflected light from skin tissue to obtain a spectral response. The spectral response includes a spectral curve that illustrates an intensity or power or energy at a frequency or wavelength in a spectral region of the detected light. The ratio of the resonance absorption peaks from two different frequencies can be calculated and based on the Beer-Lambert law used to obtain the levels of substances in the blood flow.

First, the spectral response of a substance or substances in the arterial blood flow is determined in a controlled environment, so that an absorption coefficient $\alpha_{g1}$ can be obtained at a first light wavelength $\lambda_1$ and at a second wavelength $\lambda_2$. According to the Beer-Lambert law, light intensity will decrease logarithmically with path length l (such as through an artery of length l). Assuming then an initial intensity $I_{in}$ of light is passed through a path length l, a concentration $C_g$ of a substance may be determined using the following equations:

At the first wavelength $\lambda_1$, $I_1 = I_{in1} * 10^{-(\alpha_{g1}C_{gw} + \alpha_{w1}C_w)*l}$ At the second wavelength $\lambda_2$, $I_2 = I_{in2} * 10^{-(\alpha_{g2}C_{gw} + \alpha_{w2}C_w)*l}$ wherein:
$I_{In1}$ is the intensity of the initial light at $\lambda_1$
$I_{in2}$ is the intensity of the initial light at $\lambda_2$
$\alpha_{g1}$ is the absorption coefficient of the substance in arterial blood at $\lambda_1$
$\alpha_{g2}$ is the absorption coefficient of the substance in arterial blood at $\lambda_2$
$\alpha_{w1}$ is the absorption coefficient of arterial blood at $\lambda_1$
$\alpha_{w2}$ is the absorption coefficient of arterial blood at $\lambda_2$
$C_{gw}$ is the concentration of the substance and arterial blood
$C_w$ is the concentration of arterial blood
Then letting R equal:

$$R = \frac{\log 10\left(\frac{I_1}{I in_1}\right)}{\log 10\left(\frac{I_2}{I in_2}\right)}$$

The concentration of the substance Cg may then be equal to:

$$Cg = \frac{Cgw}{Cgw + Cw} = \frac{\alpha_{w2}R - \alpha_{w1}}{(\alpha_{w2} - \alpha_{gw2})*R - (\alpha_{w1} - \alpha_{gw1})}$$

The biosensor 100 may thus determine the concentration of various substances in arterial blood flow from the Beer-Lambert principles using the spectral responses of at least two different wavelengths.

FIG. 7 illustrates a logical flow diagram of an embodiment of a method 700 for determining concentration level of NO using Beer-Lambert principles. The biosensor 100 transmits light at least at a first predetermined wavelength and at a second predetermined wavelength. The biosensor 100 detects the light (reflected from the skin or transmitted through the skin) and determines the spectral response at the first wavelength at 702 and at the second wavelength at 704. The biosensor 100 then determines an indicator or concentration level of NO using the spectral responses of the first and second wavelength at 706. In general, the first predetermined wavelength is selected that has a high absorption coefficient for NO while the second predetermined wavelength is selected that has a lower absorption coefficient for NO. Thus, it is generally desired that the spectral response for the first predetermined wavelength have a higher intensity level in response to NO than the spectral response for the second predetermined wavelength. In an embodiment, the first predetermined wavelength is in a range of 380-410 nm and in particular at 390 nm or 395 nm.

In another aspect, the biosensor 100 may transmit light at the first predetermined wavelength in a range of approximately 1 nm to 50 nm around the first predetermined wavelength. Similarly, the biosensor 100 may transmit light at the second predetermined wavelength in a range of approximately 1 nm to 50 nm around the second predetermined wavelength. The range of wavelengths is determined based on the spectral response since a spectral response may extend over a range of frequencies, not a single frequency (i.e., it has a nonzero linewidth). The light that is reflected or transmitted by NO may spread over a range of wavelengths rather than just the single predetermined wavelength. In addition, the center of the spectral response may be shifted from its nominal central wavelength or the predetermined wavelength. The range of 1 nm to 50 nm is based on the bandwidth of the spectral response line and should include wavelengths with increased light intensity detected for the targeted substance around the predetermined wavelength.

The first spectral response of the light over the first range of wavelengths including the first predetermined wavelength and the second spectral response of the light over the second range of wavelengths including the second predetermined wavelengths is then generated at 702 and 704. The biosensor 100 analyzes the first and second spectral responses to detect an indicator or concentration level of NO in the arterial blood flow at 706.

Figure 8A:
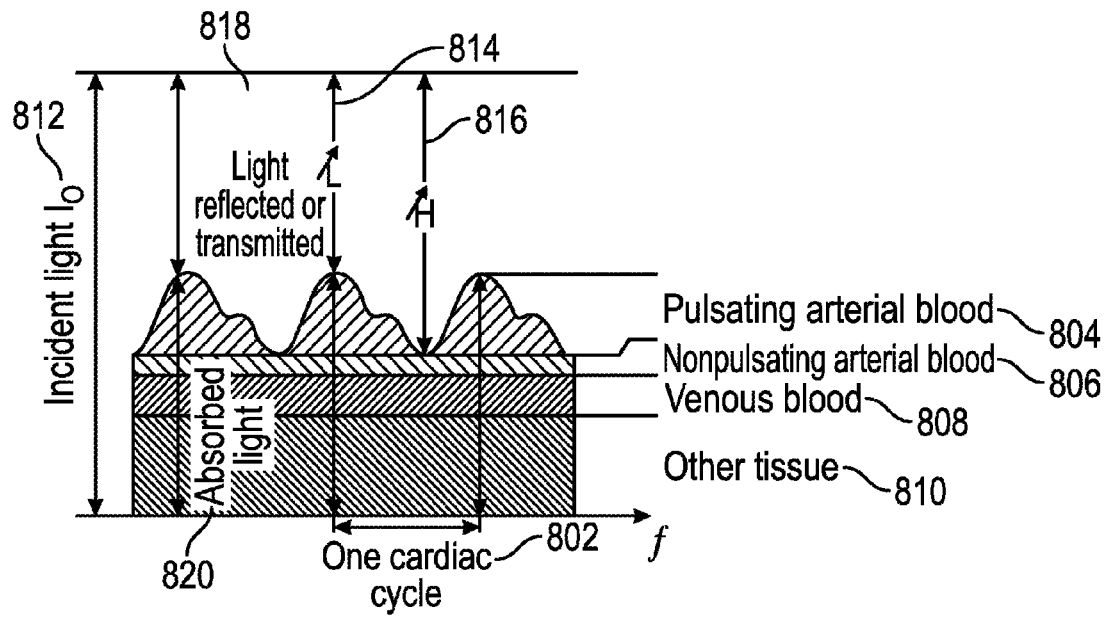
FIG. 8A illustrates a schematic block diagram of an embodiment of a method for photoplethysmography (PPG) techniques in more detail
Figure 8B:
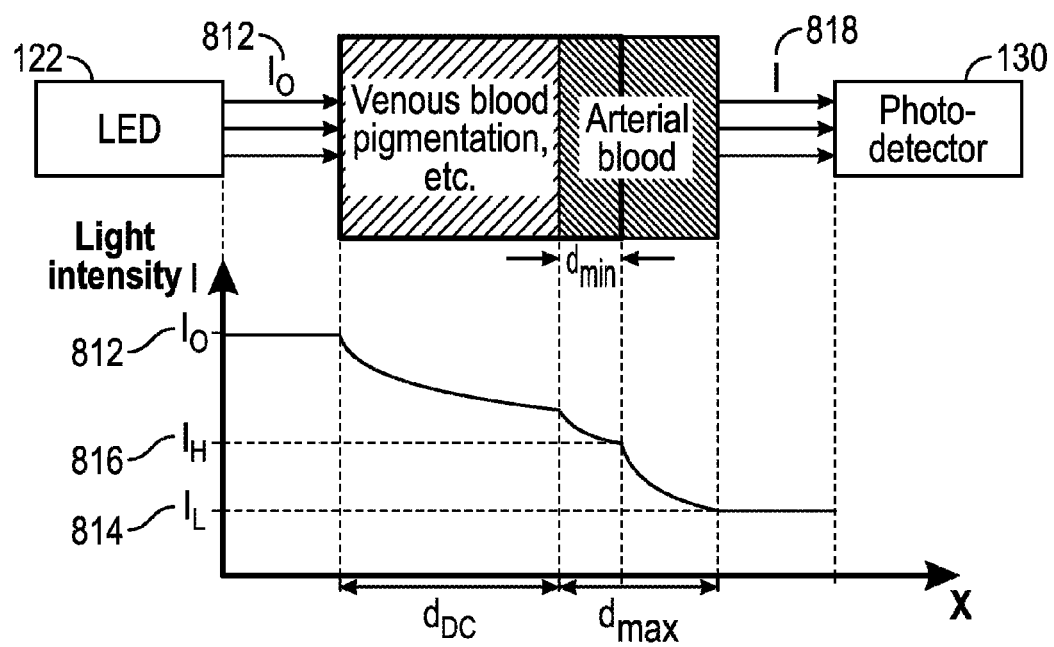
FIG. 8B illustrates a schematic block diagram of an embodiment of a method for photoplethysmography (PPG) techniques in more detail.

FIG. 8A and FIG. 8B illustrate schematic block diagrams of an embodiment of a method for photoplethysmography (PPG) techniques in more detail. Photoplethysmography (PPG) is used to measure time-dependent volumetric properties of blood in blood vessels due to the cardiac cycle. For example, the heartbeat affects the volume of arterial blood flow and the concentration or absorption levels of substances being measured in the arterial blood flow. As shown in FIG. 8A, over a cardiac cycle 802, pulsating arterial blood 804 changes the volume of blood flow in an artery.

Incident light $I_O$ 812 is directed at a tissue site and a certain amount of light is reflected or transmitted 818 and a certain amount of light is absorbed 820. At a peak of arterial blood flow or arterial volume, the reflected/transmitted light $I_L$ 814 is at a minimum due to absorption by the venous blood 808, nonpulsating arterial blood 806, pulsating arterial blood 804, other tissue 810, etc. At a minimum of arterial blood flow or arterial volume during the cardiac cycle, the transmitted/reflected light $I_H$ 816 is at a maximum due to lack of absorption from the pulsating arterial blood 804.

The biosensor 100 is configured to filter the reflected/transmitted light $I_L$ 814 of the pulsating arterial blood 804 from the transmitted/reflected light $I_H$ 816. This filtering isolates the light due to reflection/transmission of substances in the pulsating arterial blood 804 from the light due to reflection/transmission from venous (or capillary) blood

808, other tissues 810, etc. The biosensor 100 may then measure the concentration levels of one or more substances from the reflected/transmitted light $I_L$ 814 in the pulsating arterial blood flow 804.

For example, as shown in FIG. 8B, incident light $I_O$ 812 is directed at a tissue site by an LED 122 at one or more wavelengths. The reflected/transmitted light I 818 is detected by photodetector 130. At a peak of arterial blood flow or arterial volume, the reflected light $I_L$ 814 is at a minimum due to absorption by venous blood 808, non-pulsating arterial blood 806, pulsating arterial blood 804, other tissue 810, etc. At a minimum of arterial blood flow or arterial volume during the cardiac cycle, the Incident or reflected light $I_H$ 816 is at a maximum due to lack of absorption from the pulsating arterial blood 804. Since the light I 818 is reflected or traverses through a different volume of blood at the two measurement times, the measurement provided by a PPG sensor is said to be a 'volumetric measurement' descriptive of the differential volumes of blood present at a certain location within the patient's arteriolar bed at different times. Though the above has been described with respect to arterial blood flow, the same principles described herein may be applied to venous blood flow.

In general, the relative magnitudes of the AC and DC contributions to the reflected/transmitted light signal I 818 may be used to substantially determine the differences between the diastolic points and the systolic points. In this case, the difference between the reflected light $I_L$ 814 and reflected light $I_H$ 816 corresponds to the AC contribution of the reflected light 818 (e.g. due to the pulsating arterial blood flow). A difference function may thus be computed to determine the relative magnitudes of the AC and DC components of the reflected light I 818 to determine the magnitude of the reflected light $I_L$ 814 due to the pulsating arterial blood 804. The described techniques herein for determining the relative magnitudes of the AC and DC contributions is not intended as limiting. It will be appreciated that other methods may be employed to isolate or otherwise determine the relative magnitude of the light $I_L$ 814 due to pulsating arterial blood flow.

Figure 9:
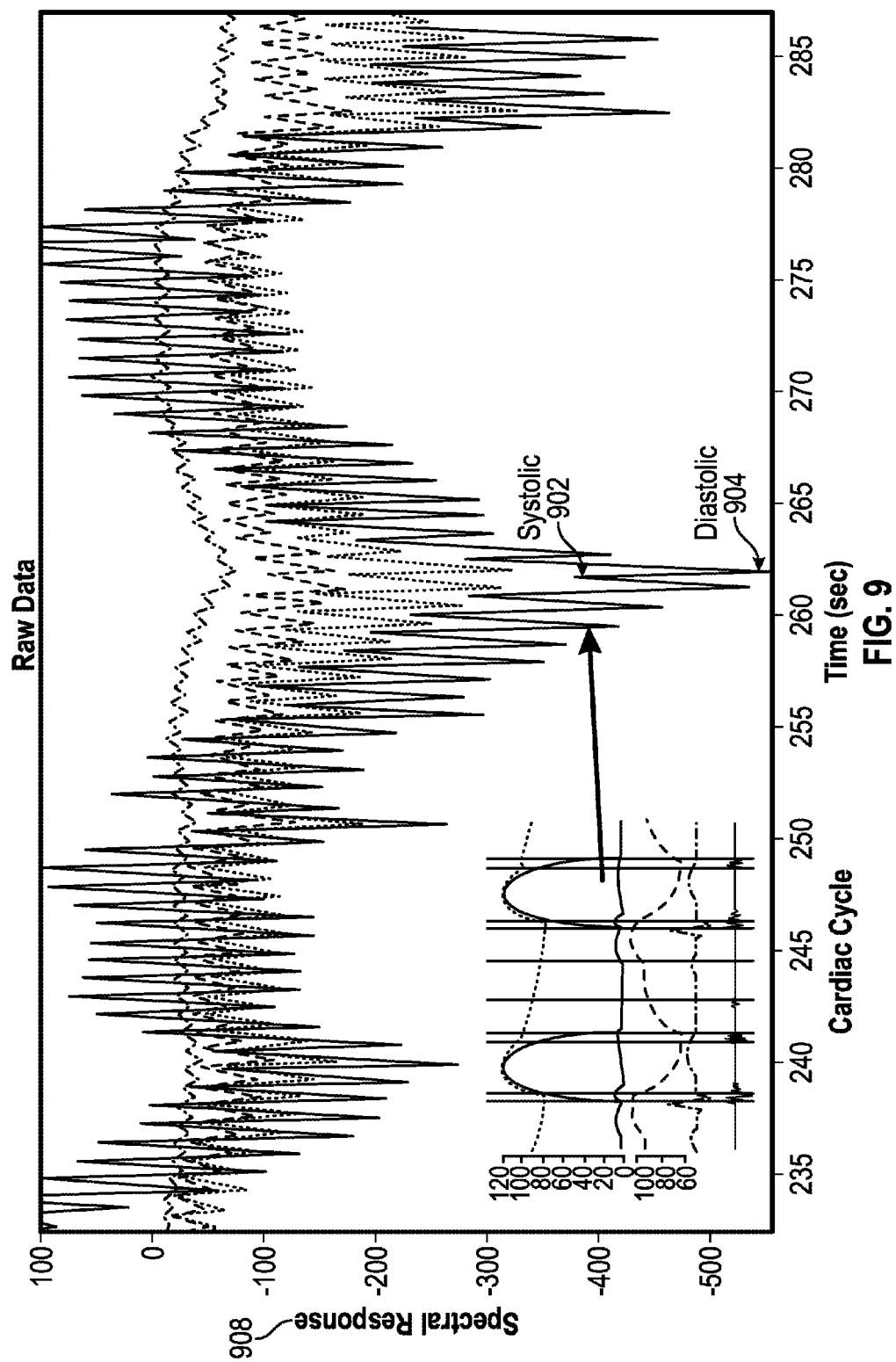
FIG. 9 illustrates a schematic diagram of a graph of actual clinical data obtained using PPG techniques at a plurality of wavelengths.

FIG. 9 illustrates a schematic diagram of a graph of actual clinical data obtained using an embodiment of the biosensor 100 and PPG techniques at a plurality of wavelengths. In one aspect, the biosensor 100 is configured to emit light having a plurality of wavelengths during a measurement period. The light at each wavelength (or range of wavelengths) may be transmitted concurrently or sequentially. The intensity of the reflected light at each of the wavelengths (or range of wavelengths) is detected and the spectral response is measured over the measurement period. The spectral response 908 for the plurality of wavelengths obtained using an embodiment of the biosensor in clinical trials is shown in FIG. 9. In this clinical trial, two biosensors 100 attached to two separate fingertips of a patient were used to obtain the spectral responses 908. The first biosensor 100 obtained the spectral response for a wavelength at 940 nm 610, a wavelength at 660 nm 612 and a wavelength at 390 nm 614. The second biosensor 100 obtained the spectral response for a wavelength at 940 nm 616, a wavelength at 592 nm 618 and a wavelength at 468 nm 620.

In one aspect, the spectral response of each wavelength may be aligned based on the systolic 602 and diastolic 604 points in their spectral responses. This alignment is useful to associate each spectral response with a particular stage or phase of the pulse-induced local pressure wave within the blood vessel (which may mimic the cardiac cycle 906 and thus include systolic and diastolic stages and sub-stages thereof). This temporal alignment helps to determine the absorption measurements acquired near a systolic point in time of the cardiac cycle and near the diastolic point in time of the cardiac cycle 906 associated with the local pressure wave within the patient's blood vessels. This measured local pulse timing information may be useful for properly interpreting the absorption measurements in order to determine the relative contributions of the AC and DC components measured by the biosensor 100. So for one or more wavelengths, the systolic points 902 and diastolic points 904 in the spectral response are determined. These systolic points 902 and diastolic points 904 for the one or more wavelengths may then be aligned as a method to discern concurrent responses across the one or more wavelengths.

In another embodiment, the the systolic points 902 and diastolic points 904 in the absorbance measurements are temporally correlated to the pulse-driven pressure wave within the arterial blood vessels—which may differ from the cardiac cycle. In another embodiment, the biosensor 100 may concurrently measure the intensity reflected at each the plurality of wavelengths. Since the measurements are concurrent, no alignment of the spectral responses of the plurality of wavelengths may be necessary. FIG. 9 illustrates the spectral response of the plurality of wavelengths with the systolic points 902 and diastolic points 904 aligned.

Figure 10:
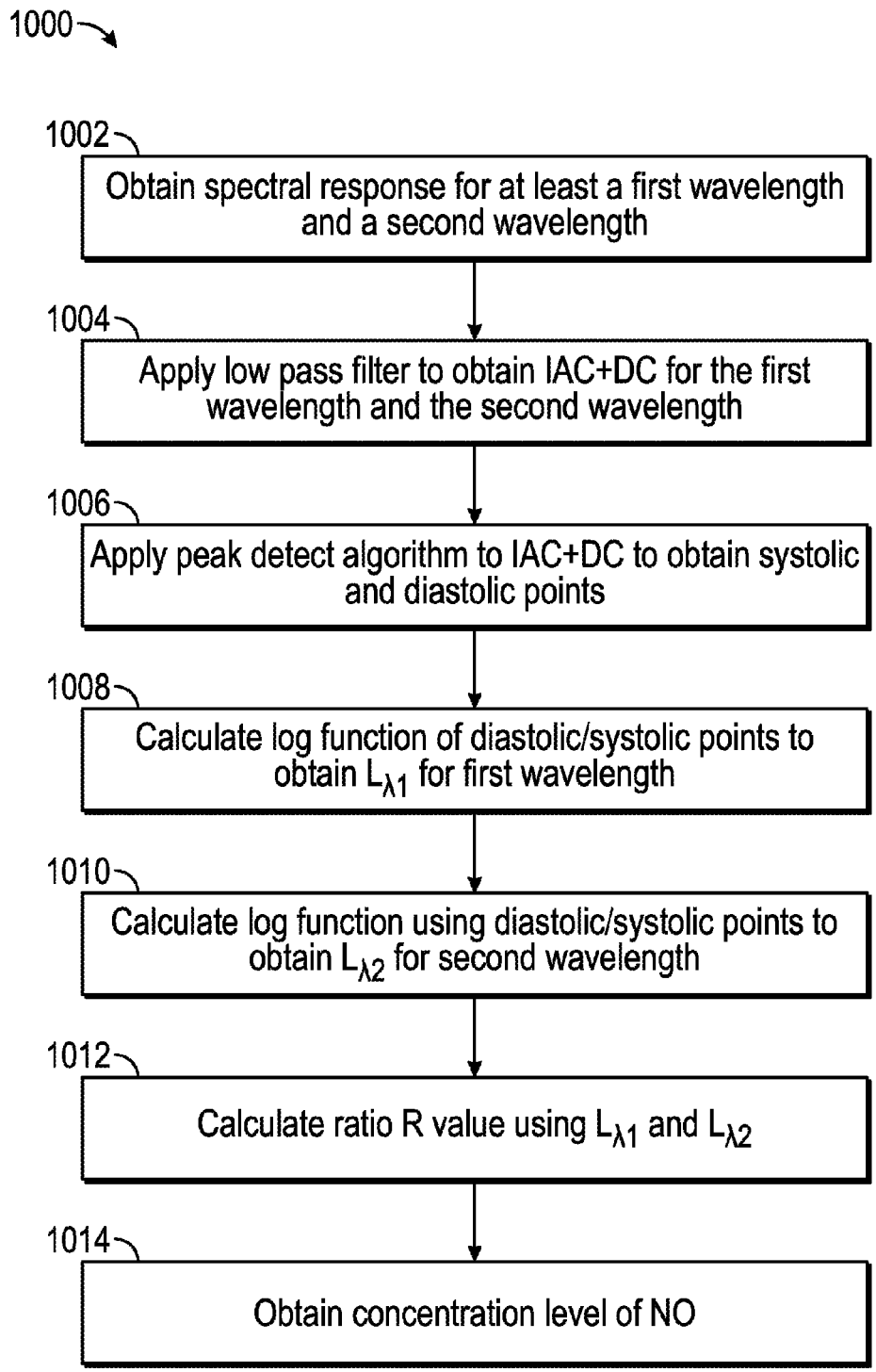
FIG. 10 illustrates a logical flow diagram of an embodiment of a method of the biosensor.

FIG. 10 illustrates a logical flow diagram of an embodiment of a method 1000 of the biosensor 100. In one aspect, the biosensor 100 emits and detects light at a plurality of predetermined frequencies or wavelengths, such as approximately 940 nm, 660 nm, 390 nm, 592 nm, and 468 nm. The light is pulsed for a predetermined period of time (such as 100 usec or 200 Hz) sequentially or simultaneously at each predetermined wavelength. In another aspect, light may be pulsed in a wavelength range of 1 nm to 50 nm around each of the predetermined wavelengths. For example, for the predetermined wavelength 390 nm, the biosensor 100 may transmit light directed at skin tissue of the patient in a range of 360 nm to 410 nm including the predetermined wavelength 390 nm. For the predetermined wavelength of 940 nm, the biosensor 100 may transmit light directed at the skin tissue of the patient in a range of 920 nm to 975 nm. In another embodiment, the light is pulsed simultaneously at least at each of the predetermined wavelengths (and in a range around the wavelengths).

The spectral responses are obtained around the plurality of wavelengths, including at least a first wavelength and a second wavelength at 1002. The spectral responses may be measured over a predetermined period (such as 300 usec.). This measurement process is repeated continuously, e.g., pulsing the light at 10-100 Hz and obtaining spectral responses over a desired measurement period, e.g. from 1-2 seconds to 1-2 minutes or from 2-3 hours to continuously over days or weeks. The absorption levels are measured over one or more cardiac cycles and systolic and diastolic points of the spectral response are determined. Because the human pulse is typically on the order of magnitude of one 1 Hz, typically the time differences between the systolic and diastolic points are on the order of magnitude of milliseconds or tens of milliseconds or hundreds of milliseconds. Thus, spectral response measurements may be obtained at a frequency of around 10-100 Hz over the desired measurement period. The spectral responses are obtained over one or more cardiac cycles and systolic and diastolic points of the spectral responses are determined.

A low pass filter (such as a 5 Hz low pass filter) is applied to the spectral response signal at 1004. The relative contributions of the AC and DC components are obtained $I_{AC+DC}$ and $I_{AC}$. A peak detection algorithm is applied to determine the systolic and diastolic points at 1006. The systolic and diastolic points of the spectral response for each of the wavelengths may be aligned and may also be aligned with systolic and diastolic points of an arterial pulse waveform or cardiac cycle.

Beer Lambert equations are then applied as described herein at 1008. For example, the $L_\lambda$ values are then calculated for the wavelengths $\lambda$, wherein the $\lambda$ values for a wavelength equals:

$$L_\lambda = \text{Log}10\left(\frac{IAC+DC}{IDC}\right)$$

wherein $I_{AC+DC}$ is the intensity of the detected light with AC and DC components and $I_{DC}$ is the intensity of the detected light with the AC filtered by the low pass filter. The value $L_\lambda$ isolates the spectral response due to pulsating arterial blood flow, e.g. the AC component of the spectral response.

A ratio R of the $L_\lambda$ values at two wavelengths may then be determined. For example, $$\text{Ratio } R = \frac{L\lambda 1}{L\lambda 2}$$

The spectral responses may be measured and the $L_\lambda$ values and Ratio R determined continuously, e.g. every 1-2 seconds, and the obtained $L_\lambda$ values and/or Ratio R averaged over a predetermined time period, such as over 1-2 minutes. The NO concentration levels may then be obtained from the averaged R values and a calibration database. The biosensor 100 may continuously monitor a patient over 2-3 hours or continuously over days or weeks.

The $R_{390,940}$ value with $L_{\lambda 1=390\ nm}$ and $L_{\lambda 2=940}$ may be non-invasively and quickly and easily obtained using the biosensor 100 in a physician's office or other clinical setting or at home. In particular, in unexpected results, it is believed that nitric oxide NO levels in the arterial blood flow is being measured at least in part by the biosensor 100 at wavelengths in the range of 380-410 and in particular at $\lambda_1=390$ nm. Thus, the biosensor 100 measurements to determine the $L_{390\ nm}$ values are the first time NO concentration levels in arterial blood flow have been measured directly in vivo. These and other aspects of the biosensor 100 are described in more detail herein with clinical trial results.

Figure 11:
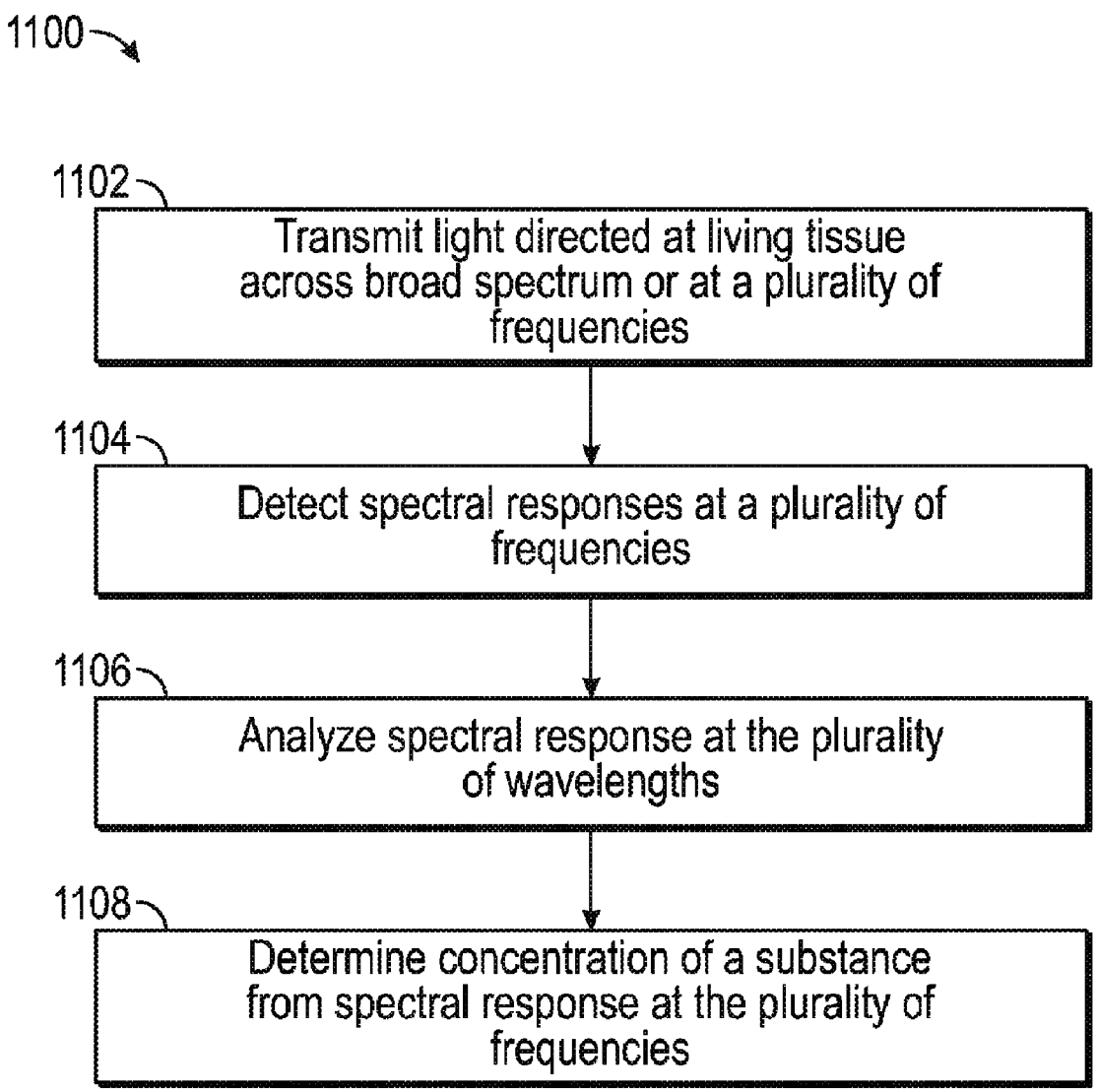
FIG. 11 illustrates a logical flow diagram of an exemplary method to determine levels of NO using the spectral response at a plurality of wavelengths.

Embodiment—Determination of NO Concentration Levels at a Plurality of Wavelengths FIG. 11 illustrates a logical flow diagram of an exemplary method 1100 to determine levels of NO using the spectral response at a plurality of wavelengths. The absorption coefficient may be higher at other wavelengths due to NO or NO isoforms or NO compounds. For example, the increased intensity of light at a plurality of wavelengths may be due to reflectance by NO or NO isoforms or other NO compounds in the arterial blood flow. Another method for determining NO levels may then be used by measuring the spectral response and determining L and R values at a plurality of different wavelengths of light. In this example then, NO concentration level is determined over multiple wavelengths. An example for calculating the concentration of one or more substances over multiple wavelengths may be performed using a linear function, such as is illustrated herein below.

$$LN(I_{1-n}) = \Sigma_{i=0}^{n} \mu i * Ci$$

wherein, $I_{1-n}$=intensity of light at wavelengths $\lambda_{1-n}$ $\mu_n$=absorption coefficient of substance 1, 2, . . . n at wavelengths $\lambda_{1-n}$ $C_n$=Concentration level of substance 1, 2, . . . n When the absorption coefficients $\mu_{1-n}$ of NO or NOS isoforms or other NO compounds are known at the wavelengths $\lambda_{1-n}$, then the concentration level C of the substances may be determined from the spectral responses at the wavelengths $\lambda_{1-n}$ (and e.g., including a range of 1 nm to 50 nm around each of the wavelengths). The concentration level of NO may be isolated from the NOS isoforms or other NO compounds by compensating for the concentration of the hemoglobin compounds. Thus, using the spectral responses at multiple frequencies provides a more robust determination of the concentration level of NO.

In use, the biosensor 100 transmits light directed at skin tissue at a plurality of wavelengths or over a broad spectrum at 1102. The spectral response of light from the skin tissue is detected at 1104, and the spectral response is analyzed for a plurality of wavelengths (and in one aspect including a range of +/−10 to 50 nm around each of the wavelengths) at 1106. Then, the concentration level C of the substance may be determined using the spectral response at the plurality of wavelengths at 1108.

Figure 12:
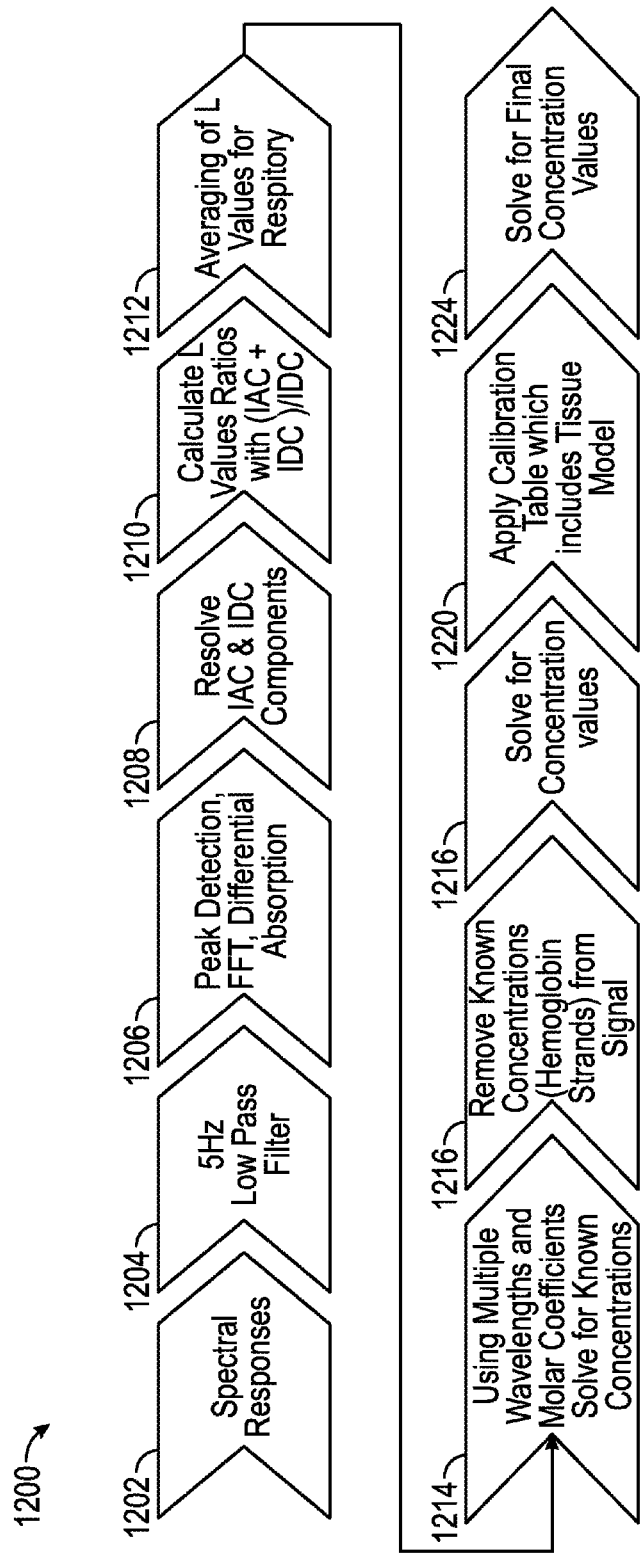
FIG. 12 illustrates a logical flow diagram of an exemplary method to determine levels of NO using the spectral response at a plurality of wavelengths in more detail.

FIG. 12 illustrates a logical flow diagram of an exemplary method 1200 to determine levels of NO using the spectral response at a plurality of wavelengths in more detail. The spectral responses are obtained at 1202. The spectral response signals include AC and DC components $I_{AC+DC}$. A low pass filter (such as a 5 Hz low pass filter) is applied to each of the spectral response signals $I_{AC+DC}$ to isolate the DC component of each of the spectral response signals $I_{DC}$ at 1204. The AC fluctuation is due to the pulsatile expansion of the arteriolar bed due to the volume increase in arterial blood. In order to measure the AC fluctuation, measurements are taken at different times and a peak detection algorithm is used to determine the diastolic point and the systolic point of the spectral responses at 1206. Fast Fourier transform (FFT) or differential absorption techniques may also be used to isolate the DC component of each spectral response signal. The various methods include one or more of: Peak & Valley (e.g., peak detection), FFT, and differential absorption. Each of the methods require different amounts of computational time which affects overall embedded computing time for each signal, and therefore can be optimized and selectively validated with empirical data through large clinical sample studies.

The $I_{AC+DC}$ and $I_{DC}$ components are then used to compute the L values at 1210. For example, a logarithmic function may be applied to the ratio of $I_{AC+DC}$ and $I_{DC}$ to obtain an L value for each of the wavelengths $L_{\lambda 1-n}$. Since the respiratory cycle affects the PPG signals, the L values may be averaged over a respiratory cycle and/or over another predetermined time period (such as over a 1-2 minute time period).

In an embodiment, NO isoforms may be attached in the blood stream to one or more types of hemoglobin compounds. The concentration level of the hemoglobin compounds may then need to be accounted for to isolate the concentration level of NO from the hemoglobin compounds. For example, nitric oxide (NO) is found in the blood stream in a gaseous form and also attached to hemoglobin compounds as described herein. Thus, the spectral responses obtained around 390 nm may include a concentration level of the hemoglobin compounds as well as nitric oxide. The hemoglobin compound concentration levels must thus be compensated for to isolate the nitric oxide concentration levels. Multiple wavelengths and absorption coefficients for hemoglobin are used to determine a concentration of the hemoglobin compounds at 1214. This process is discussed in more detail herein below. Other methods may also be used to obtain a concentration level of hemoglobin in the arterial blood flow as explained herein. The concentration of the hemoglobin compounds is then adjusted from the measurements to determine the concentration level of NO at 1216. The R values are then determined at 1218.

To determine a concentration level of NO, a calibration database is used that associates R values to concentration levels of NO at 1220. The calibration database correlates the R value with an NO concentration level. The calibration database may be generated for a specific patient or may be generated from clinical data of a large sample population. It is determined that the R values should correlate to similar NO concentration levels across a large sample population. Thus, the calibration database may be generated from testing of a large sample of a general population.

In addition, the R values may vary depending on various factors, such as underlying skin tissue. For example, the R values may vary for spectral responses obtained from an abdominal area versus measurements from a wrist or finger due to the varying tissue characteristics. The calibration database may thus provide different correlations between the R values and NO concentration levels depending on the underlying skin tissue characteristics.

The NO concentration level is then obtained at 1224. The NO concentration level may be expressed as mmol/liter, as a saturation level percentage, as a relative level on a scale, etc. In order to remove the hemoglobin concentration(s) from the original PPG signals, a mapping function may be created which is constructed through clinical data and tissue modeling. For example, known $SpO_2$ values in the infrared region and the same signals at the UV side of the spectrum are obtained. Then a linear inversion map can be constructed where the R values are input into a function and the desired concentration(s) can be determined. For example, a curve that correlates R values to concentration levels may be tabulated. A polynomial equation with multiple factors can also be used to account for different R values to represent the linear inversion map. This correlation may be derived from validated clinical data.

For example, a regression curve that correlates R values and NO concentration levels may be generated based on clinical data from a large general population. A polynomial may be derived from the curve and used to solve for an NO concentration level from the R value. The polynomial is stored in the calibration database and may be used rather than using a calibration look-up table or curve.

Embodiment—Determination of a Concentration of Hemoglobin Compounds

The Beer-Lambert theory may be generalized for a multi-wavelength system to determine a concentration of known hemoglobin species using the following matrix notation:

$$\begin{bmatrix} dA_{\lambda 1}^{LB} \\ \vdots \\ dA_{\lambda n}^{LB} \end{bmatrix} = \begin{bmatrix} \Delta l_{\lambda 1} & \cdots & 0 \\ \vdots & \ddots & \vdots \\ 0 & \cdots & \Delta l_{\lambda n} \end{bmatrix} \begin{bmatrix} \varepsilon_{\lambda 1, HbX_1} & \cdots & \varepsilon_{\lambda 1, HbX_m} \\ \vdots & \ddots & \vdots \\ \varepsilon_{\lambda n, HbX_1} & \cdots & \varepsilon_{\lambda n, HbX_m} \end{bmatrix} \cdot \begin{bmatrix} HbX_1 \\ \vdots \\ HbX_m \end{bmatrix} \cdot c(Hb),$$

wherein
$dA_\lambda^{LB}$ is a differential absorption within the Beer-Lambert model
$\varepsilon_{\lambda n1, HbX1}$ is an extinction coefficient
HbX are hemoglobin fractions
$\Delta l\lambda$ is the optical path-length for wavelength $\lambda$
c(Hb) is the hemoglobin concentration This Beer-Lambert matrix equation for determining hemoglobin concentration levels may be solved when m is equal or greater than n, e.g., which means that at least four wavelengths are needed to solve for four hemoglobin species. The spectral responses at these four wavelengths may be analyzed to determine the concentration of the plurality of hemoglobin species.

Figure 13:
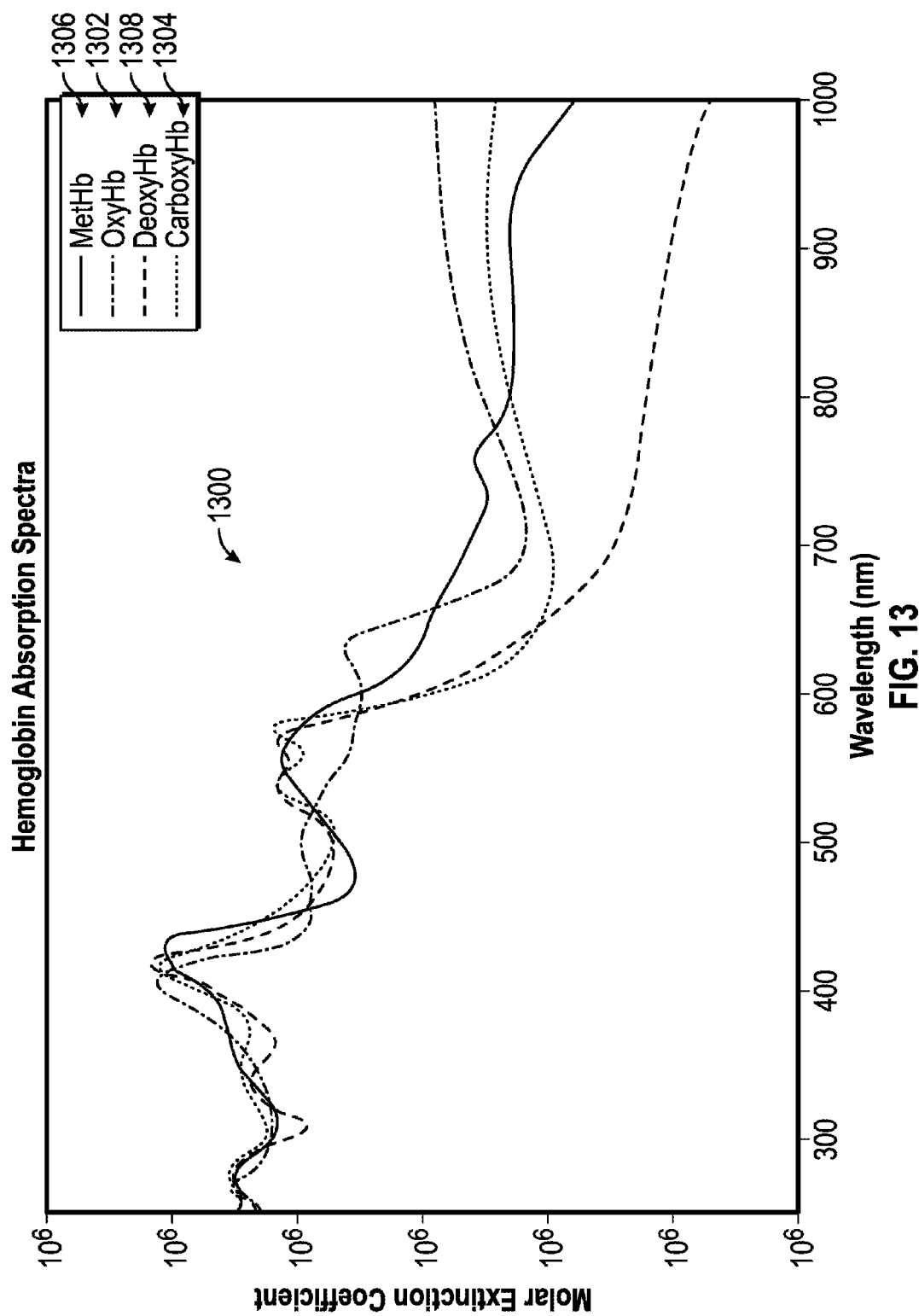
FIG. 13 illustrates a schematic block diagram of an exemplary embodiment of a graph illustrating the extinction coefficients over a range of frequencies for a plurality of hemoglobin species.

FIG. 13 illustrates a schematic block diagram of an exemplary embodiment of a graph 1300 illustrating the extinction coefficients over a range of frequencies for a plurality of hemoglobin species. The hemoglobin species include, e.g., Oxyhemoglobin [$HbO_2$ or OxyHb] 1302, Carboxyhemoglobin [HbCO or CarboxyHb] 1304, Methemoglobin [HbMet or MetHb] 1306, and deoxygenated hemoglobin (DeoxyHb or RHb) 1308. A method for determining the relative concentration or composition of hemoglobin species included in blood is described in more detail in U.S. Pat. No. 6,104,938 issued on Aug. 15, 2000, which is hereby incorporated by reference herein.

A direct calibration method for calculating hemoglobin species may be implemented by the biosensor 100. Using four wavelengths and applying a direct model for four hemoglobin species in the blood, the following equation results:

$$HbX = \frac{a_1 * dA_1 + a_2 * dA_2 + a_3 * dA_3 + a_4 * dA_4}{b_1 * dA_1 + b_2 * dA_2 + b_3 * dA_3 + b_4 * dA_4}$$

wherein
$dA_\lambda$ is the differential absorption signal
$a_n$ and $b_n$ are calibration coefficients The calibration coefficients $a_n$ and $b_n$ may be experimentally determined over a large population average. The biosensor 100 may include a calibration database to account for variances in the calibration coefficients $a_1$ and $b_1$ (or extinction coefficients) for the hemoglobin species for various underlying tissue characteristics.

A two-stage statistical calibration and measurement method for performing PPG measurement of blood analyte concentrations may also be implemented by the biosensor 100. Concentrations of MetHb, $HbO_2$, RHb and HbCO are estimated by first estimating a concentration of MetHb (in a first stage) and subsequently, if the concentration of MetHb is within a predetermined range, then the estimated concentration of MetHb is assumed to be accurate and this estimated concentration of MetHb is utilized as a "known value" in determining the concentrations of the remaining analytes $HbO_2$, RHb and HbCO (in a second stage). This method for determining a concentration of hemoglobin species using a two stage calibration and analyte measurement method is described in more detail in U.S. Pat. No. 5,891,024 issued on Apr. 6, 1999, which is hereby incorporated by reference herein.

The concentration of the hemoglobin compounds may thus be determined. The biosensor 100 compensates for the hemoglobin concentration in determinations to obtain the concentration level of NO by the biosensor 100. Though several methods are described herein for obtaining a concentration of hemoglobin analytes, other methods or processes may be used by the biosensor 100 to determine the concentration of hemoglobin analytes or otherwise adjusting or compensating the obtained measurements to account for a hemoglobin concentration when determining the concentration levels of NO in a blood stream.

Embodiment—Determination of NO Concentration Levels Using Shifts in Absorbance Peaks In another embodiment, a concentration level of NO may be obtained from measuring a characteristic shift in an absorbance peak of hemoglobin. For example, the absorbance peak for methemoglobin shifts from around 433 nm to 406 nm in the presence of NO. The advantage of the measurement of NO by monitoring methemoglobin production includes the wide availability of spectrophotometers, avoidance of sample acidification, and the relative stability of methemoglobin. Furthermore, as the reduced hemoglobin is present from the beginning of an experiment, NO synthesis can be measured continuously, removing the uncertainty as to when to sample for NO.

Figure 14:
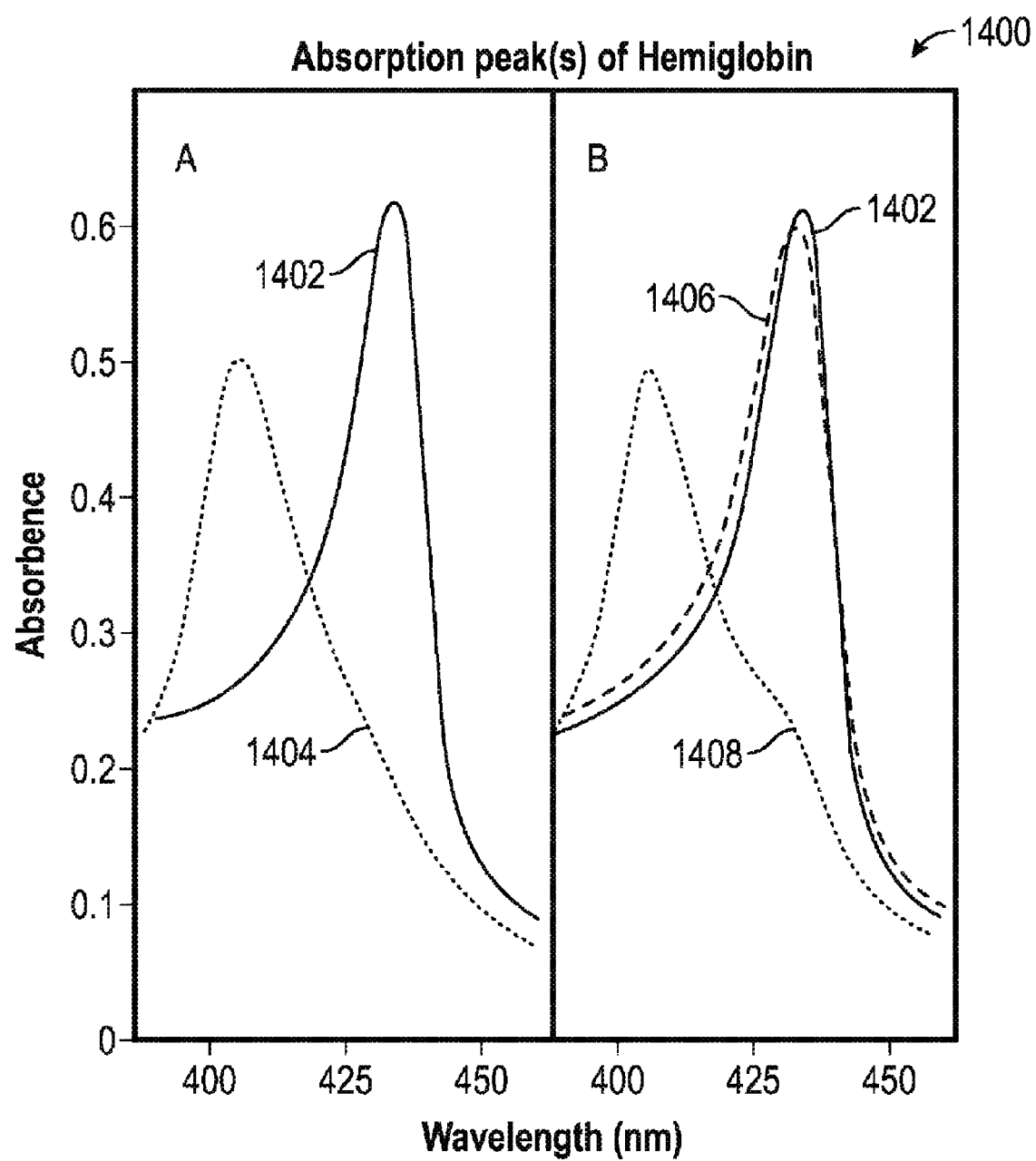
FIG. 14 illustrates a schematic block diagram of an exemplary embodiment of a graph illustrating a shift in absorbance peaks of hemoglobin in the presence of NO.

FIG. 14 illustrates a schematic block diagram of an exemplary embodiment of a graph 1400 illustrating a shift in absorbance peaks of hemoglobin in the presence of NO. In graph A, the curve 1402 illustrates the absorbance spectra of reduced hemoglobin. The addition of nitric oxide (NO) shifts the absorbance spectra curve 1402 to a lower wavelength curve 1404 due to the production of methemoglobin. In graph B, the absorbance spectra curve of reduced hemoglobin 1402 is again illustrated. Endothelial cells are then added and the absorbance spectra measured again. The curve 1406 illustrates that little change occurs in the absorbance spectra curve 1402 of reduced hemoglobin in the presence of unstimulated endothelial cells. The curve 1408 illustrates the production of methemoglobin when the same dose of endothelial cells was given after stimulation of EDRF synthesis by the ionophore.

Though the absorbance spectrums shown in the graph 1400 were measured using in vitro assays, the biosensor 100 may detect nitric oxide in vivo using PPG techniques by measuring the shift in the absorbance spectra curve of reduced hemoglobin 1402 in tissue and/or arterial blood flow. The absorbance spectra curve 1402 shifts with a peak from around 430 nm to a peak around 411 nm depending on the production of methemoglobin. The greater the degree of the shift of the peak of the curve 1402, the higher the production of methemoglobin and NO concentration level. Correlations may be determined between the degree of the measured shift in the absorbance spectra curve 1402 of reduced hemoglobin to an NO concentration level. The correlations may be determined from a large sample population or for a particular patient and stored in a calibration database. The biosensor 100 may thus obtain an NO concentration level by measuring the shift of the absorbance spectra curve 1402 of reduced hemoglobin.

Figure 15:
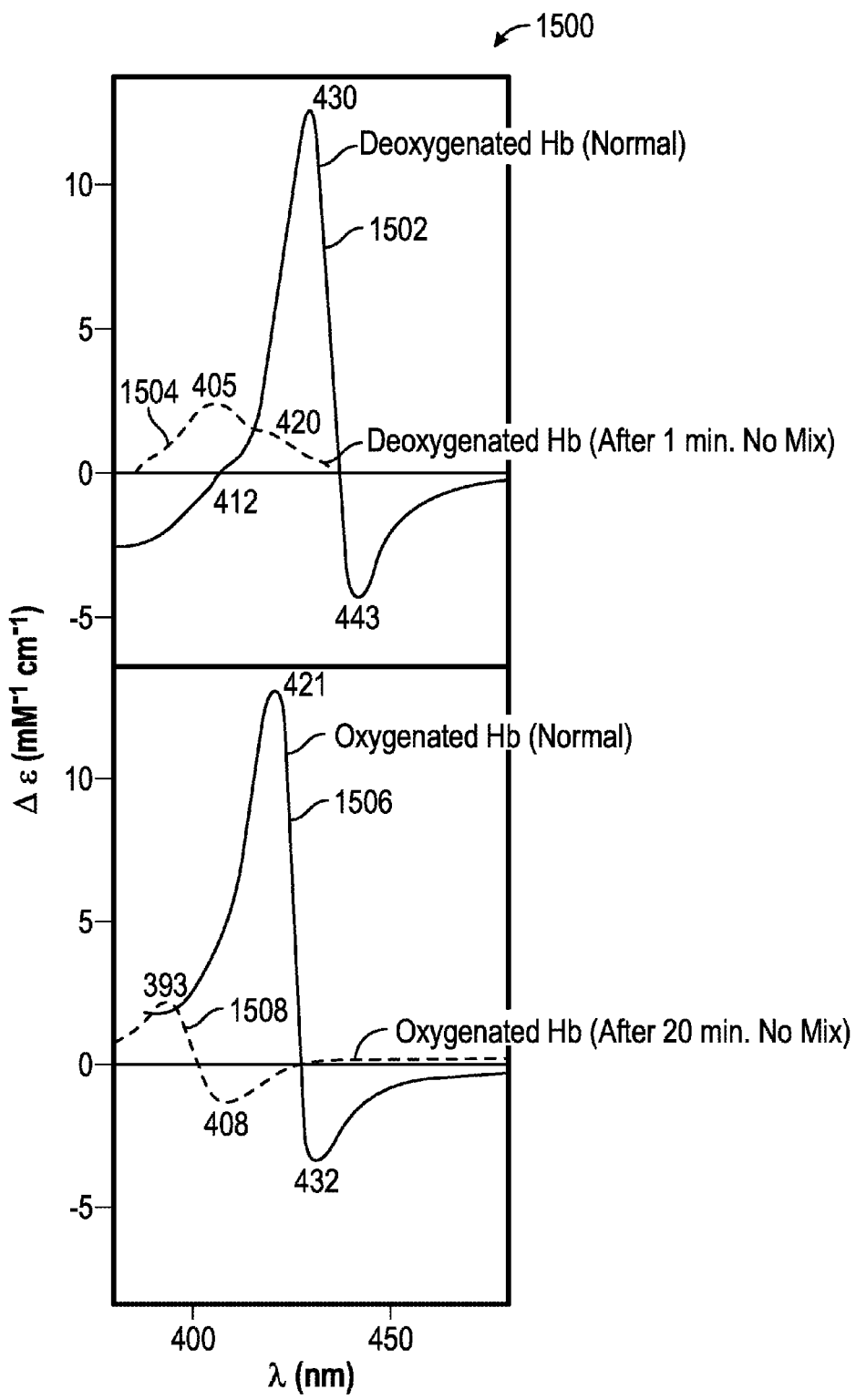
FIG. 15 illustrates a schematic block diagram of an exemplary embodiment of a graph illustrating a shift in absorbance peaks of oxygenated and deoxygenated hemoglobin (HB) in the presence of nitric oxide NO.

FIG. 15 illustrates a schematic block diagram of an exemplary embodiment of a graph 1500 illustrating a shift in absorbance peaks of oxygenated and deoxygenated hemoglobin (HB) in the presence of nitric oxide NO. The absorbance spectra curve 1502 of deoxygenated HB has a peak of around 430 nm. After a one minute time period of exposure to a nitric oxide mixture, the absorbance spectra curve 1504 of deoxygenated HB shifted to a peak of around 405 nm. In addition, the absorbance spectra curve 1506 of oxygenated HB has a peak around 421 nm. After a twenty minute time period of exposure to a nitric oxide mixture, the absorbance spectra curve 1508 of oxygenated HB shifted to a peak of around 393 nm. The Deoxygenated Hb has an absorption peak at 430 nm (curve 1502) and in the presence of NO has a peak shift to 405 nm (curve 1504). The Oxygenated Hb has absorption peak at 421 nm (curve 1506) in presence of NO has peak shift to 393 nm (curve 1508).

Though the absorbance spectrums shown in the graph 1500 were measured using in vitro assays, the biosensor 100 may obtain an NO concentration level by measuring the shift of the absorbance spectra curve 1502 of deoxygenated hemoglobin and/or by measuring the shift of the absorbance spectra curve 1506 of oxygenated hemoglobin in vivo. The biosensor 100 may then access a calibration database that correlates the measured shift in the absorbance spectra curve 1502 of deoxygenated hemoglobin to an NO concentration level. Similarly, the biosensor may access a calibration database that correlates the measured shift in the absorbance spectra curve 1506 of oxygenated hemoglobin to an NO concentration level.

Figure 16:
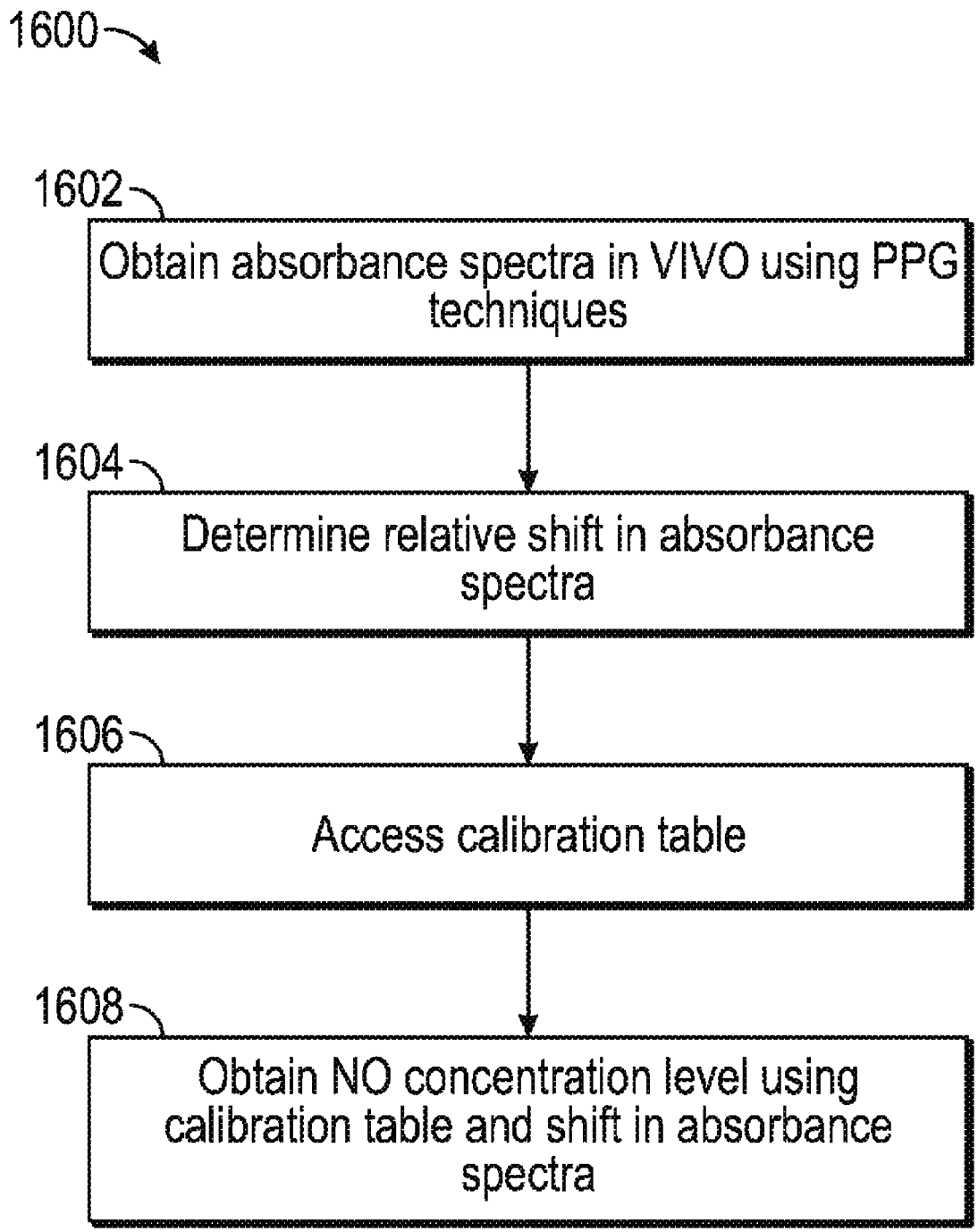
FIG. 16 illustrates a logical flow diagram of an exemplary embodiment of a method for measuring NO concentration levels in vivo using shifts in absorbance spectra.

FIG. 16 illustrates a logical flow diagram of an exemplary embodiment of a method 1600 for measuring NO concentration levels in vivo using shifts in absorbance spectra. The biosensor 100 may obtain a concentration of NO by measuring shifts in absorbance spectra of one or more substances that interact with NO. For example, the one or more substances may include oxygenated and deoxygenated hemoglobin (HB). The PPG circuit 110 detects a spectral response at a plurality of wavelengths of the one or more substances that interact with NO at 1602. The biosensor 100 determines the relative shift in the absorbance spectra for the substance at 1604. For example, the biosensor 100 may measure the absorbance spectra curve 1502 of deoxygenated HB and determine its relative shift or peak between the range of approximately 430 nm and 405 nm. In another example, the biosensor 100 may measure the absorbance spectra curve of oxygenated HB and determine its relative shift or peak between 421 nm and 393 nm.

The biosensor 100 accesses a calibration database that correlates the relative shift in the absorbance spectra of the substance with a concentration level of NO at 1606. The biosensor 100 may thus obtain an NO concentration level using calibration database and the measured relative shift in absorbance spectra of the spectrum at 1608.

Figure 17:
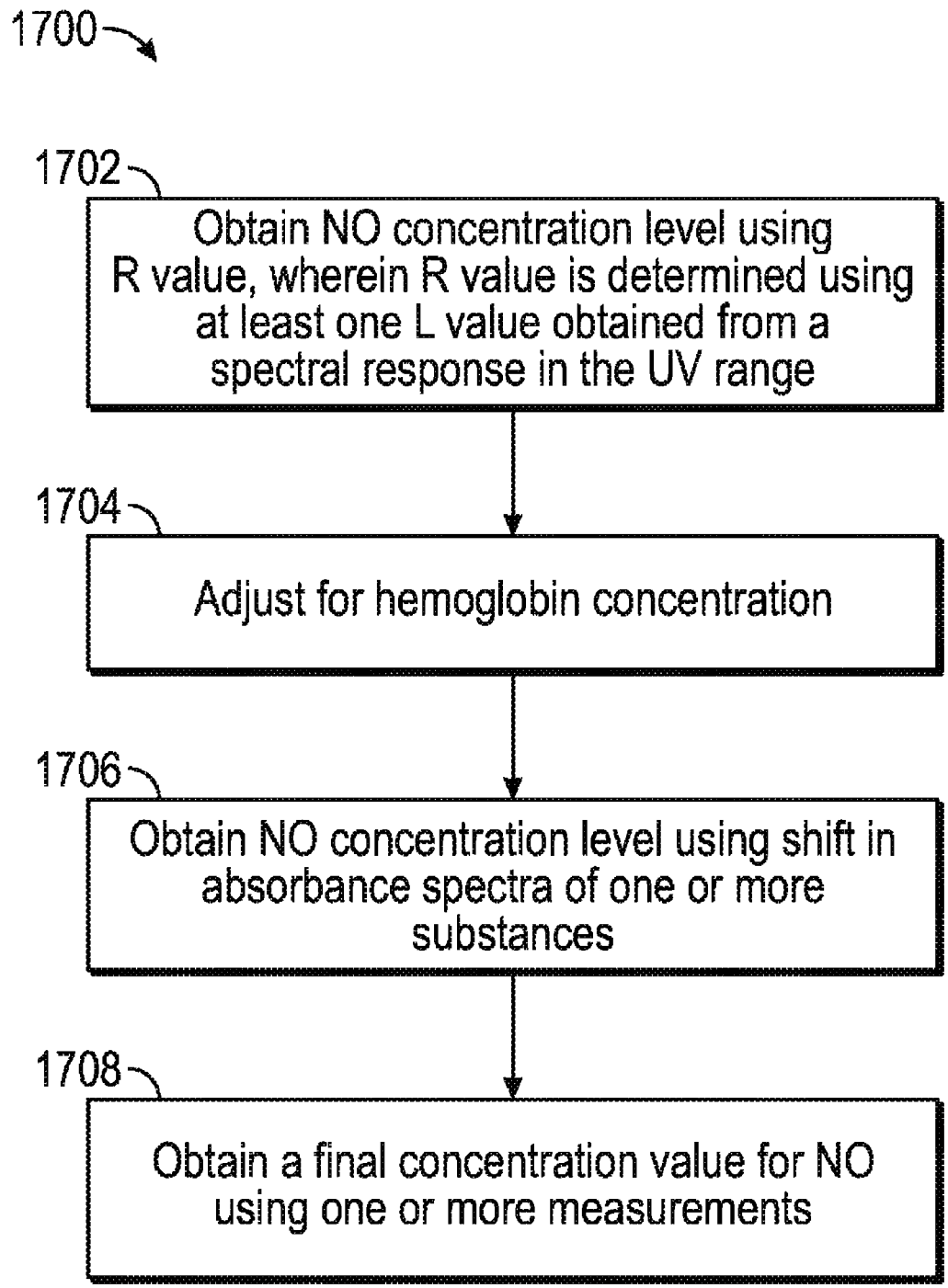
FIG. 17 illustrates a logical flow diagram of an exemplary embodiment of a method for measuring NO concentration levels using one or more measurement techniques.

FIG. 17 illustrates a logical flow diagram of an exemplary embodiment of a method 1700 for measuring NO concentration levels using one or more measurement techniques. In an embodiment, the biosensor 100 is configured to determine a concentration level of NO in vivo using PPG technology and one or more measurement techniques described herein. For example, the biosensor 100 may determine an R value using at least one L value obtained from a spectral response in the UV range at 1702. For example, the R value may be obtained using, e.g. an L Value in the range from 380-410 such as 390 nm or 395 nm. at $L_{390}/L_{940}$, at 1702 and accessing a calibration database that maps the R value to an NO concentration level. In another example, the biosensor may determine NO concentration level using absorption spectrum over a plurality of wavelengths and adjusting or compensating for hemoglobin concentrations at 1704. In another example, the biosensor 100 may determine the relative shift in the absorbance spectra for a substance (such as hemoglobin) and access a calibration database that correlates the relative shift in the absorbance spectra of the substance with a concentration level of NO at 1706.

The biosensor 100 may use a plurality of these methods to determine a plurality of values for the concentration level of NO at 1708. The biosensor 100 may determine a final concentration value using the plurality of values. For example, the biosensor 100 may average the values, obtain a mean of the values, etc.

Figure 18:
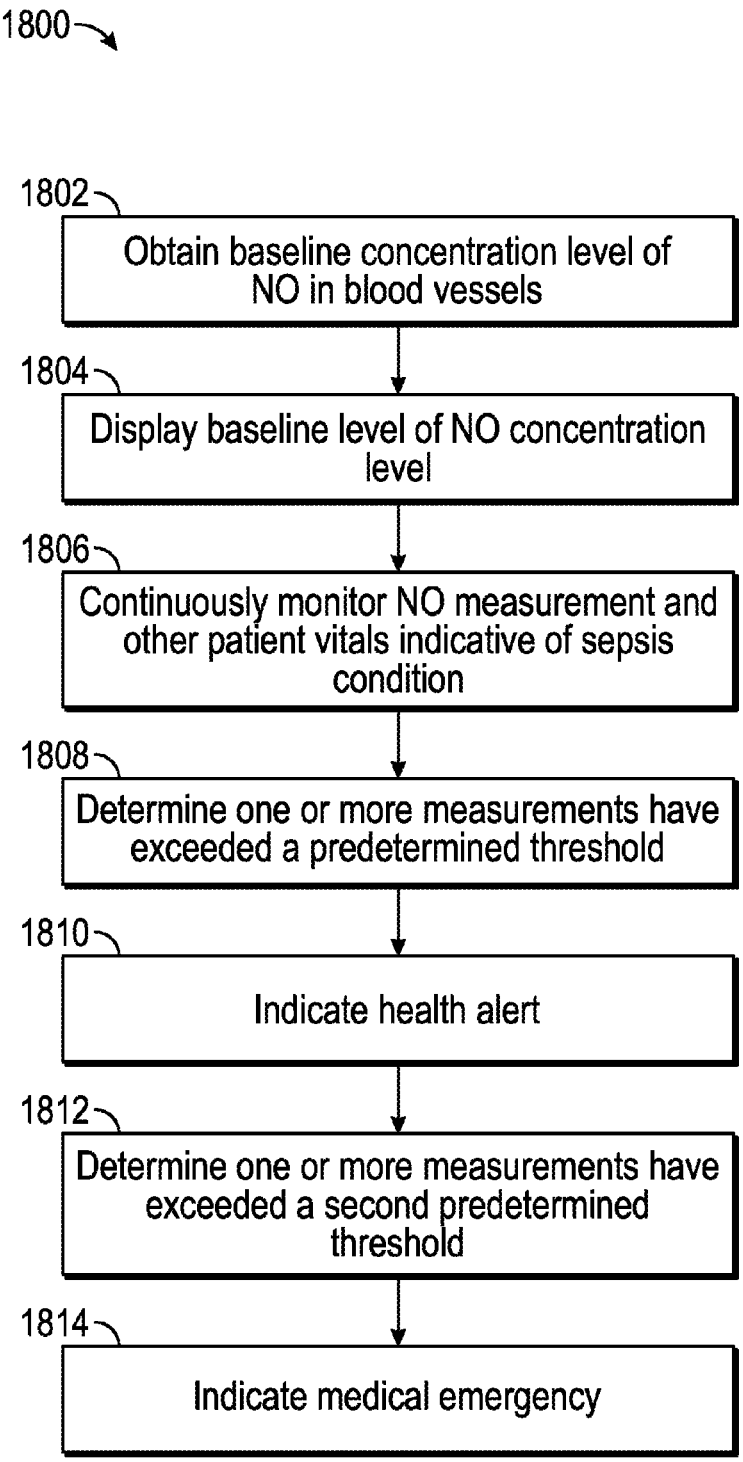
FIG. 18 illustrates illustrates a logical flow diagram of an embodiment of a method 1800 for providing a health alert for sepsis by monitoring NO measurements.

FIG. 18 illustrates a logical flow diagram of an embodiment of a method 1800 for providing a health alert for sepsis by monitoring NO measurements. In 1802, a baseline of an NO concentration level in blood vessels is obtained. For example, the NO concentration level may be obtained from an R value using $L_{\lambda 1}$=390 nm and $L_{\lambda 2}$=940 nm or an R value at $L_{\lambda 1}$=395 nm and $L_{\lambda 2}$=660 nm. In another embodiment, the NO measurement may be obtained using a value of $L_{\lambda 1}$=380 nm-400 nm and $L_{\lambda 2} \geq$660 nm. The spectral response used to determine the value of $L_{\lambda 1}$=380 nm-400 nm may also be measuring other NO compounds or isoforms such as eNOS or iNOS or nNOS or other compounds bonded to a plurality of hemoglobin species. The concentration of the plurality of hemoglobin species may be adjusted from the NO measurements and a calibration database used to obtain an NO concentration level. In another example, the biosensor 100 may determine the relative shift in the absorbance spectra for a substance (such as hemoglobin) and access a calibration database that correlates the relative shift in the absorbance spectra of the substance with a concentration level of NO.

In 1804, the biosensor 100 displays the baseline NO measurement and then non-invasively and continuously monitors the NO measurement in blood vessels at 1806. For example, the biosensor 100 may obtain the NO measurement at least once per minute or more frequently, such as every 10 seconds or 30 seconds, and continues to display the NO measurement. The biosensor 100 may also monitor other patient vitals indicative of sepsis condition, such as temperature, pulse, and respiration rate.

The NO measurement of the nitric oxide is compared to a first predetermined threshold. For example, normal ranges of the NO measurement from the baseline measurement are determined for septic risk. Patient vitals may also be compared to predetermined thresholds Depending on the comparison, one or more warnings are displayed. For example, the first predetermined threshold may be when the NO measurement has exceeded at least 10% of the baseline level of the NO measurement. A warning is displayed to indicate a health alert at 1810. A caregiver may then perform other tests to determine the cause of the elevated NO measurement, such as lactic acid blood test for sepsis.

The biosensor continues to monitor the NO measurement in blood vessels and compare the NO measurement to one or more predetermined thresholds. In 1812, it is determined that the NO measurement has exceeded a second predetermined threshold. For example, the NO measurement equals or exceeds at least 30% of a baseline level of the NO measurement. A warning to indicate a medical emergency is displayed at 1814. Due to the immediate danger of such high levels of NO measurement and dangers of septic shock, a request for immediate emergency treatment may be indicated. Though 10% and 30% are illustrated in this example, other percentages over the baseline level may also trigger warnings or alerts.

TABLE 1

| SpNO % Interpretation (Nitric Oxide Levels) | |
| --- | --- |
| 0-1.5% | Diabetic patients |
| 1.5-2% | Pre-Diabetic |
| 2-8% | Normal Patient |

TABLE 1-continued

| SpNO % Interpretation (Nitric Oxide Levels) | |
| --- | --- |
| >10% | Clinically significant, consult medical control for direction |
| >30% | Assess for septic shock, provide high flow O2, and transport Consider emergency treatment |

Embodiment—Adjustments in Response to Positioning of the Biosensor

Figure 19:
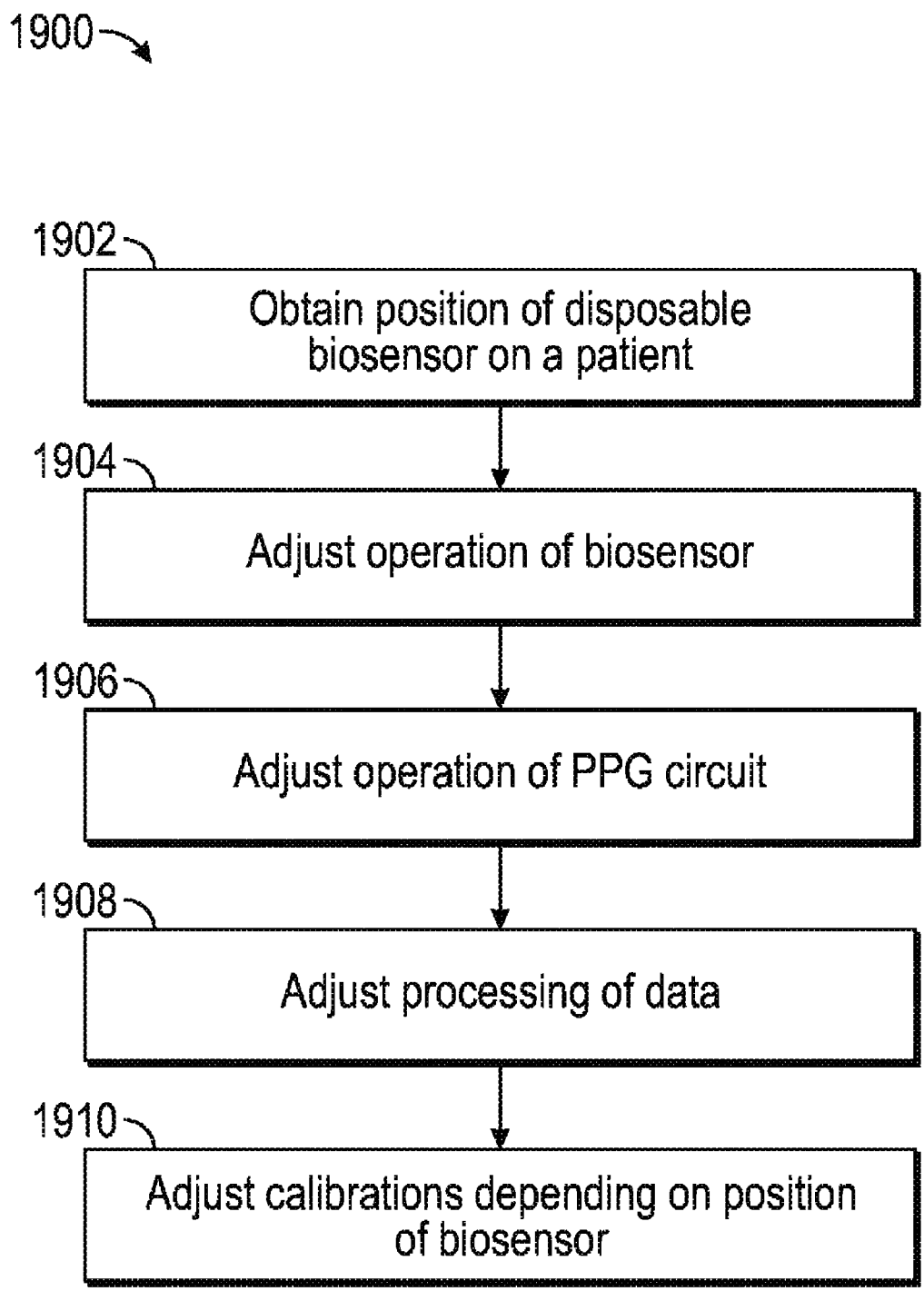
FIG. 19 illustrates a logical flow diagram of an embodiment of a method for adjusting operation of the biosensor in response to a position of the biosensor.

FIG. 19 illustrates a logical flow diagram of an embodiment of a method 1900 for adjusting operation of the biosensor 100 in response to a position of the biosensor 100. When the biosensor 100 is implemented in the patch 102 form factor, the biosensor 100 may be positioned over different areas of a patient. The skin tissue exhibits different underlying characteristics depending on the area of the body.

For example, the biosensor 100 may be positioned on or attached to, e.g. a hand, a wrist, an arm, forehead, chest, abdominal area, ear lobe, fingertip or other area of the skin or body or living tissue. The characteristics of underlying tissue vary depending on the area of the body, e.g. the underlying tissue of an abdominal area has different characteristics than the underlying tissue at a wrist. The operation of the biosensor 100 may need to be adjusted in response to its positioning due to such varying characteristics of the underlying tissue.

The biosensor 100 is configured to obtain position information on a patient at 1902. The position information may be input from a user interface. In another aspect, the biosensor 100 may determine its own positioning. For example, the PPG circuit 110 may be configured to detect characteristics of underlying tissue. The biosensor 100 then correlates the detected characteristics of the underlying tissue with known or predetermined characteristics of underlying tissue (e.g. measured from an abdominal area, wrist, forearm, leg, forehead, etc.) to determine its positioning. Information of amount and types of movement from an activity monitoring circuit implemented within the biosensor 100 may also be used in the determination of position.

In response to the determined position and/or detected characteristics of the underlying tissue, the operation of the biosensor 100 is adjusted at 1904. For example, the biosensor 100 may adjust operation of the PPG circuit 110 at 1906. The article, "Optical Properties of Biological Tissues: A Review," by Steven L. Jacques, Phys. Med. Biol. 58 (2013), which is hereby incorporated by reference herein, describes wavelength-dependent behavior of scattering and absorption of different tissues. The PPG circuit 110 may adjust a power of the LEDs or a frequency or wavelength of the LEDs based on the underlying tissue. The biosensor 100 may adjust processing of the data at 1908. For example, an absorption coefficient may be adjusted when determining a concentration level of a substance based on Beer-Lambert principles due to the characteristics of the underlying tissue.

In addition, the calibrations utilized by the biosensor 100 may vary depending on the positioning of the biosensor at 1908. For example, the calibration database may include different table or other correlations between R values and NO concentration level depending on position of the biosensor. Due to the different density of tissue and vessels, the R value obtained from measurements over an abdominal area may be different than measurements over a wrist or forehead. The calibration database may thus include different correlations of the R value and NO concentration level depending on the underlying tissue. Other adjustments may also be implemented by the biosensor 100 depending on predetermined or measured characteristics of the underlying tissue.

The biosensor 100 is thus configured to obtain position information and perform adjustments to its operation in response to the position information.

Embodiment—Clinical Data

Clinical data obtained using an embodiment of the biosensor 100 is now described herein. The biosensor 100 was used to monitor concentration levels or indicators of Nitric Oxide in the blood flow of a patient in clinical trials over a measurement time period.

Figure 20:
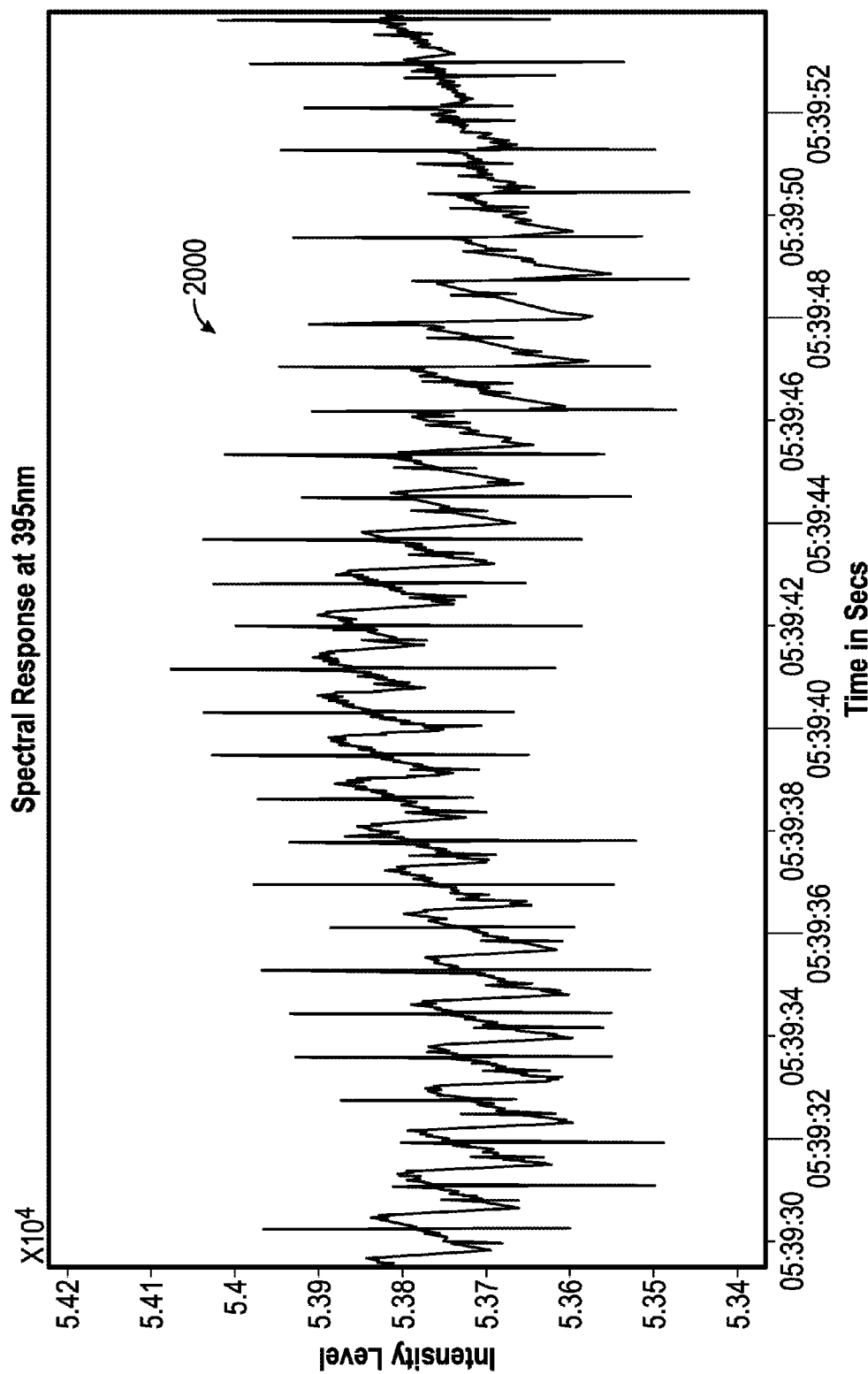
FIG. 20 illustrates a schematic drawing of an exemplary embodiment of results of a spectral response obtained using an embodiment of the biosensor from a patient.

FIG. 20 illustrates a schematic drawing of an exemplary embodiment of results of a spectral response 2000 obtained using an embodiment of the biosensor 100 from a patient. The spectral response 2000 was obtained at a wavelength of around 395 nm and is illustrated for a time period of about 40 seconds.

Figure 21:
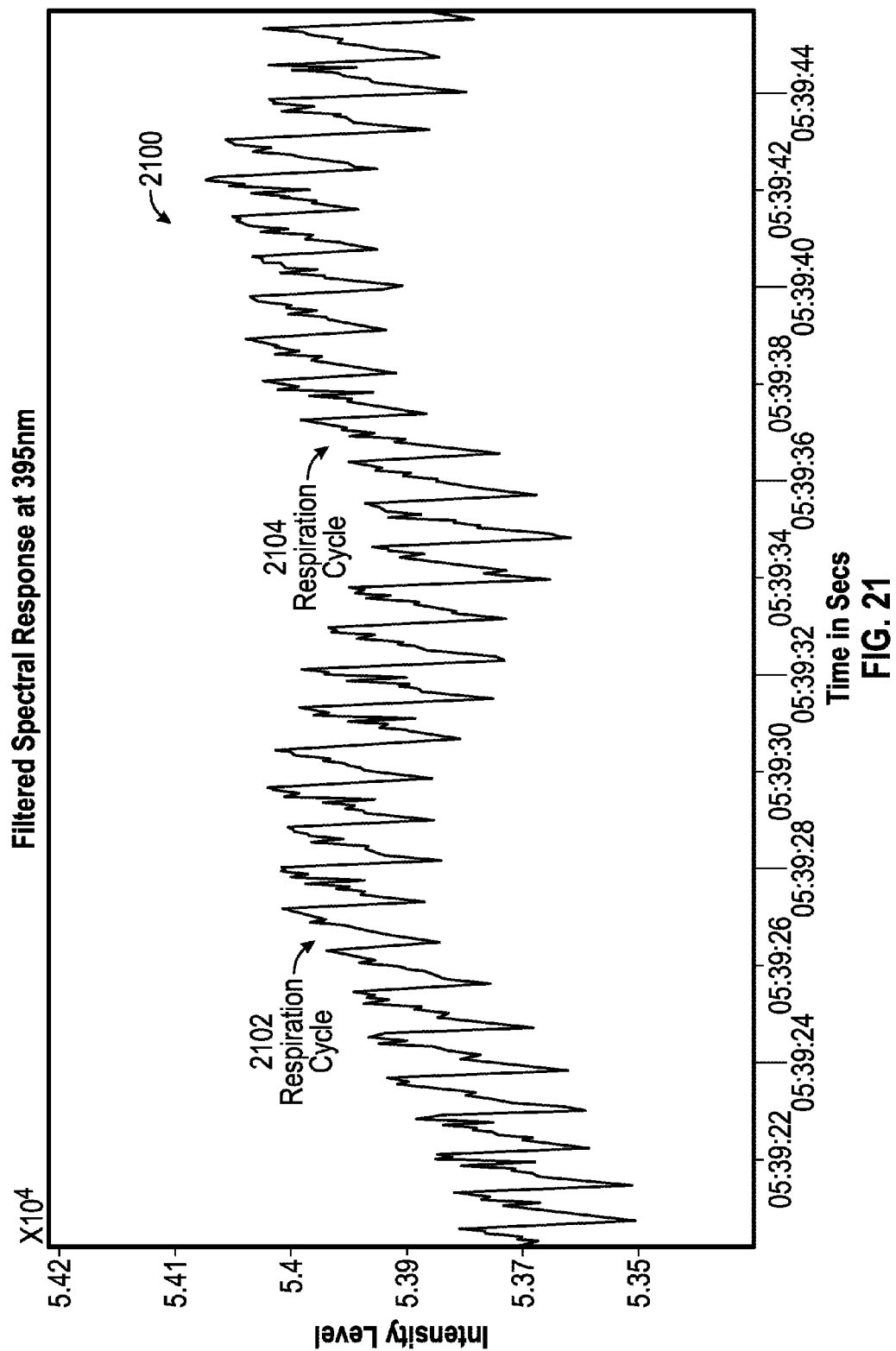
FIG. 21 illustrates a schematic drawing of an exemplary embodiment of results of a filtered spectral response.

FIG. 21 illustrates a schematic drawing of an exemplary embodiment of results of a filtered spectral response 2100. The spectral response 2000 in FIG. 20 is filtered by the biosensor 100 using digital signal processing techniques to eliminate noise and background interference to obtain the filtered spectral response 2100. A first respiration cycle 2102 and a second respiration cycle 2104 may be seen in the slow fluctuation of the filtered spectral response 2100. Due to this fluctuation over respiratory cycles, the obtained L values are averaged over a plurality of respiratory cycles or over a predetermined time period such as 1-2 minutes. In addition, the respiration rate of the patient may be obtained from the respiration cycles.

Figure 22:
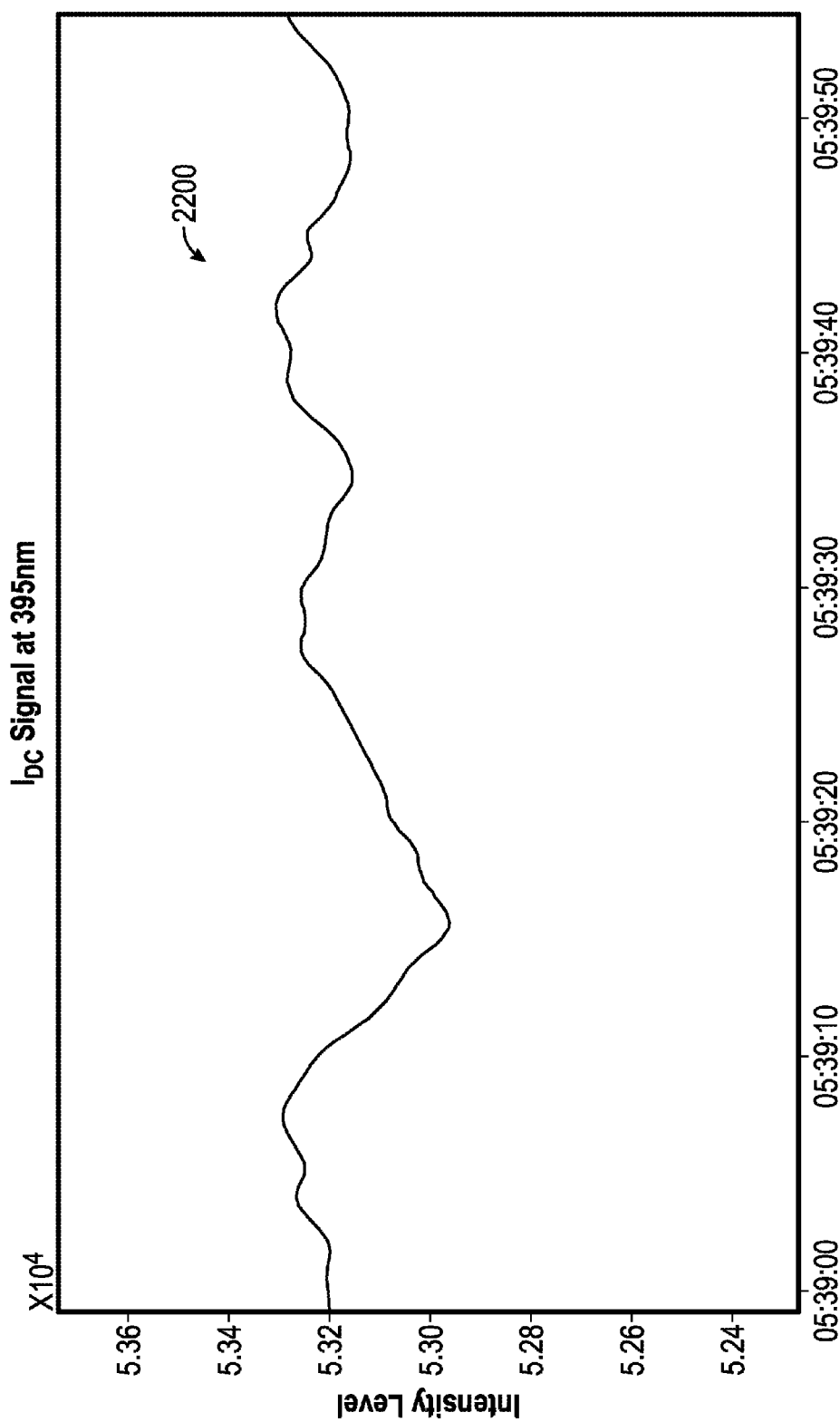
FIG. 22 illustrates a schematic drawing of an exemplary embodiment of results of an $I_{DC}$ signal generated using the filtered spectral response.

FIG. 22 illustrates a schematic drawing of an exemplary embodiment of results of an $I_{DC}$ signal 2200 generated using the filtered spectral response 2100. A low pass filter (such as a 5 Hz low pass filter) is applied to the filtered spectral response 2100 ($I_{AC+DC}$) to obtain the DC component of the spectral response $I_{DC}$. Rather than using a low pass filter, fast Fourier transform or other functions may also be used to isolate the DC component of the filtered spectral response 2100.

Figure 23:
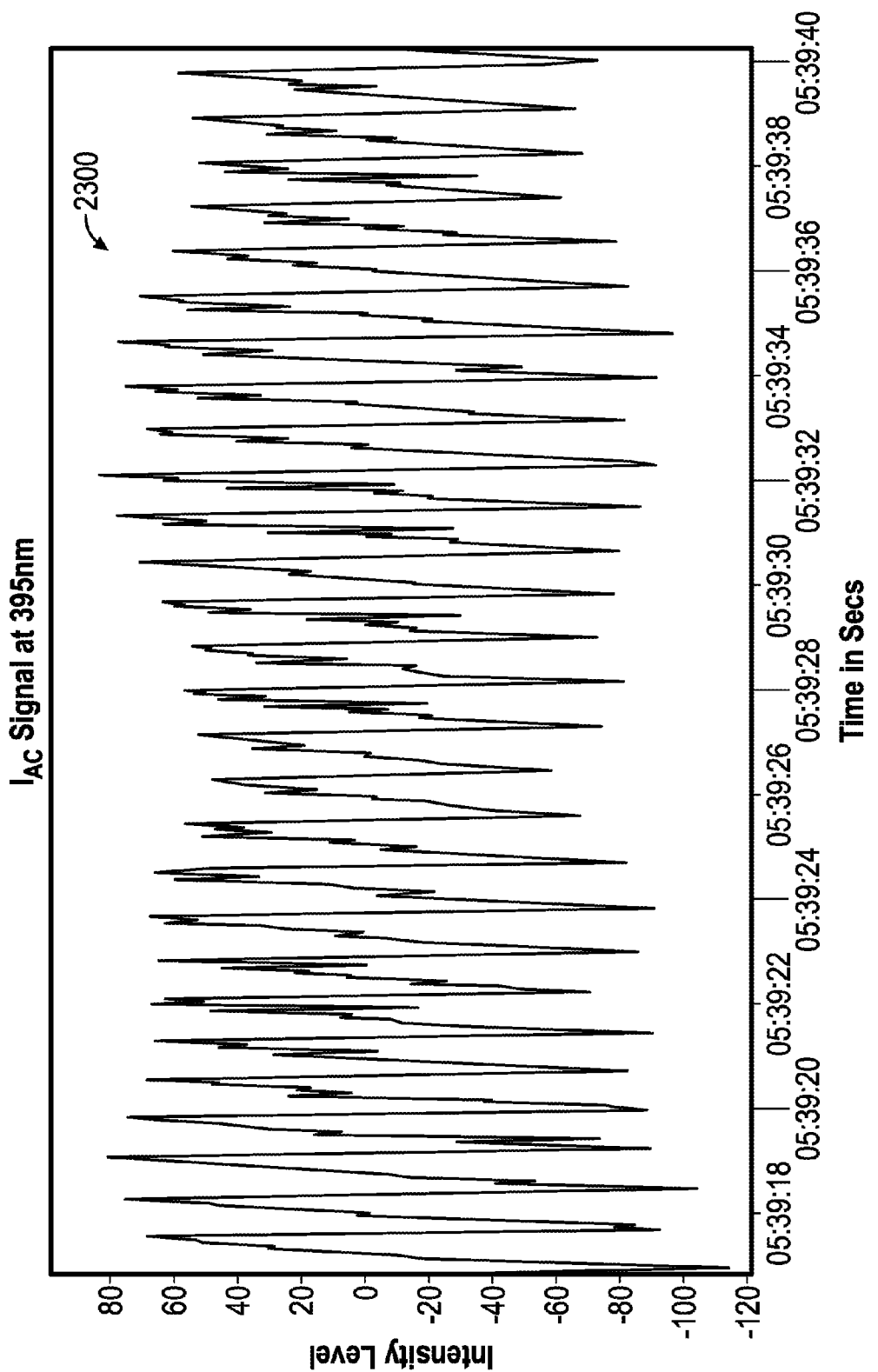
FIG. 23 illustrates a schematic drawing of an exemplary embodiment of results of an $I_{AC}$ signal.

FIG. 23 illustrates a schematic drawing of an exemplary embodiment of results of an $I_{AC}$ signal 2300. The $I_{AC}$ signal 2300 is generated from the the filtered spectral response 2300 and the signal $I_{DC}$ 2200. The AC component is the fluctuation due to the pulsatile expansion and contraction of the arteriolar bed as the volume of arterial blood increases and decreases due to the pulse rate. In order to measure the AC fluctuation, measurements are taken at different times and a peak detection algorithm is used to determine the diastolic point and the systolic point of the filtered spectral response. Rather than using a low pass filter, fast Fourier transform or other functions may also be used to isolate the DC component of the filtered spectral response to obtain $I_{AC}$. A pulse rate may also be obtained from the $I_{AC}$ signal 2300.

Figure 24:
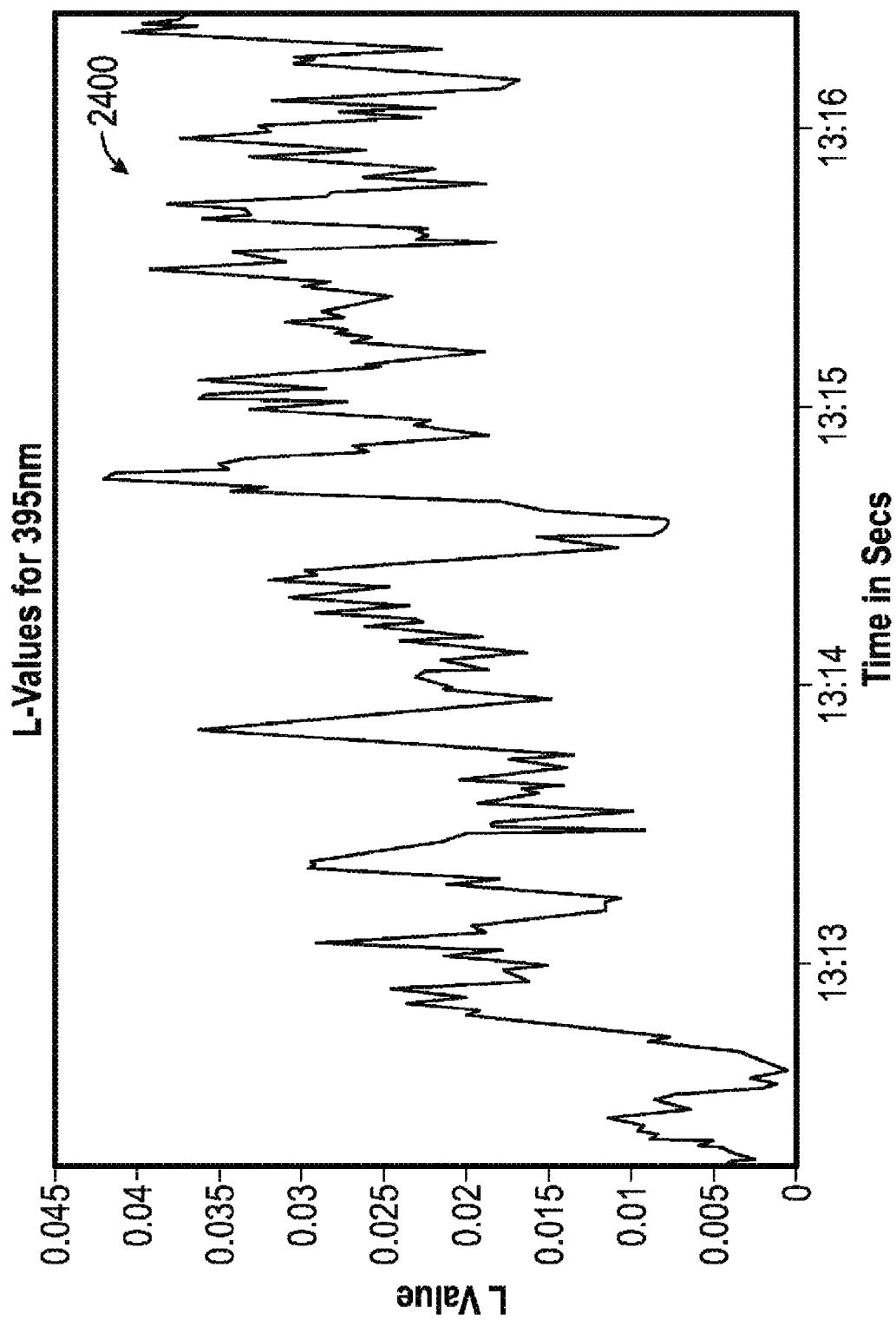
FIG. 24 illustrates a schematic drawing of an exemplary embodiment of results of L values obtained over a time period.

FIG. 24 illustrates a schematic drawing of an exemplary embodiment of results of L values 2400 obtained over a time period. In this embodiment, the L values are obtained using spectral response from an LED at 395 nm in the UV range. Other wavelengths may be implemented in a UV range, such as from 380-410 nm. This range of wavelengths has a high absorption coefficient for NO compounds. The filtered spectral response $I_{AC+DC}$ 2100 and $I_{DC}$ signal 2200 components are used to compute L values 2400. A logarithmic function is applied to the ratio of the signal $I_{AC+DC}$ and the signal $I_{DC}$:

$$L = \mathrm{Log10}\left(\frac{IAC + DC}{IDC}\right)$$

The L values 2400 fluctuate between 0.005 and 0.045 over the four second time period illustrated in the graph.

Figure 25:
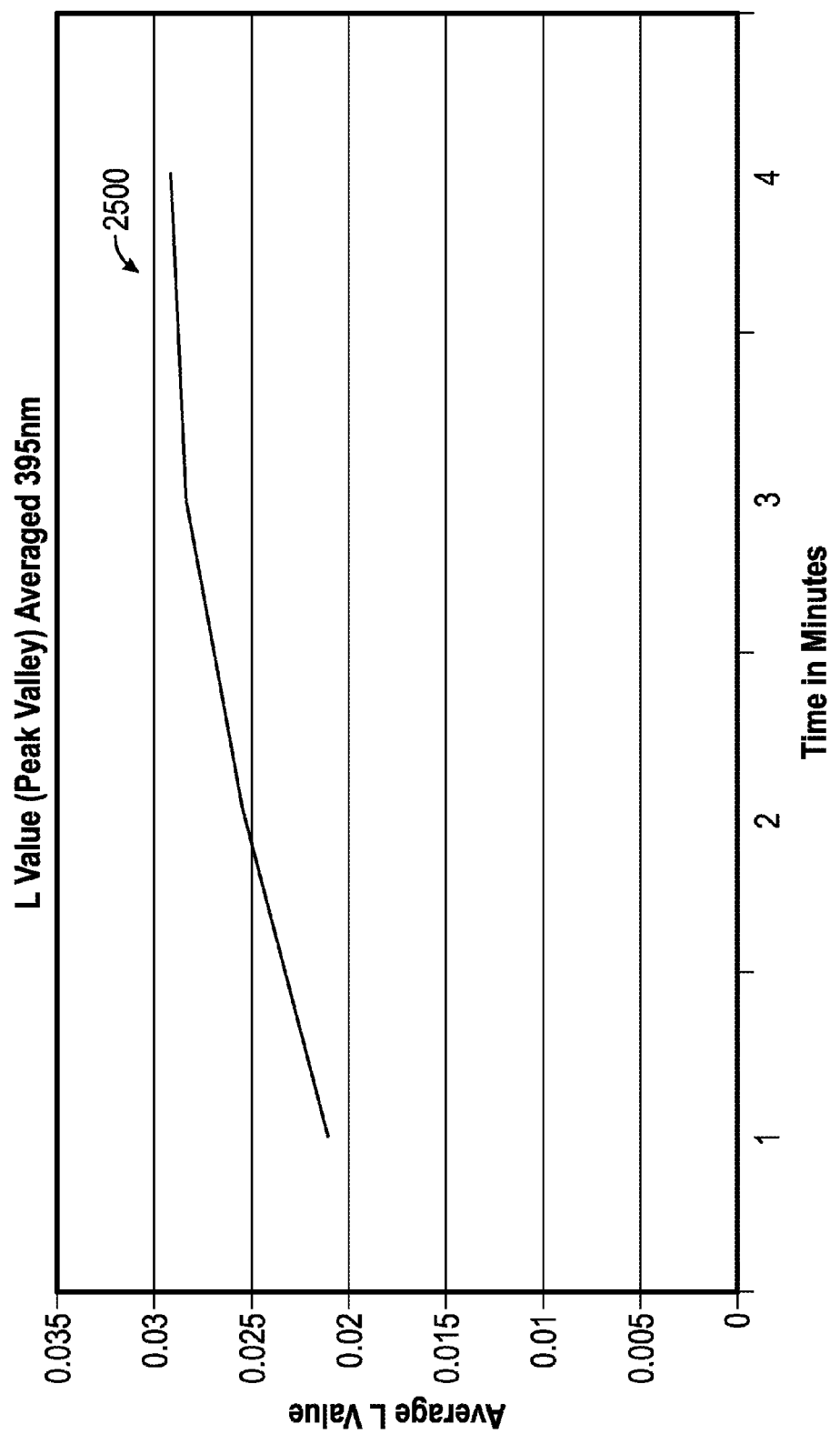
FIG. 25 illustrates a schematic drawing of an exemplary embodiment of results of averaged L values.

FIG. 25 illustrates a schematic drawing of an exemplary embodiment of results of averaged L values 2500. The L values are affected by the respiratory cycle as previously described. Thus, the L values 2400 shown in FIG. 24 are averaged over two or more respiratory cycles. Alternatively, the L values 2400 may be averaged over a predetermined time period (such as a 1-2 minute time period). As shown in FIG. 25, the averaged L values 2500 fluctuate between 0.2 and 0.3 over a three minute time period.

The averaged L values may be used as an NO measurement for baseline measurements of NO or to provide alerts based on NO measurements as well. For example, when the averaged $L_{395}$ exceeds 10% of the baseline value, e.g. such as exceeds 0.3 by over 10%, then an alert may be provided by the biosensor 100. When the averaged $L_{395}$ exceed 30% of the baseline value, e.g. such as exceeds 0.3 by 30% or more, then another alert of a medical emergency may be provided by the biosensor 100. Alternatively, the baseline value of the averaged L value for an individual may be based on observations of a healthy general population over a period of hours or days.

Figure 26:
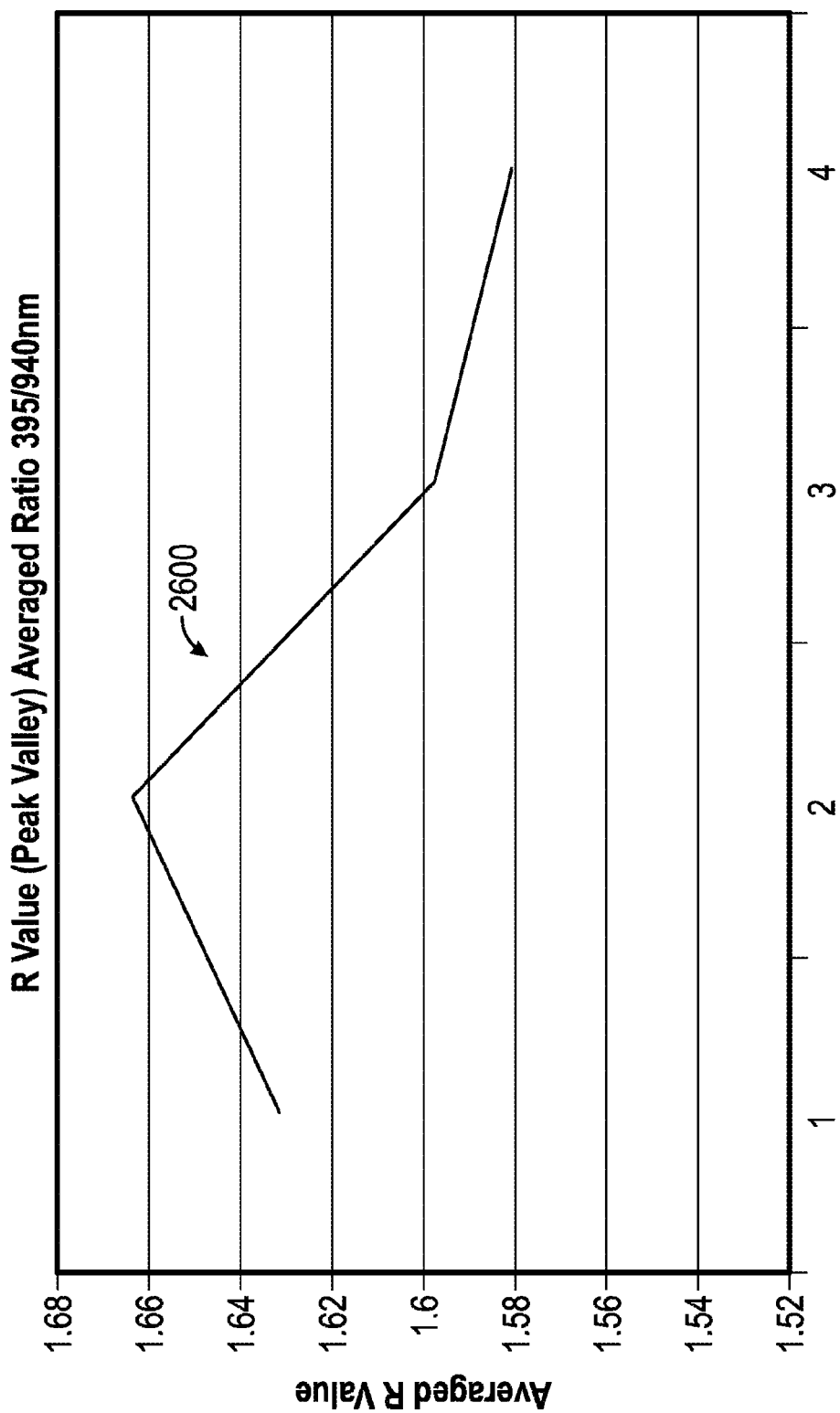
FIG. 26 illustrates a schematic drawing of an exemplary embodiment of results of averaged R values.

FIG. 26 illustrates a schematic drawing of an exemplary embodiment of results of averaged R values 2600. In this embodiment, the R value is a ratio of the averaged $L_{395\ nm}$ values 2400 and $L_{940\ nm}$ values:

$$\mathrm{Ratio}\ R = \frac{L395}{L940}$$

The averaged R values 2600 may be obtained from averaging the Ratio R over a predetermined time period or may be calculated from the averaged L values. As shown in FIG. 26, the averaged R values 2600 fluctuate between 1.68 and 1.58 over a three minute time period.

The averaged R values may be used as an NO measurement for baseline measurements of NO or to provide alerts based on NO measurements as well. For example, when the averaged R value exceeds 10% of the baseline value, e.g. such as exceeds 1.68 by over 10%, then an alert may be provided by the biosensor 100. When the averaged R value exceed 30% of the baseline value, e.g. such as exceeds 1.68 by 30% or more, then another alert of a medical emergency may be provided by the biosensor 100. Alternatively, the baseline value of the averaged R value for an individual may be based on observations of a healthy general population over a period of hours or days.

Figure 27:
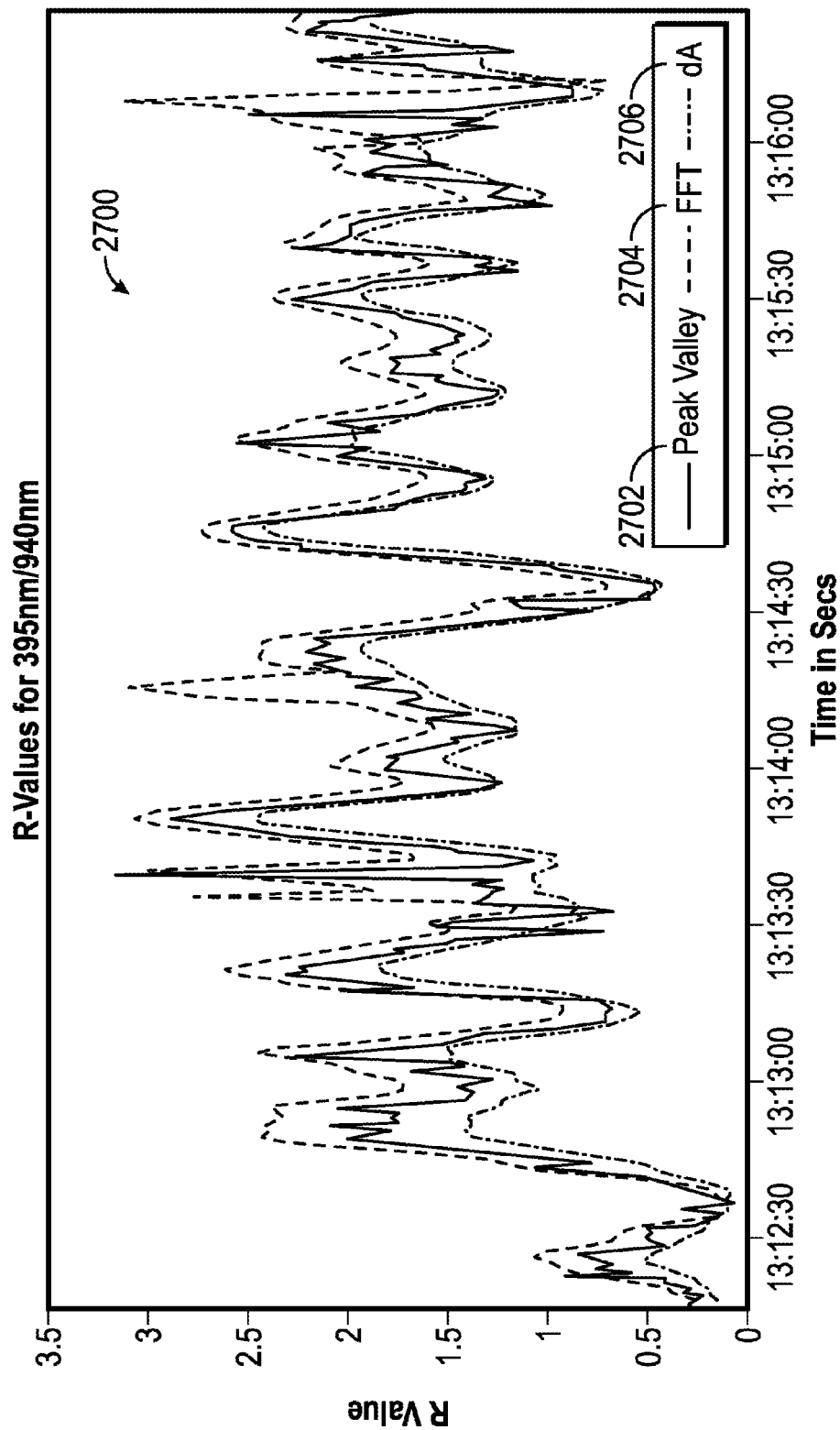
FIG. 27 illustrates a schematic drawing of an exemplary embodiment of results of R values determined using a plurality of methods.

FIG. 27 illustrates a schematic drawing of an exemplary embodiment of results of R values 2700 determined using a plurality of methods. The R values 2700 corresponding to the wavelengths of 395 nm/940 nm is determined using three methods. The R Peak Valley curve 2702 is determined using the Ratio $$R = \frac{L395}{L940}$$

as described hereinabove. The R FFT curve 2704 is determined using FFT techniques. The R differential absorption curve 2708 is determined using the shift in absorbance spectra as described hereinabove with respect to FIGS. 14-16. As seen in FIG. 27, the determination of the R values using the three methods provides similar results, especially when averaged over a period of time. A mean or average of the R values 2702, 2704 and 2708 may be calculated to obtain a final R value or one of the methods may be preferred depending on the positioning of the biosensor or underlying tissue characteristics.

Figure 28:
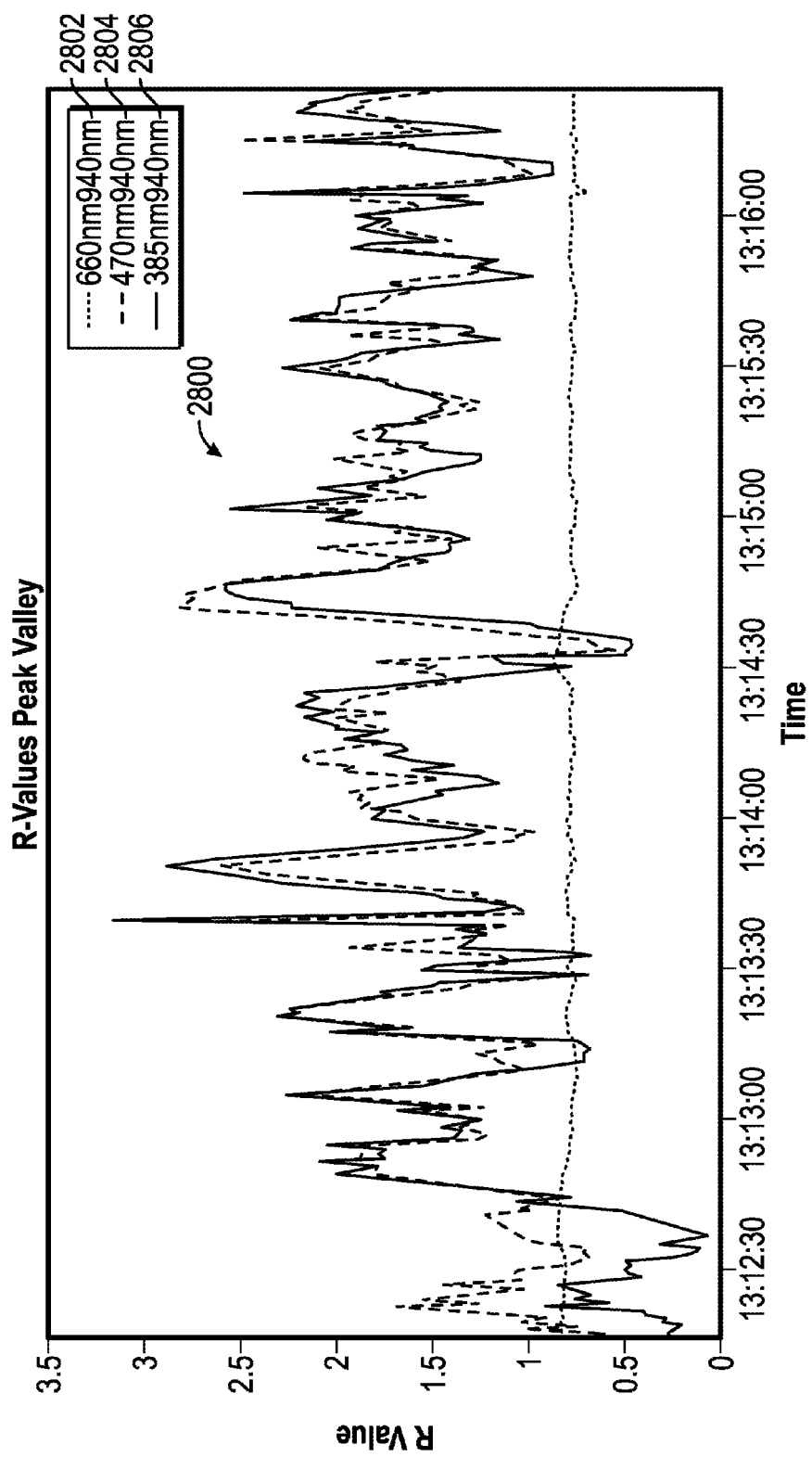
FIG. 28 illustrates a schematic drawing of an exemplary embodiment of results of R values for a plurality of wavelength ratios.

FIG. 28 illustrates a schematic drawing of an exemplary embodiment of results of R values 2800 for a plurality of wavelength ratios. The R values for 395 nm/940 nm 2806, the R values for 470 nm/940 nm 2804 and the R values for 660 nm/940 nm 2806 are shown over a time period of about 4 seconds.

Figure 29:
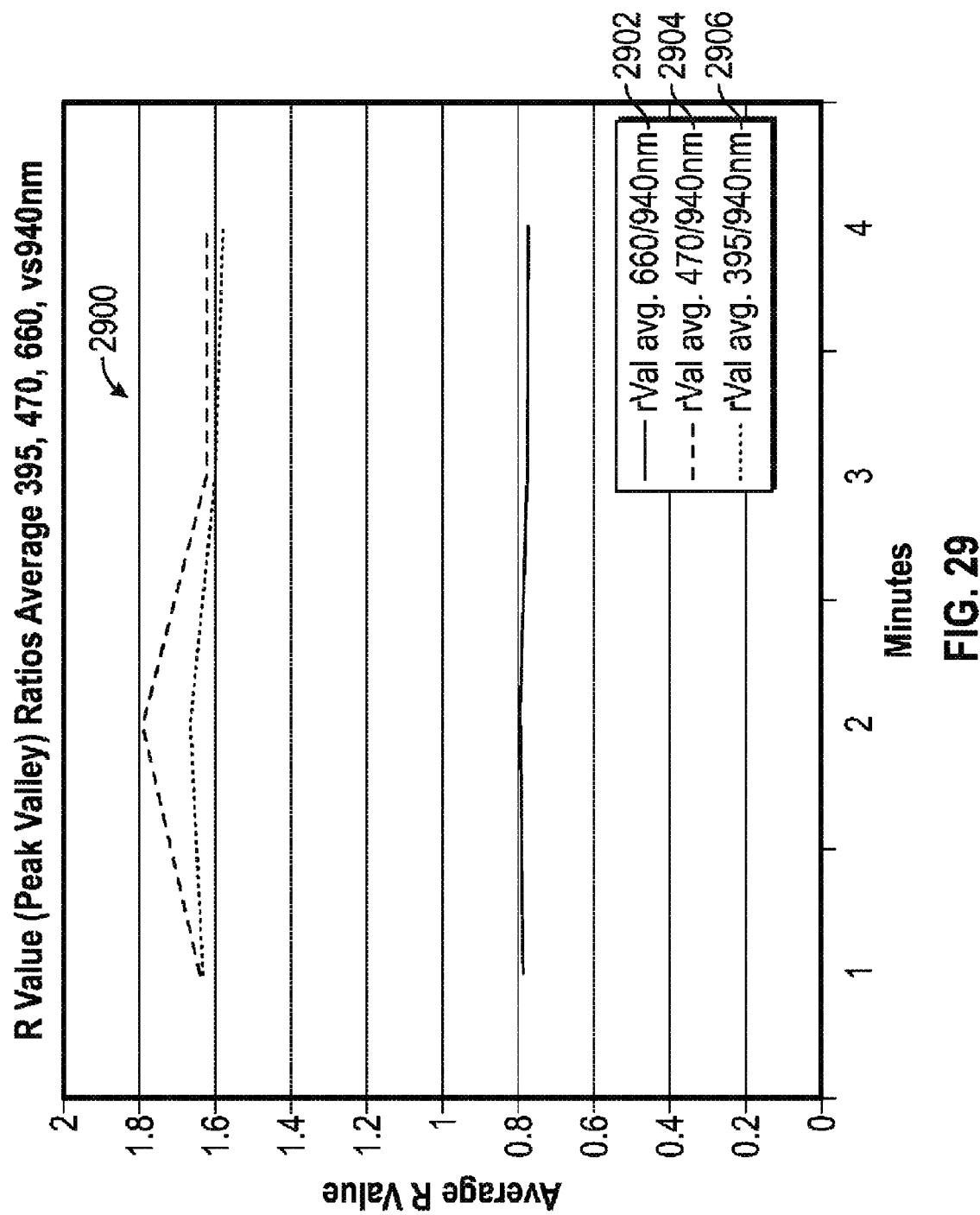
FIG. 29 illustrates a schematic drawing of an exemplary embodiment of results of averaged R values for a plurality of wavelength ratios.

FIG. 29 illustrates a schematic drawing of an exemplary embodiment of results of averaged R values 2900 for a plurality of wavelength ratios. The averaged R values for 395 nm/940 nm 2906, the averaged R values for 470 nm/940 nm 2904 and the averaged R values for 660 nm/940 nm 2906 are shown over a time period of about 4 minutes.

Figure 30A:
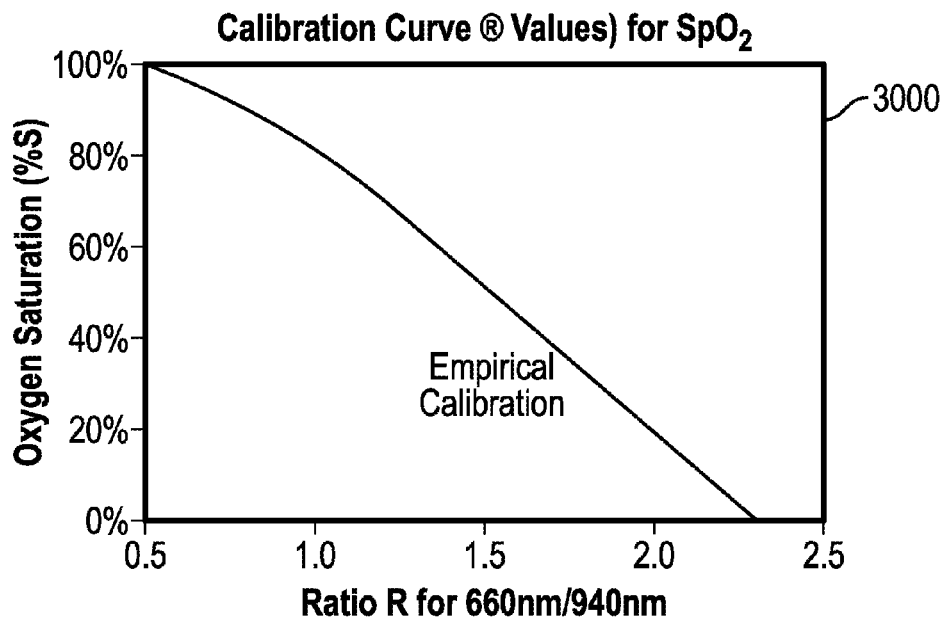
FIG. 30A illustrates a schematic drawing of an exemplary embodiment of a calibration curve for correlating oxygen saturation levels (SpO2) with R values.

FIG. 30A illustrates a schematic drawing of an exemplary embodiment of an empirical calibration curve 3000 for correlating oxygen saturation levels ($SpO_2$) with R values. The calibration curve 3000 may be included as part of the calibration database for the biosensor 100. For example, the R values may be obtained for $L_{660\ nm}/L_{940\ nm}$. In an embodiment, the biosensor 100 may use the 660 nm wavelength to determine SpO2 levels, e.g. rather than IR wavelength range. The 660 nm wavelength has been determined in unexpected results to have good results in measuring oxygenated hemoglobin, especially in skin tissue with fatty deposits, such as around the abdominal area.

Figure 30B:
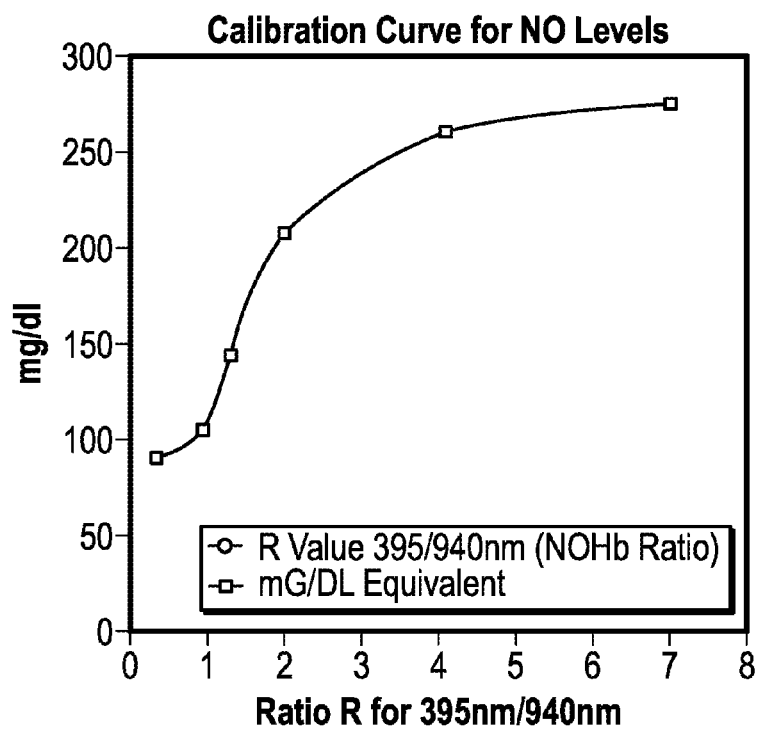
FIG. 30B illustrates a schematic drawing of an exemplary embodiment of a calibration curve for correlating NO saturation levels with R values.

FIG. 30B illustrates a schematic drawing of an exemplary embodiment of an empirical calibration curve 3002 for correlating NO levels (mg/dl) with R values. The calibration curve 3002 may be included as part of the calibration database for the biosensor 100. For example, the R values may be obtained from measurements of $L_{395\ nm}/L_{940\ nm}$ for a general population and the NO levels also measured using one or more other techniques for verification to generate such a calibration curve 3002. This calibration curve 3002 is based on limited clinical data and is for example only. Additional calibration curves 3002 may also be derived from measurements of a general population of patients at one or more different positions of the biosensor 100. For example, a first calibration curve may be obtained at a forehead, another for an abdominal area, another for a fingertip, etc.

From the clinical trials, the L values obtained at wavelengths around 390 nm (e.g. 380-410) are measuring NO levels in the arterial blood flow. The R value for $L_{390}/L_{940\ nm}$ may thus be used to obtain NO levels in the pulsating arterial blood flow. From the clinical trials, it seems that the NO levels are reflected in the R values obtained from $L_{390\ nm}/L_{940\ nm}$ and wavelengths around 390 nm such as $L_{395\ nm}/L_{940\ nm}$. The NO levels may thus be obtained from the R values and a calibration database that correlates the R value with known concentration level of NO for the patient or for a large general population.

In other embodiments, rather than $L_{\lambda 1}$=390 nm, the L value may be measured at wavelengths in a range from 410 nm to 380 nm, e.g., as seen in the graphs wherein $L_{\lambda 1}$=395 nm is used to obtain a concentration level of NO. In addition, $L_{\lambda 2}$ may be obtained at any wavelength at approximately 660 nm or above. Thus, R obtained at approximately $L\lambda 1$=380 nm-400 nm and $L\lambda 2 \geq 660$ nm may also be obtained to determine concentration levels of NO.

Figure 31:
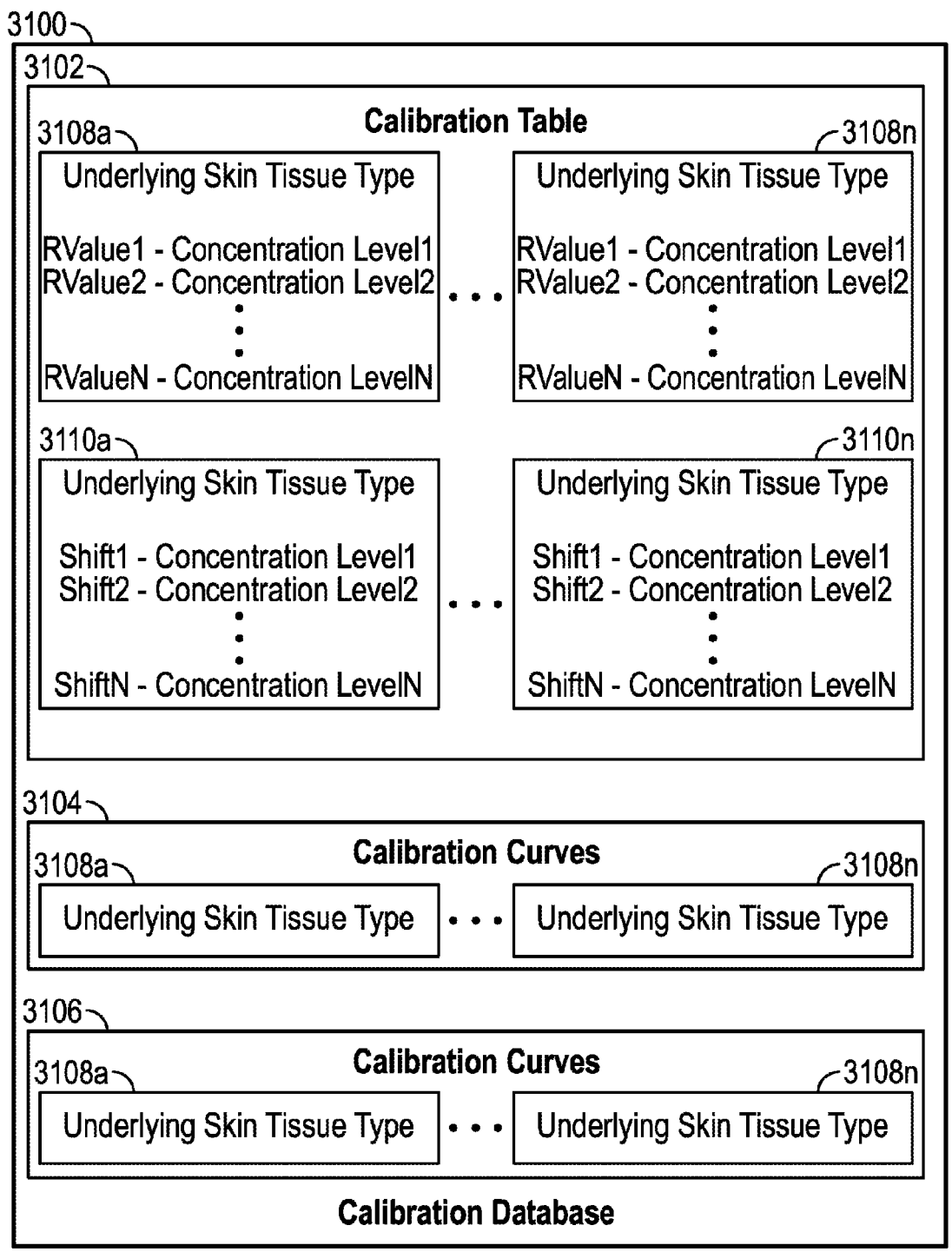
FIG. 31 illustrates a schematic block diagram of an embodiment of a calibration database.

FIG. 31 illustrates a schematic block diagram of an embodiment of a calibration database 3100. The calibration database 3100 includes one or more calibration tables 3102, calibration curves 3104 or calibration functions 3106 for correlating obtained values to concentration levels of NO. The concentration level of NO may be expressed in the calibration tables 3102 as units of mmol/liter, as a saturation level percentage (SpNO %), as a relative level on a scale (e.g., 0-10), etc.

The calibration tables 3102 include one or more calibration tables for one or more underlying skin tissue type 3108*a-n*. In one aspect, the calibration tables 3108 correlate an R value to a concentration level of NO for a plurality of underlying skin tissue types. For example, a first set of tables 3108*a-n* may correlate R values to NO concentration levels for a wrist area, a second table for an abdominal area, a third table for a forehead area, etc.

In another aspect, a set of calibration tables 3110*a-n* correlate an absorption spectra shift to a concentration level of NO for a plurality of underlying skin tissue types. For example, a first table 3110 may correlate a degree of absorption spectra shift of oxygenated hemoglobin to NO concentration levels for a wrist area, a second table 3110 for an abdominal area, a third table 3110 for a forehead area, etc. The degree of shift may be for the peak of the absorbance spectra curve of oxygenated hemoglobin from around 421 nm. In another example, the set of table 3110*s* may correlate a degree of absorption spectra shift of deoxygenated hemoglobin to NO concentration levels for a wrist area, a second table for an abdominal area, a third table for a forehead area, etc. The degree of shift may be for the peak of the absorbance spectra curve of deoxygenated hemoglobin from around 430 nm.

The calibration database 3102 may also include a set of calibration curves 3104 for a plurality of underlying skin tissue types. The calibration curves may correlate L values or R values or degree of shifts to concentration levels of NO.

The calibration database 3102 may also include calibration functions 3106. The calibration functions 3106 may be derived (e.g., using regressive functions) from the correlation data from the calibration curves 3104 or the calibration tables 3102. The calibration functions 3106 may correlate L values or R values or degree of shifts to concentration levels of NO for a plurality of underlying skin tissue types.

Figure 32:
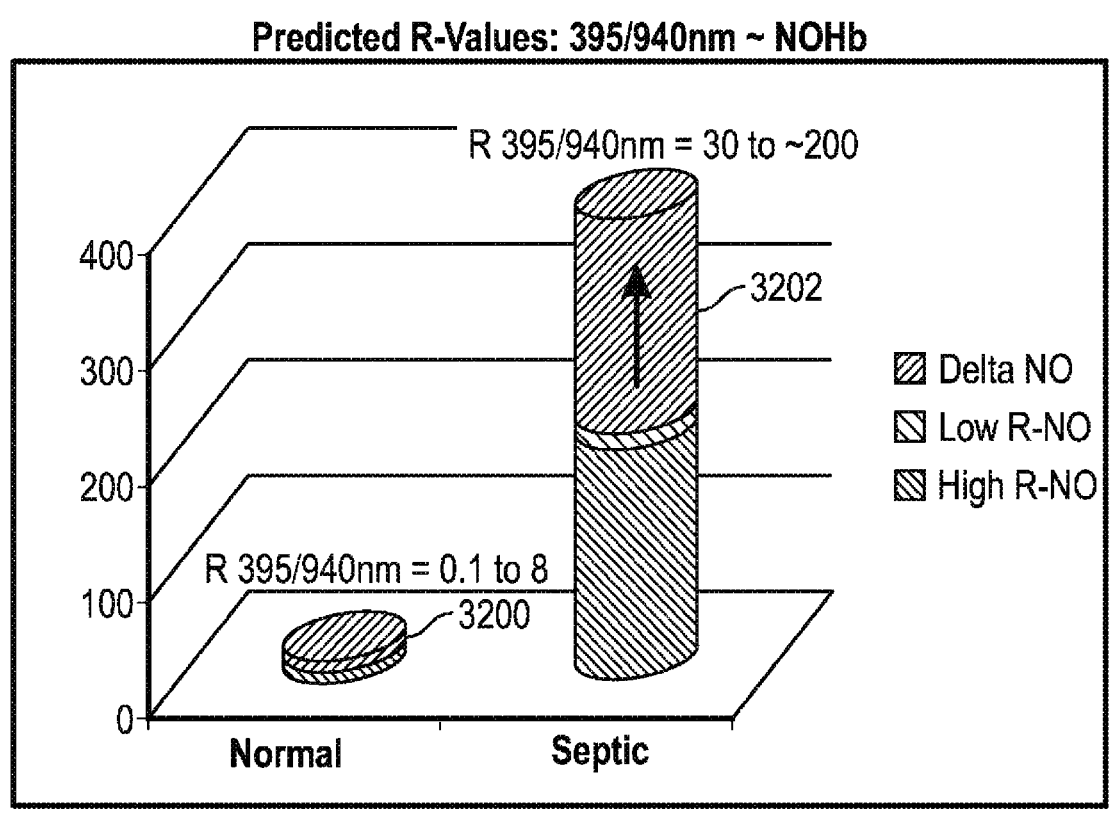
FIG. 32 illustrates a schematic block diagram of an embodiment of predetermined thresholds of NO measurements for detecting a risk of sepsis.

FIG. 32 illustrates a schematic block diagram of an embodiment of predetermined thresholds of NO measurements for detecting a risk of sepsis. In this embodiment, an R value using $L_{395}$ and $L_{940}$ is illustrated as the NO measurement though other thresholds may be obtained using other NO measurements, such as $R_{390/940}$ or $L_{390}$. In the clinical trials herein, the $R_{395/940}$ value for a person without a sepsis condition was in a range of 0.1-8. In addition, it was determined that an R value of 30 or higher is indicative of a patient with a sepsis condition and that an R value of 8-30 was indicative of a risk of sepsis in the patient. In general, an R value of 2-3 times a baseline R value was indicative of a risk of sepsis in the patient.

For example, in the example shown in FIG. 32, a range 3200 of the R value is from 0.1 to 8 for a person without a sepsis condition. The range 3202 of the R value for a person with a sepsis risk is from 30 to 200 or above. These ranges are based on preliminary clinical data and may vary. In addition, a position of the biosensor, pre-existing conditions of a patient or other factors may alter the numerical values of the ranges of the R values described herein.

The R values are determined by measuring NO concentration level directly using a wavelength in the UV range with high absorption coefficient for NO, e.g. in a range of 380 nm-410 nm. These R values have a large dynamic range from 0.1 to 300 and above. The percentage variance of R values in these measurements is from 0% to over 3,000%. The R values obtained by the biosensor 100 are thus more sensitive and may provide an earlier detection of septic conditions than blood tests for serum lactate or measurements based on MetHb.

For example, an optical measurement of MetHb in blood vessels is in a range of 0.8-2. This range has a difference of 1.1 to 1.2 between a normal value and a value indicating a septic risk. So these measurements based on MetHb have less than a 1% percentage variance. In addition, during a septic condition, MetHb may become saturated due to the large amount of NO in the blood vessels. So, an optical measurement of MetHb alone or other hemoglobin species alone is not able to measure these excess saturated NO levels. The R values determined by measuring NO level directly using a wavelength in the UV range are thus more sensitive, accurate, have a greater dynamic range and variance, and provide an earlier detection of septic conditions.

In an embodiment, the patch 102 may be configured with corresponding thresholds to trigger one or more health alerts. For example, the patch 102 may be configured to indicate a non-septic range of NO levels for $R_{395/940}$ values from 0.1 to 8. For $R_{395/940}$ values from 8 to 30, the patch may indicate a risk of sepsis or infection. A healthcare provider may determine to continue monitoring or perform additional tests or begin a treatment for infection. For $R_{395/940}$ values at 30 or above, the patch may be configured to indicate a second alert indicating a high health risk or onset of sepsis. A healthcare provider may determine to immediately begin an aggressive treatment for infection or perform additional treatments and intervention.

FIG. 33 illustrates a logical flow diagram of an embodiment of a method 3300 for determining predetermined thresholds for health alert indicators for sepsis. A baseline NO measurement in blood vessels of a healthy general population is obtained in 3302. For example, the biosensor 100 may obtain R values or other NO measurements using the biosensor 100. For example, the biosensor 100 may measure an $L_{395}$ value or determine SpNO % based on an R value for a general population over a period of time, such as hours or days. These NO measurements are then averaged to determine a baseline NO measurement.

The NO measurement in blood vessels is then obtained for a general population with a diagnosis of sepsis at 3304. For example, the biosensor 100 may obtain R values or other NO measurements (such as an $L_{395}$ value or SpNO %) for patients diagnosed with sepsis using traditional blood tests, such as serum lactate blood tests. The biosensor 100 may monitor the patients throughout the diagnosis and treatment stages. The NO measurements are then averaged to determine a range of values that indicate a septic condition.

Predetermined thresholds may then be obtained from the NO measurements at 3306. For example, a threshold value indicative of a non-septic condition may be obtained. A threshold value for a septic condition may also be obtained. The biosensor 100 is then configured with the predetermined thresholds for the NO measurement at 3308.

The predetermined thresholds may be adjusted based on an individual patient's pre-existing conditions. For example, a patient with diabetes may have lower R values. A baseline NO value for a patient may also be determined based on monitoring of the patient during periods without infections. The predetermined thresholds stored in the bio sensor 100 may then be adjusted based on any individual monitoring and/or pre-existing conditions.

In addition, the predetermined thresholds may be determined and adjusted based on positioning of the biosensor 100. For example, different R values or other NO measurements may be obtained depending on the characteristics of the underlying tissue, such as tissue with high fatty deposits or with dense arterial blood flow. The thresholds and other configurations of the biosensor 100 may thus be adjusted depending on the underlying skin tissue, such as a forehead, chest, arm, leg, finger, abdomen, etc.

Figure 34A:
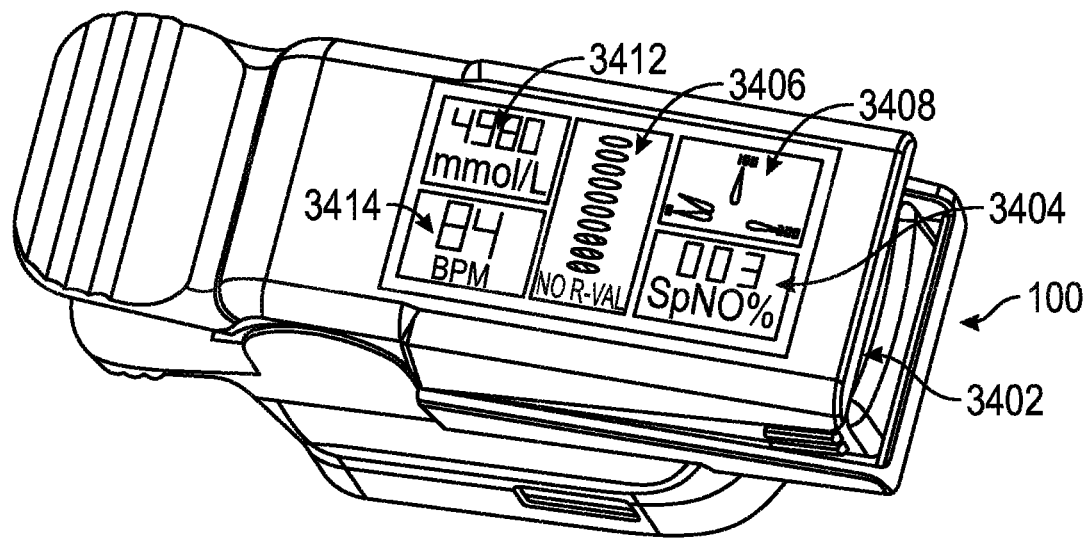
FIG. 34A illustrates a perspective view of an embodiment of another form factor of the biosensor.
Figure 34B:
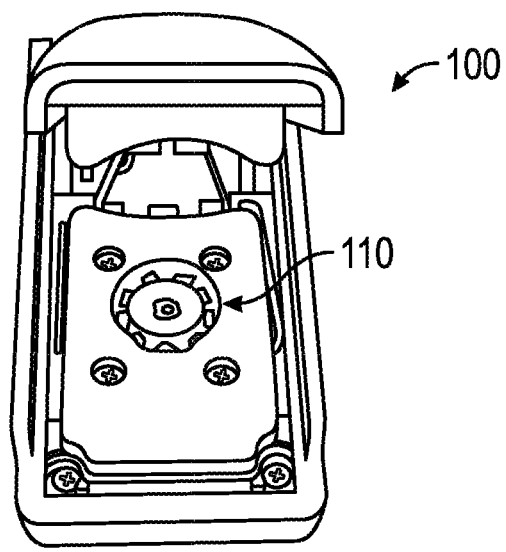
FIG. 34B illustrate another perspective view of an embodiment of another form factor of the biosensor.

FIGS. 34A and 34B illustrates illustrate a perspective view of another embodiment of the biosensor 100. In this embodiment, the biosensor 100 includes a finger attachment 3402. The finger attachment 3402 includes the PPG circuit 110 and is configured to securely hold a finger that is inserted into the finger attachment 3402.

In use, a patient places a finger inside the finger attachment 3402. The biosensor 100 is configured to monitor nitric oxide (NO) levels in the blood vessels of the patient using one or more methods described herein. The NO levels may be continuously monitored, e.g. the NO measurements may be obtained a plurality of times per minute and averaged over a predetermined time period. An indication of the NO levels may then be displayed on a display of the biosensor 100.

The biosensor 100 displays one or more indications of the NO levels. The displays may include, e.g., arterial nitric oxide saturation level 3404 (such as SpNO %). The display may include a bar meter 3406 illustrating a relative measured NO level. The display may include a dial type display 3408 that indicates a relative measured NO level. The biosensor 100 may display the measured NO level in mmol/liter units 3412. These types of displays are examples only and other types of display may be employed to indicate the level of NO measured in a patient. The biosensor 100 may also obtain and display other patient vitals such as pulse rate, respiration rate and temperature.

The biosensor 100 may be implemented in other compact form factors, such as on a patch, wrist band or ear piece. Due to its compact form factor, the biosensor 100 may be configured for measurements on various skin surfaces of a patient, including on a forehead, arm, wrist, abdominal area, chest, leg, ear, ear lobe, finger, toe, ear canal, etc.

Figure 35B:
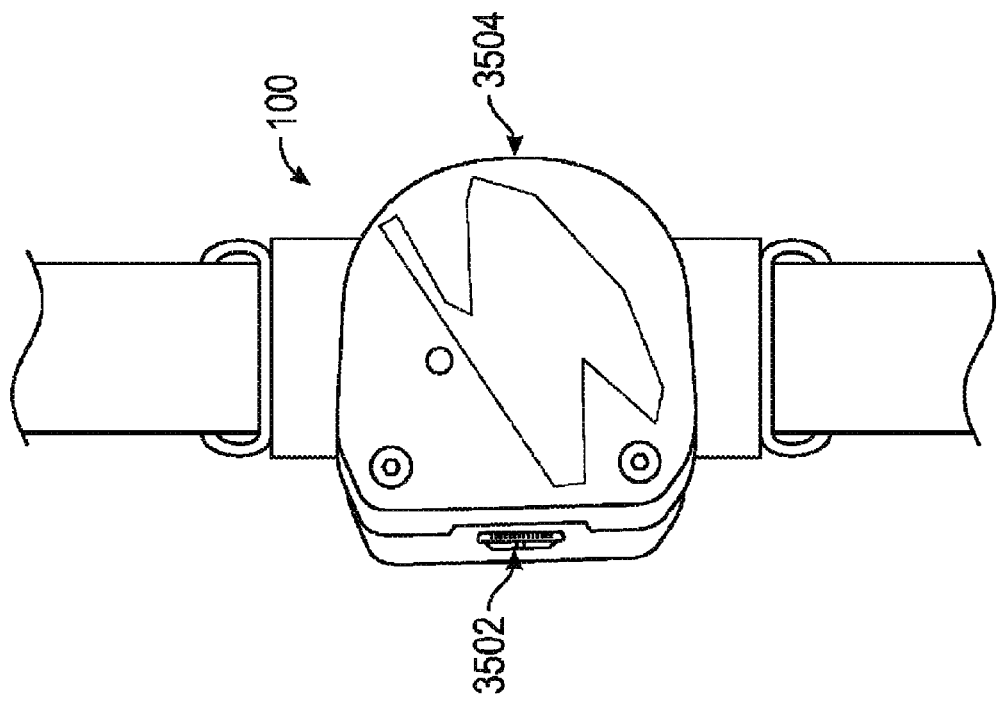
FIG. 35B illustrates another perspective view of an embodiment of another form factor of the biosensor.
Figure 35A:
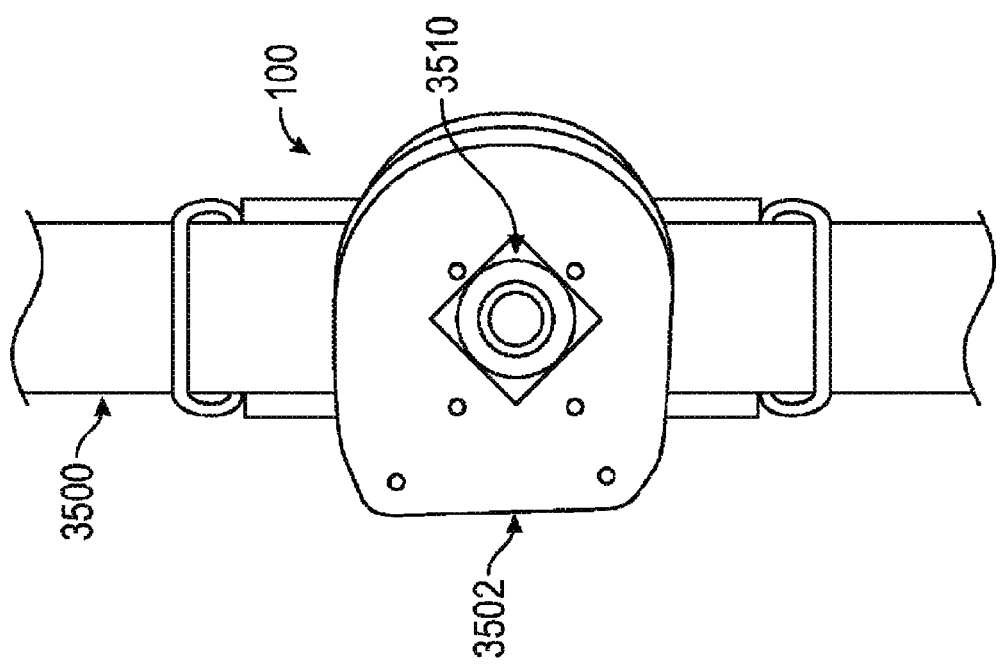
FIG. 35A illustrates a perspective view of an embodiment of another form factor of the biosensor.

FIG. 35A and FIG. 35B illustrate a perspective view of another embodiment of the biosensor 100. In this embodiment, the biosensor 100 is implemented with an adjustable band 3500. The adjustable band 3500 may be configured to fit around a wrist, arm, leg, ankle, forehead, etc. FIG. 35A illustrates a first side 3502 of the biosensor 100 that includes at least one opening for the PPG circuit 110 to emit light directed to skin tissue and detect light reflected from the skin tissue of a user. FIG. 35B illustrates a second side 3504 of the biosensor 100 that may include a display (not shown). A USB or other port 3506 may be implemented to transmit data to and from the biosensor 100. The biosensor 100 may alternatively or additionally include a wireless transceiver.

Figure 36:
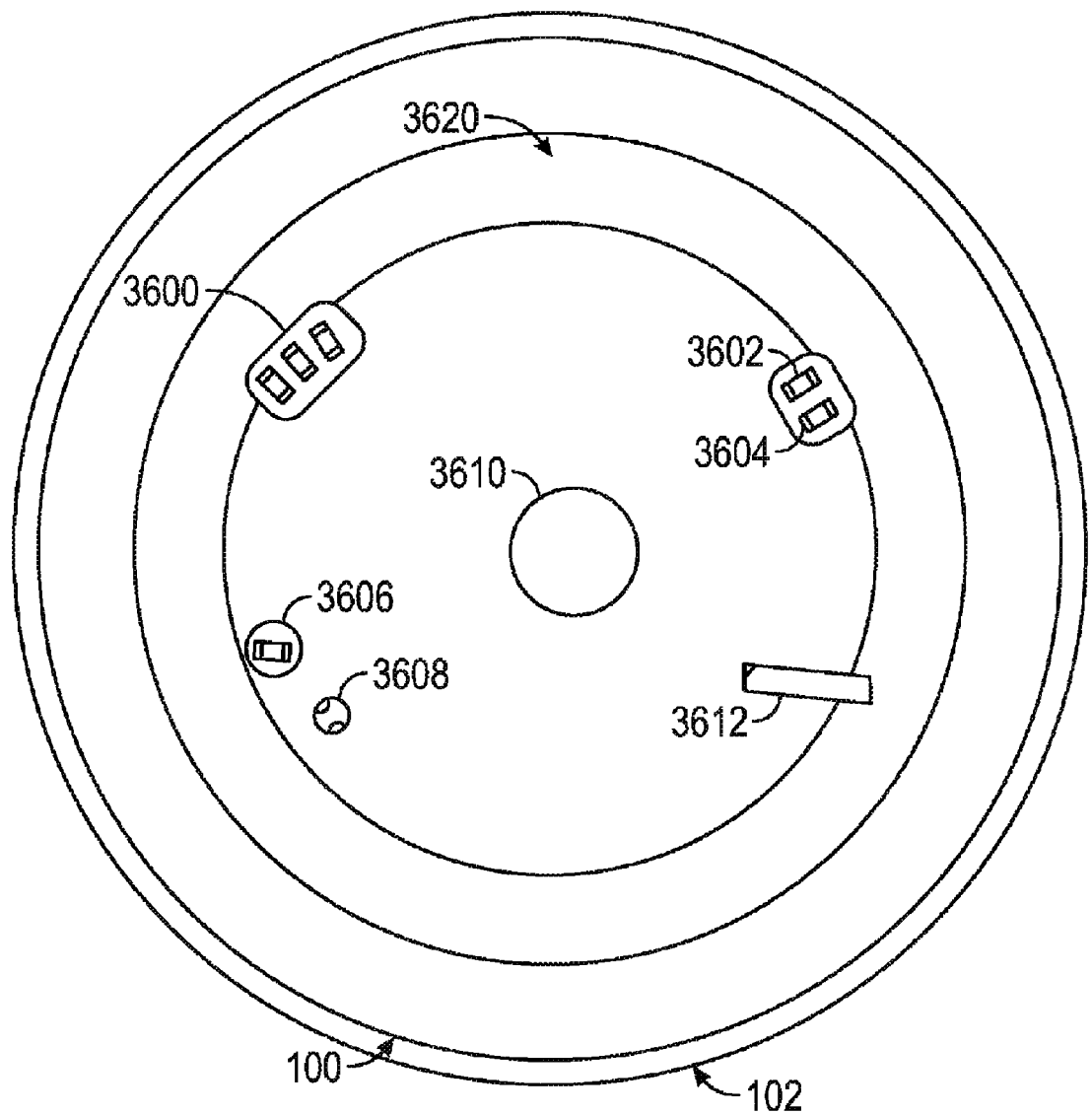
FIG. 36 illustrates a perspective view of a first side of another embodiment of the biosensor.

FIG. 36 illustrates a perspective view of a first side of another embodiment of the biosensor 100. In this embodiment, the patch 102 may be configured to operate in one or more of a plurality of modes. The plurality of modes include, e.g. a sepsis indicator, a glucose level indicator, $SpO_2$ monitor, heart rate monitor, temperature monitor, respiration monitor, etc. For example, in a first mode, the patch 102 may monitor NO levels and provide an indication of risk of a sepsis condition. In another mode, the patch 102 may monitor NO levels and provide an indication of diabetic risk and/or glucose levels. In another embodiment, the patch 102 may monitor oxygenated hemoglobin and provide an indication of SpO$_2$ levels. The patch 102 may also provide an indication of temperature, heart rate and/or respiration rate.

The first side 3620 of the patch 102 is configured to face upwards away from skin tissue of a patient. A user interface circuit 3610 is configured to provide a user with control to select one or more modes of operation. In one embodiment, the user interface circuit 3610 may include a push button or dial. In another embodiment, the patch 102 includes an accelerometer that detects pressure applied to a surface of the patch 102. The user may thus tap or otherwise apply pressure to a surface of the patch 102 to select a mode of operation. In addition, the user interface circuit 3610 may be used to control alerts. For example, the user interface circuit 3610 may be used to reset an audible alert or visual alert, increase volume of an audible alert, etc. A mode indicator 3604 is configured to indicate the mode of operation of the patch 102. In an embodiment, the mode indicator 3604 may include one or more LEDs that illuminate to illustrate one or more modes of operation.

The patch 102 may also include a range indicator 3600 that indicates a range or level of a substance being monitored, such as NO level, SpO$_2$, etc. The range or level indicator 3600 in an embodiment includes an array of LEDs that illuminate to indicate the range or level of a measured substance. The patch 102 may also include a health alert indicator 3606 to provide a warning or health alert. The health alert indicator 3606 in this embodiment includes a first LED 110 that may illuminate to provide a status or indication of a health condition. For example, the LED may illuminate a first color (e.g. green) to indicate no or little health risk has been detected while a second color (e.g. red) may indicate that health risks are detected. For example, depending on the mode of operation, the health alert indicator 3606 may illuminate to alert that symptoms have been detected indicating a risk of sepsis or high NO levels have been detected. In another example, the health alert indicator 3606 may indicate a high heart rate, temperature or respiration rate has been detected. In another mode, the health alert indicator 3608 may activate upon detection of a diabetic risk, such as on detection of low levels of NO. In another mode, the health alert indicator 3606 may activate upon detection of high or low glucose concentration levels. The patch 102 may in addition to or alternatively include an audible indicator 3608 configured to provide audible or verbal indications or alerts. The visible indicator may also include a digital display.

The patch 102 may also include a heart rate (bpm) indicator 3602. The heart rate indicator 3602 may include an LED that blinks or changes color upon detection of a heartbeat. A person may thus count a number of heartbeats using the flashing LED. In another example, the patch 102 may indicate a pulse rate has reached or exceeded a predetermined threshold (such as over 100 bpm).

Though a plurality of different LEDs are described herein to provide various types of information and alerts, the patch 102 may implement other types of user interfaces, such as a display or touchscreen or a verbal interface, to provide such alerts and information. The patch 102 may also include a transceiver 3612, wired or wireless, to communicate with another device. For example, the transceiver 3612 may include a USB port for a wired communication or an RFID or Bluetooth wireless transceiver. The transceiver 3612 may communicate configuration information to the patch 102 or communicate data from the patch 102 to a user device or other type of remote device.

Figure 37:
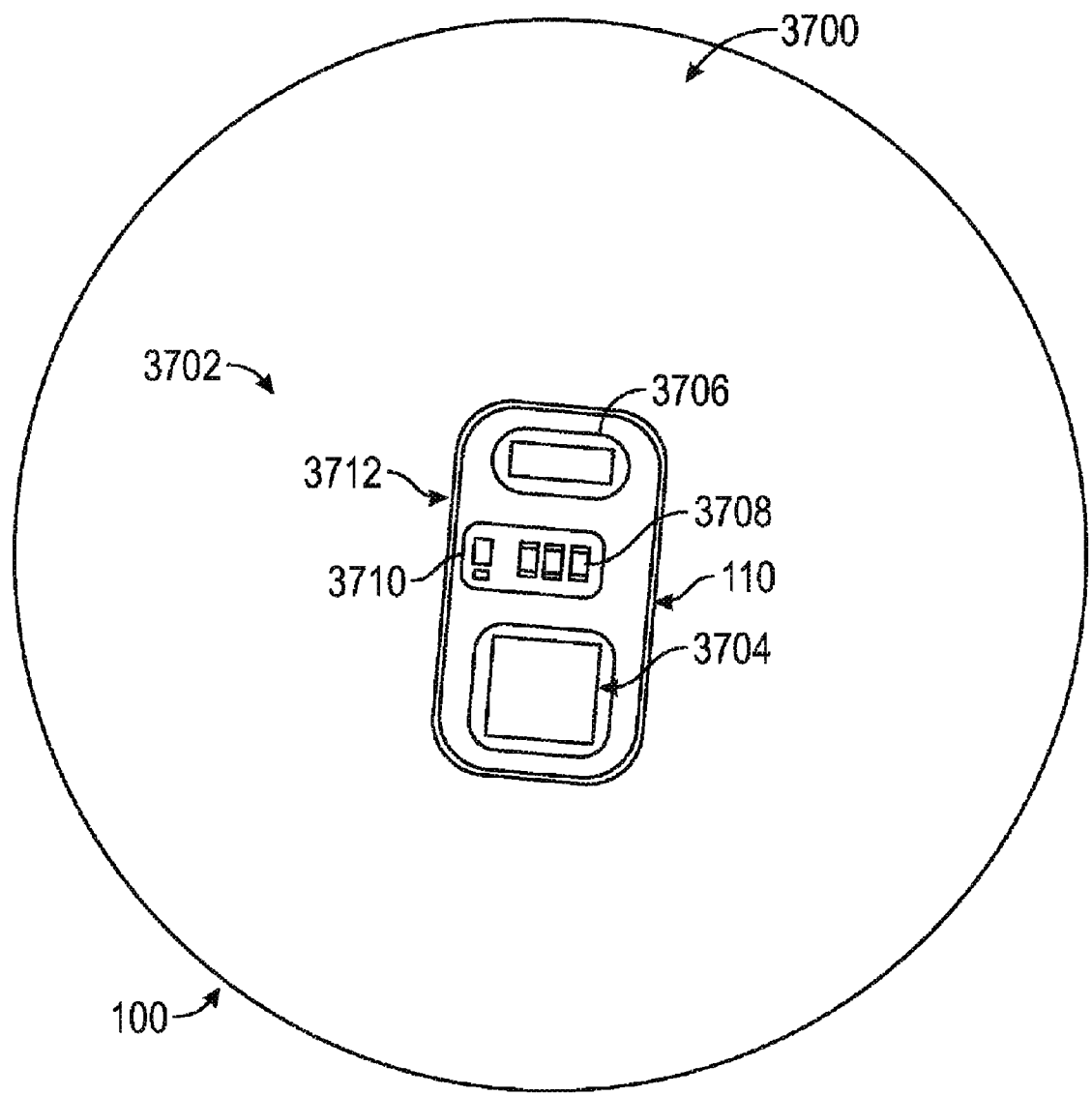
FIG. 37 illustrates a perspective view of a second side of an embodiment of the biosensor.

FIG. 37 illustrates a perspective view of a second side 3700 of an embodiment of the biosensor 100. The second side 3700 of the patch 102 is configured to face towards skin tissue of a user. The PPG 110 includes at least a first photodiode 3704 and may also include a second photodiode 3706. The photodiodes 3704, 3706 are positioned on opposite sides of a plurality of LEDs 3708. The LEDs 3708 are configured to emit light at a plurality of wavelengths. For example, a first wavelength is in a UV range of 380-410 nm and is preferably 390 nm or 395 nm. A second wavelength is in an IR range, such as approximately 660 nm, and a third wavelength is an IR range, such as approximately 940 nm. Additional or alternative LEDs may be included that have different wavelengths depending on the substance or patient vitals to be detected. The patch 102 may also include a temperature sensor 3710 configured to detect a skin temperature of the patent. A gasket 3712 is implemented to hold the PPG circuit 110 in position.

Figure 38:
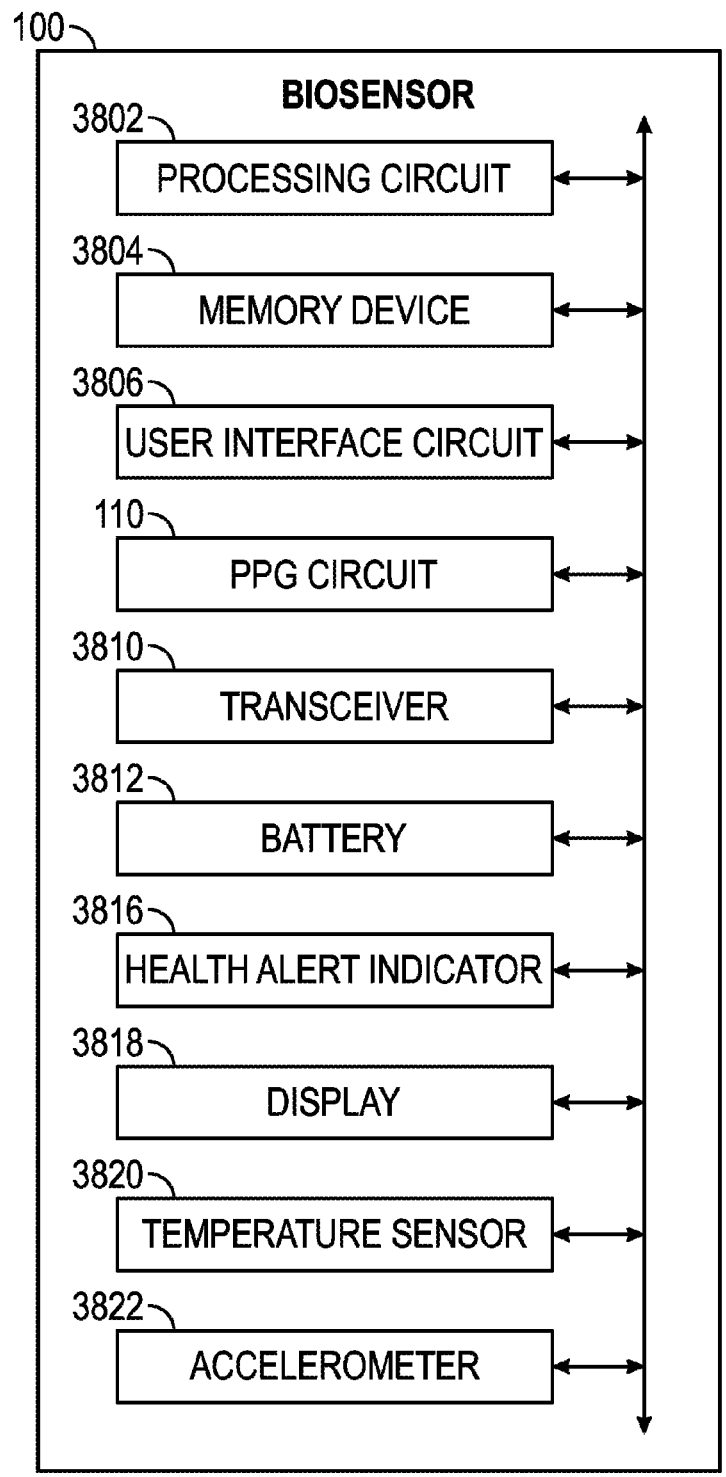
FIG. 38 illustrates a schematic block diagram of an exemplary embodiment of components of the biosensor.

FIG. 38 illustrates a schematic block diagram of an exemplary embodiment of components of the biosensor 100. The biosensor 100 includes the PPG circuit 110 as described herein. The PPG circuit 110 may be configured to detect oxygen saturation (SaO2 or SpO2) levels in blood flow, as well as heart rate and respiration rate. The PPG circuit 110 is configured to detect concentration levels or indicators of NO levels in the blood and/or other substances such as a liver enzyme cytochrome oxidase (P450) enzyme.

The biosensor 100 also includes one or more processing circuits 3802 communicatively coupled to a memory device 3804. In one aspect, the memory device 3804 may include one or more non-transitory processor readable memories that store instructions which when executed by the one or more processing circuits 3802, causes the one or more processing circuits 3802 to perform one or more functions described herein. The memory device 3804 may also include an EEPROM or other type of memory to store a patient identification (ID) that is associated with a patient being monitored by the biosensor 100. The patient identification may include a number, name, date of birth, password, etc. The biosensor data obtained by the biosensor 100 may be stored in the memory device 3804. The processing circuit 3802 may be co-located with one or more of the other circuits in a same circuit board of the biosensor 100 or located separately in a different circuit board or physical encasement. One or more functions of the processing circuit 3802 may be performed by another processing circuit located remotely as well. In an embodiment, the biosensor 100 is battery operated and includes a battery 3812, such as a lithium ion battery.

A user interface circuit 3806 is configured to provide a user with control to select one or more modes of operation or otherwise configure the biosensor 100. In one embodiment, the user interface circuit 3806 may include a push button or dial. In another embodiment, an accelerometer 3822 detects pressure applied to a surface of the patch 102. The user may thus tap or otherwise apply pressure to a surface of the patch 102 to select a mode of operation or otherwise configure the biosensor 100. In addition, the user interface circuit 3806 may be used to control alerts. For example, the user interface circuit 3806 may be used to reset an audible or visual alert, increase volume of an audible alert, etc.

The biosensor 100 further includes a transceiver 3810. The transceiver 3810 may include a wireless or wired transceiver configured to communicate with one or more devices over a LAN, MAN and/or WAN. In one aspect, the transceiver 3810 may include a Bluetooth enabled (BLE) transceiver or IEEE 802.11ah, Zigbee, IEEE 802.15-11 or WLAN (such as an IEEE 802.11 standard protocol) compliant wireless transceiver. In another aspect, the transceiver 3810 may operate using RFID, short range radio frequency, infrared link, or other short range wireless communication protocol. In another aspect, the transceiver 3810 may also include or alternatively include an interface for communicating over a cellular radio access network, such as an Universal Mobile Telecommunications System (UMTS) Terrestrial Radio Access Network (UTRAN), Long Term Evolution (LTE) Evolved UTRAN (E-UTRAN), and/or LTE-Advanced (LTE-A) or other types of cellular networks. In an embodiment, the transceiver 3810 may include a thin foil for an antenna that is specially cut and includes a carbon pad contact to a main printed circuit board (PCB) of the biosensor 100. This type of antenna is inexpensive to manufacture and may be printed on the inside of an enclosure for the biosensor 100 situated away from the skin of the patient to minimize absorption. The transceiver 3810 may also include a wired transceiver including a port or interface, e.g., a USB port or other type of wired connection port, for communication with one or more other devices using Ethernet, IP, or other protocols over a LAN, MAN and/or WAN.

The biosensor 100 may also include a temperature sensor 3820 configured to detect a temperature of a patient. For example, the temperature sensor 3820 may include an array of sensors (e.g., 16×16 pixels) positioned on a side of the biosensor 100 with the PPG circuit 110 such that the array of sensors are adjacent to the skin of the patient. The array of sensors is configured to detect a temperature of the patient from the skin. The temperature sensor 3820 may also be used to calibrate the PPG circuit 110, such as the wavelengths of the LEDs.

The biosensor 100 may also include a display 3818 for displaying biosensor data, mode of operation, alerts, configuration data, etc. The display 3818 may include one or more LEDs as described herein or include a digital display or other means for indicating information to a user. Alternatively or in addition thereto, the transceiver 3810 may communicate biosensor data and alerts to a remote device for display.

Figure 39:
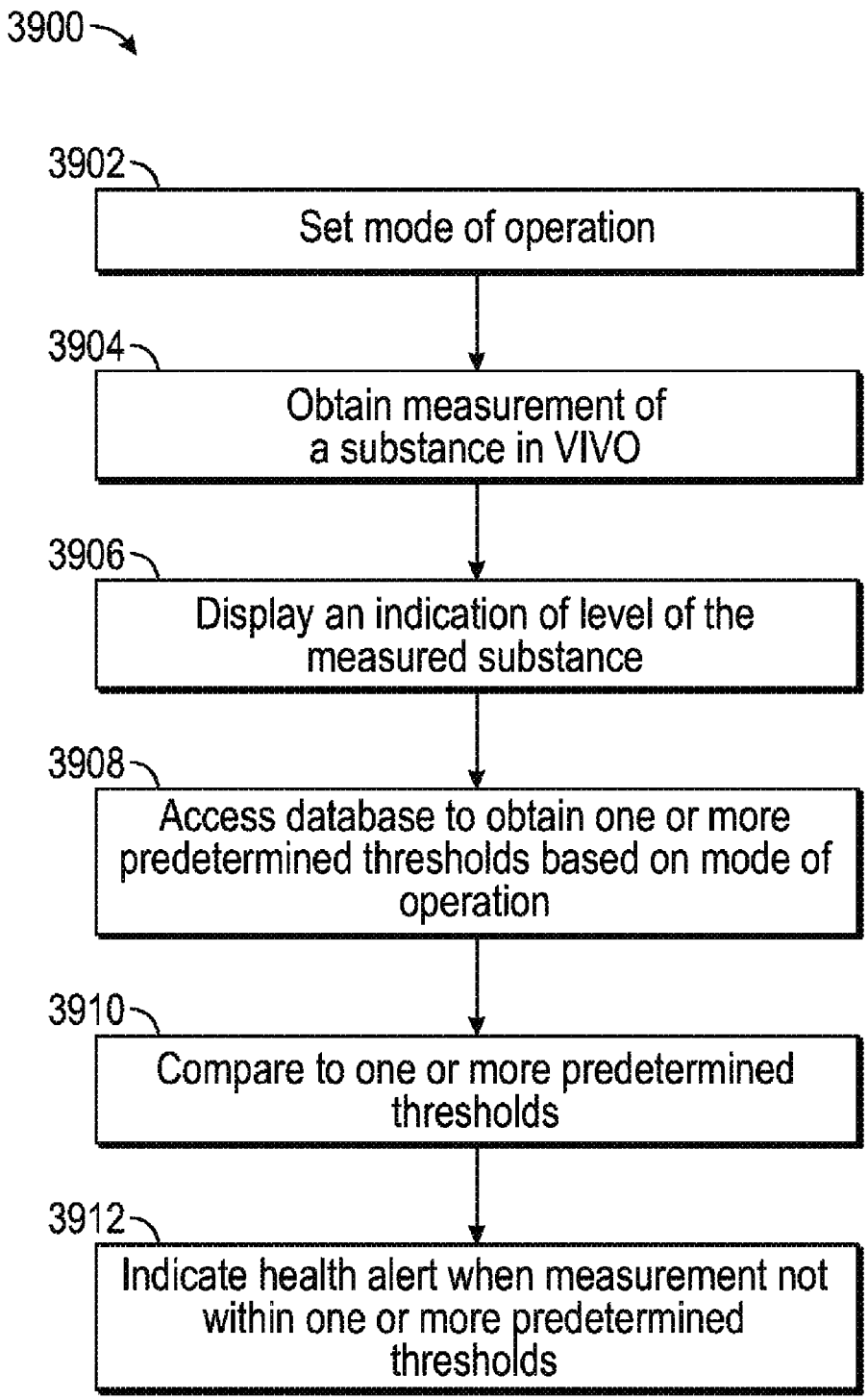
FIG. 39 illustrates a logical flow diagram of an embodiment of a method for operation of the biosensor.

FIG. 39 illustrates a logical flow diagram of an embodiment of a method 300 for operation of the biosensor 100. In this embodiment, the biosensor 100 may be configured to operate in one or more of a plurality of modes. The plurality of modes include, e.g. a sepsis indicator, a glucose level indicator, a diabetic indicator, $SpO_2$ monitor, heart rate monitor, temperature monitor, respiration monitor, etc. For example, in a first mode, the biosensor 100 may monitor NO levels and provide an indication of risk of a sepsis condition. In another mode, the biosensor 100 may monitor NO levels and provide an indication of diabetic risk and/or glucose levels. In another embodiment, the biosensor 100 may monitor oxygenated hemoglobin and provide an indication of $SpO_2$ levels. The biosensor 100 may also provide an indication of temperature, heart rate and/or respiration rate in one or more of the above modes or in other modes of operation.

The biosensor 100 is configured to operate in one or more modes of operation at 3902. The biosensor 100 obtains a measurement of a substance in vivo, e.g. in blood vessels or tissue of a patient, using one or more of the non-invasive methods described herein. The measured substance depends on the mode of operation. For example, in a first mode, the biosensor 100 may monitor NO levels in vivo. In another mode of operation, the biosensor 100 may monitor oxygenated hemoglobin in vivo. In another mode of operation, the biosensor 100 may monitor a liver enzyme cytochrome P450 (P450) enzyme in vivo indicative of blood alcohol levels. Measurements of other substances, such as bilirubin, sodium or potassium, may also be obtained and monitored by the biosensor 100. The biosensor 100 then displays an indication of the level of the measured substance in the blood vessels and/or skin tissue of the patient at 3906.

The biosensor 100 accesses a database in a memory to obtain one or more predetermined thresholds based on the mode of operation at 3908. For example, when operating in a mode of operation to monitor risk of sepsis, the biosensor 100 may obtain one or more predetermined thresholds of an NO measurement. When operating in a mode of operation to monitor SpO2 percentages, the biosensor 100 may obtain one or more predetermined thresholds of oxygenated hemoglobin. When operating in a mode of operation to monitor blood alcohol levels, the biosensor 100 may obtain one or more predetermined thresholds of P450 enzyme.

The biosensor 100 then compares an obtained measurement or level for the substance with the one or more predetermined thresholds at 3910. The biosensor 100 then indicates a health alert when an obtained measurement or level for the substance is not within one or more of the predetermined thresholds at 3912.

Embodiment—Detection of Other Conditions Based on NO Levels

Diabetic conditions may result in lower than normal NO levels. Based on R values, the biosensor 100 may determine a base insulin resistance factor based on the value $R_{\lambda 1, \lambda 2}$ that indicates a diabetic risk indicator of a person, as described in more detail in The present application claims priority under 35 U.S.C. §120 as a continuation in part to U.S. patent application Ser. No. 14/866,500 entitled, "SYSTEM AND METHOD FOR GLUCOSE MONITORING," filed Sep. 25, 2015, and hereby expressly incorporated by reference herein. For example, from unexpected results of clinical trials, an R value was obtained at approximately $L_{\lambda 1}$=390 nm and $L_{\lambda 2}$=940 nm by a biosensor 100 from a fingertip of a patient during a period of fasting, e.g. prior to ingestion of food or liquids. It was shown that such an $R_{390/940}$ value of less than 1 (e.g., approximately 0.5) indicated that a person has diabetes or early onset of diabetes. An $R_{390/940}$ value of 2 or above indicated that a person has a lower risk of a diabetes diagnosis. An $R_{390/940}$ value in the 5-6 range indicated no current risk of diabetes. In addition, an $R_{390/940}$ value may measure an insulin response of the patient after caloric intake over a measurement period. These unexpected results have advantages in early detection of diabetic risk and easier, non-invasive monitoring of insulin response and glucose levels.

In addition, carbon monoxide poisoning may result in higher than normal NO levels. Other compounds may also cause unsafe levels of NO in blood vessels, such as lidocaine and nitrates such as nitroglycerine, nitric oxide, or water sources contaminated by runoff containing nitrogen based fertilizers, anti-malaria drug dapsone, benzocaine, cyanide, anesthesia, nitroglycerin, nitrate drugs, water contaminated with nitro based fertilizers, landocaine, etc. The biosensor 100 may operate in one or more modes to detect or provide a warning of abnormal NO levels that may indicate one or more of these conditions.

Embodiment—Measurement of Other Substances

Using similar principles described herein, the biosensor 100 may measure concentration levels or indicators of other substances in pulsating blood flow. For example, absorption coefficients for one or more frequencies that have an intensity level responsive to concentration level of substance may be determined. The biosensor 100 may then detect the substance at the determined one or more frequencies as described herein and determine the concentration levels using the Beer-Lambert principles and the absorption coefficients. The L values and R values may be calculated based on the obtained spectral response. In one aspect, the biosensor 100 may detect various electrolyte concentration levels or blood analyte levels, such as bilirubin and potassium. In another aspect, the biosensor 100 may detect sodium NACL concentration levels in the arterial blood flow to determine dehydration.

In another aspect, the biosensor may indicate blood alcohol levels. For example, a disposable patch 102 may be configured to detect alcohol levels, e.g. by using an LED emitting a wavelength at 468 nm or in a range around 468 nm (e.g. 450-480 nm) and an LED emitting a wavelength at 940 nm or in a range around 940 nm (e.g. 920-960 nm). The biosensor 100 detects a liver enzyme cytochrome P450 (P450) based on spectral responses using the LEDs at these wavelengths and then provides an indicator of blood alcohol levels using a calibration database.

In another aspect, the biosensor 100 may detect white blood cell counts in arterial blood flow using similar PPG techniques. The presence of white blood cell counts may also be used as an indicator of the presence of an infection.

In another aspect, abnormal cells or proteins or compounds that are present or have higher concentrations in the blood with persons having cancer, may be detected using similar PPG techniques described herein at one or more other wavelengths. Thus, cancer risk may then be obtained through non-invasive testing by the biosensor 100.

In another aspect, the biosensor 100 may measure levels of one or more hemoglobin species. The biosensor 100 may then provide an indication of hemoglobin levels in the blood or the level of an individual one of the hemoglobin species.

In one or more modes of operation, the biosensor 100 may thus be configured to detect one or more of these other substances in addition to or alternatively from NO levels.

Figure 40A:
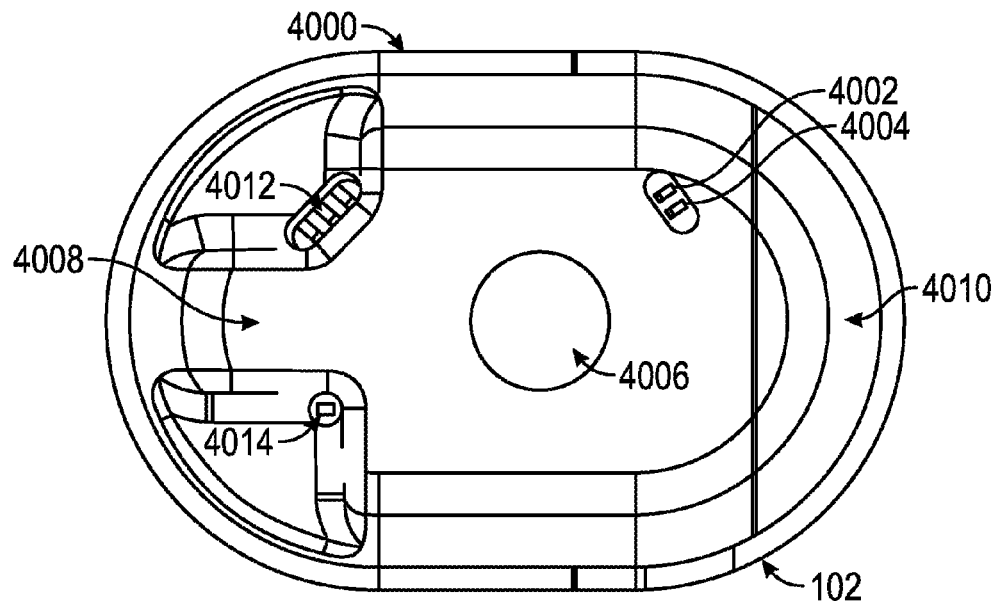
FIG. 40A illustrates a perspective view of an embodiment of a patch form factor of the biosensor.
Figure 40B:
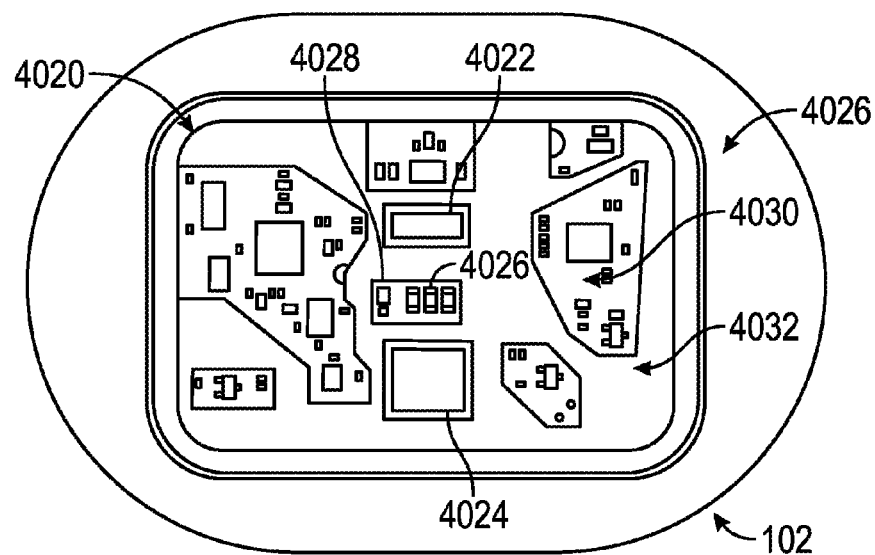
FIG. 40B illustrates another perspective view of another embodiment of a patch form factor of the biosensor.

FIGS. 40A and 40B illustrate perspective views of another embodiment of the patch 102. In this embodiment, the patch 102 may also be configured to operate in one or more of a plurality of modes. FIG. 40A illustrates a first side 4000 of the patch 102 configured to face upwards away from skin tissue of a patient. A mode indicator 4004 is configured to indicate the mode of operation of the patch 102. In an embodiment, the mode indicator 4004 may include one or more LEDs that illuminate to illustrate one or more modes of operation. A user interface circuit 4006 is configured to provide a user with control to select one or more modes of operation. In one embodiment, the user interface circuit 4006 may include a push button or dial. In another embodiment, the user interface circuit 4006 includes an accelerometer that detects pressure applied to a surface of the patch 102. The user may thus tap or otherwise apply pressure to a surface of the patch 102 to select a mode of operation. In addition, the user interface circuit 4006 may be used to control alerts. For example, the user interface circuit 4006 may be used to reset an audible or visual alert, increase volume of an audible alert, etc.

The patch 102 may also include a range indicator 4012 that indicates a range or level of a substance being monitored, such as NO level, SpO2, etc. The range indicator 4012 in an embodiment includes an array of LEDs that illuminate to indicate the range or level of a measured substance. The patch 102 may also include a health alert indicator 4014 to provide an audible or visual warning or health alert. The health alert indicator 4014 in this embodiment includes a first LED that may illuminate to provide a status or indication of a health condition. The patch 102 may in addition to or alternatively include an audible alert or a digital display as the health alert indicator 4014.

The patch 102 may also include a rate indicator 4002. The rate indicator 4002 may include an LED that blinks or changes color upon detection of a heartbeat. A person may thus count a number of heartbeats using the flashing LED to determine a heart rate. In another example, the patch 102 may indicate a heart rate has reached or exceeded a predetermined threshold (such as over 100 bpm) using the rate indicator 4002 or health alert indicator 4014. In another mode of operation, the rate indicator 4002 may indicate a respiration rate by flashing or changing color upon each respiration cycle. In another example, the patch 102 may indicate a respiration rate has reached or exceeded a predetermined threshold (such as over 100) using the rate indicator 4002 or health alert indicator 4014. Though a plurality of different LEDs are described herein to provide various types of information and alerts, the patch 102 may implement other types of user interfaces, such as a display or touchscreen or a verbal interface, to provide such alerts and information.

In an embodiment, the patch 102 includes an outer shell having a first piece 4008 and a second piece 4010. The first piece 4008 and the second piece 4010 may comprise a plastic material and be slidably coupled together.

FIG. 40B illustrates a perspective view of an inner portion 4020 of an embodiment of the biosensor 100. The inner portion 4020 of the patch 102 is configured to face towards skin tissue of a user. The inner portion 4020 includes at least a first photodiode 4022 and may also include a second photodiode 4024. The photodiodes 4022, 4024 are positioned on opposite sides of a plurality of LEDs 4026. The LEDs 4026 are configured to emit light at a plurality of wavelengths. Additional or alternative LEDs may be included that have different wavelengths depending on the substance or patient vitals to be detected. The patch 102 may also include a temperature sensor 4028 configured to detect a skin temperature of the patent.

In one embodiment, the photodiodes 4022, 4024, temperature sensor 4028, processing circuit, memory, LEDs 4026 are implemented on a single circuit board 4030 though other implementations and configurations are possible in one or more embodiments described herein. A gasket 4032 is implemented to hold the circuit board 4030 in position.

Figure 41A:
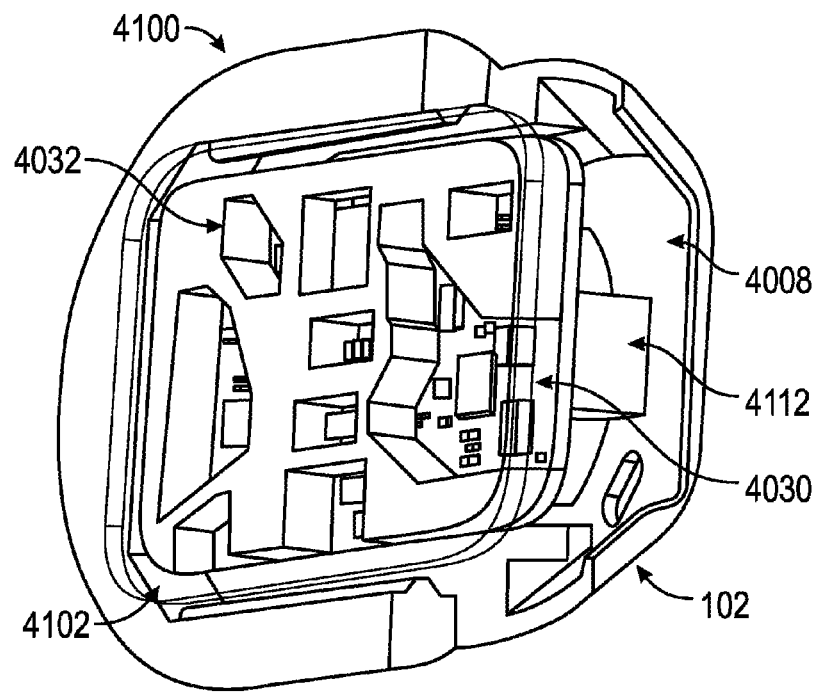
FIG. 41A illustrates a perspective view of inner portions of an embodiment of the patch
Figure 41B:
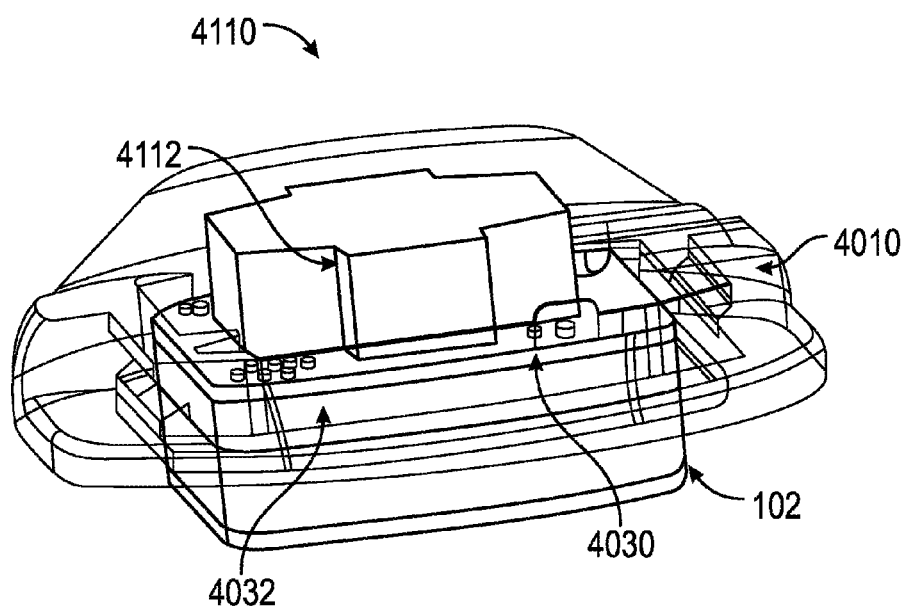
FIG. 41B illustrates another perspective view of inner portions of an embodiment of the patch.

FIGS. 41A and 41B illustrate perspective views of inner portions of an embodiment of the patch 102. FIG. 41A illustrates the first piece 4008 of the patch 102 including the circuit board 4030 and gasket 4032. A clear piece of plastic 4102 may be positioned over the gasket 4032 to provide a protective cover to the LEDs 4026 and photodiodes 4022, 4024. FIG. 41B illustrates the second piece 4010 of the patch 102 including the battery 4112. The battery 4112 is positioned on a first side of the circuit board 4030 while the gasket 4032 is located on a second side of the circuit board 4030. A person of skill in the art would appreciate that other implementations and configurations of the components of the patch 102 may be implemented in one or more embodiments herein.

Embodiment—Measurements of Pain Level

FIG. 42 illustrates a logical flow diagram of an embodiment of a method 4000 for determining a pain level using the biosensor 100. Nitric oxide (NO) is involved in many physiological processes and several lines of evidence have indicated that NO plays a complex and diverse role in the modulation of pain. For example, NSAID medication reduces NO levels and reduces pain levels in patients. The effectiveness of pain reducing medication may thus be monitored based on measured NO levels. In addition, a correlation between the NO levels at the site of tissue injury and pain intensity has been documented. Thus a pain level or intensity of an injury may be determined based on measured NO levels.

The biosensor 100 non-invasively obtains an NO measurement related to the level of NO in blood vessels at 4202. An indication of the NO measurement may be displayed at 4204. For example, the patch 102 may include a row of LEDs that are illuminated to indicate the measured level of NO. Alternatively, the patch 102 may include an LED configured to illuminate in one or more colors or hues to indicate the level of NO or include a display that indicates the NO level.

The NO measurement of the patient is compared to one or more predetermined thresholds at 4206. For example, the predetermined thresholds may be based on a range or an average or mean of NO measurements of a sample population before and after a dosage of a pain medication. The NO measurement of an individual patient may then be compared to the predetermined ranges. Depending on the comparison, a pain level or an increase or decrease in a pain level may be demonstrated. An indication of the pain level or an indication of an increase or decrease of a pain level may then be displayed at 4208.

Measurement of Heart Rate

Figure 43:
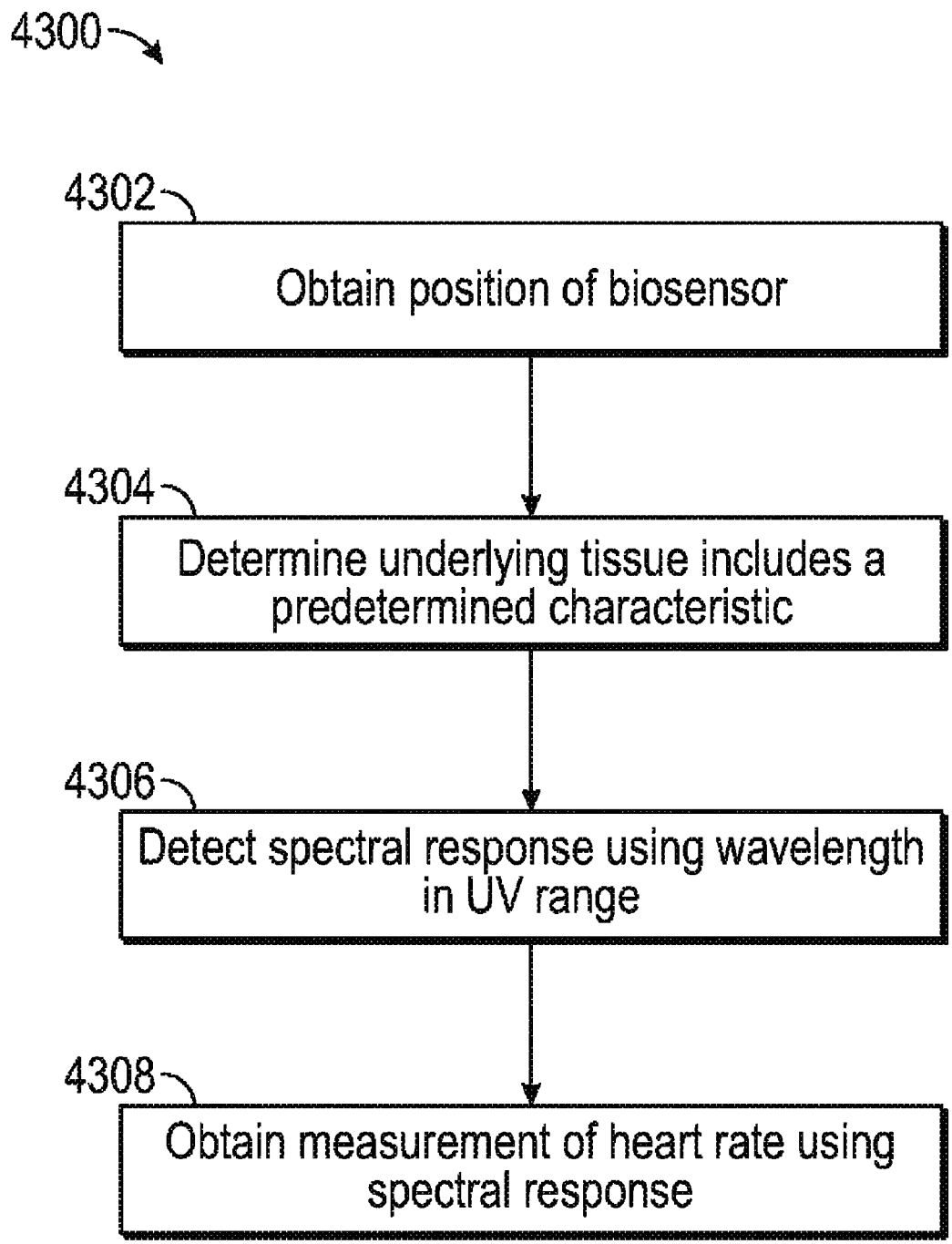
FIG. 43 illustrates a logical flow diagram of an exemplary embodiment of a method for determining a cardiac cycle.

FIG. 43 illustrates a logical flow diagram of an exemplary embodiment of a method 4300 for determining a cardiac cycle. In an embodiment, a spectral response of a wavelength in the UV range of 400 nm or in a range with a wavelength of 500 nm or less may be used to determine a heart rate or pulse rate. It has been determined in unexpected results that a measurement of heart rate or pulse rate (bpm) may be more easily detected using a wavelength in a range of 500 nm or less, especially over certain types of skin tissue with fewer blood vessels. For example, certain types of skin tissue have fatty tissue or deposits or may not have blood vessels that are prevalent or near the skin surface, e.g., abdominal area, upper arm, thigh, calf or other skin areas.

In an embodiment, the biosensor 100 determines its position on a skin surface at 4302. Alternatively or in addition thereto, the biosensor 100 determines that the underlying skin tissue at its position includes one or more predetermined characteristics indicative of fewer or deeper blood vessels, e.g. areas with fatty tissue or deposits or wherein major arterial blood vessels may not be prevalent or near the skin surface at 4304. The biosensor 100 then transmits a wavelength in the UV range (e.g., 400 nm or less) or a wavelength in a range of 500 nm or less directed at the skin tissue. The biosensor 100 detects the spectral response at 4306 and obtains a signal indicating arterial pulse pressure waves (e.g., indicative of cardiac cycles) from the spectral response. A measurement of the heart rate (bpm) and other information may be obtained from the spectral response at 4308. The heart rate measurement is more easily obtained from this spectral response at a wavelength in the UV range or at a wavelength in a range of 500 nm or less due to the deeper penetration of these wavelengths in the skin tissue. The signal indicating arterial pulse pressure waves is thus more easily detectable from this spectral response.

Detection of Hyperglycemia or Hypoglycemia

Figure 44:
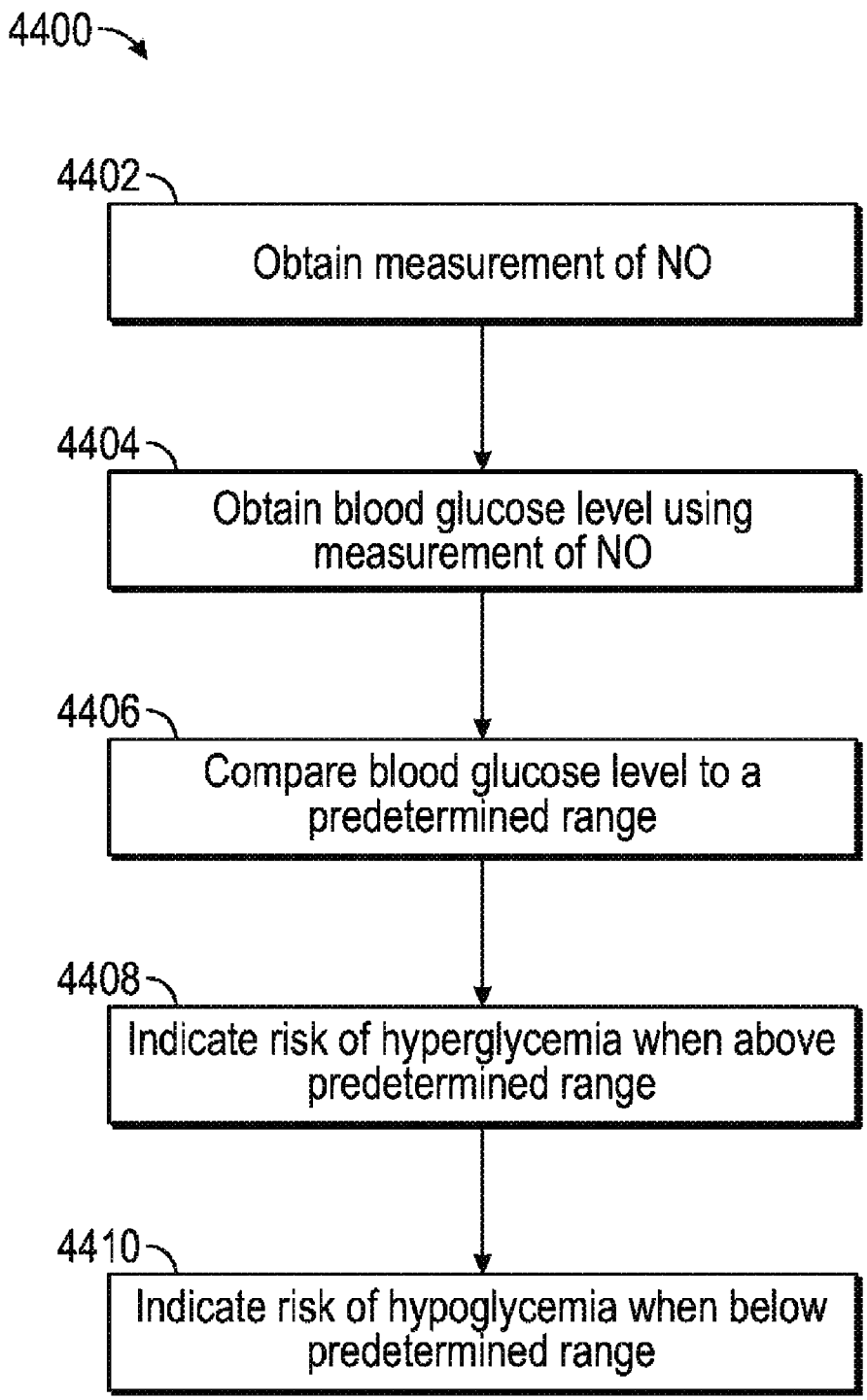
FIG. 44 illustrates a logical flow diagram of an exemplary embodiment of a method for detecting hyperglycemia or hypoglycemia.

FIG. 44 illustrates a logical flow diagram of an exemplary embodiment of a method 4400 for detecting hyperglycemia or hypoglycemia. In general, a normal range for blood glucose levels is about 70 to 110 milligrams per deciliter or mg/dl (3.9 to 6.1 millimoles per liter or mmol/l). The biosensor 100 may determine blood glucose levels and provide an indication of low blood glucose levels (hypoglycemia) or high blood glucose levels (hyperglycemia).

The biosensor 100 obtains a measurement of NO using one or more methods described herein at 4402. The biosensor 100 may then determine a blood glucose level using the measurement of NO and a calibration table or database at 4404. The bio sensor 100 compares the blood glucose level to a predetermined range of normal blood glucose levels, e.g. 70 to 110 mg/dl, at 4406. When the blood glucose level is above the predetermined range or threshold, the biosensor 100 indicates a risk of hyperglycemia at 4408. When the blood glucose level is below the predetermined range or threshold, the biosensor indicates a risk of hypoglycemia at 4410.

One or more embodiments have been described herein for a non-invasive and continuous method for monitoring one or more health conditions with a biosensor 100. Due to its compact form factor, the biosensor 100 may be positioned on various parts of a patient, including on a forehead, arm, wrist, abdominal area, chest, leg, hand, arm, etc. The biosensor 100 includes a PPG circuit 110 for detecting biosensor data, such as a patient's vitals and NO concentration levels. The PPG circuit 110 is configured to non-invasively and continuously detect nitric oxide (NO) levels in blood flow to determine a risk of sepsis or other health condition.

In one embodiment, the biosensor 100 detects a plurality of spectral responses from light reflected from skin tissue of a patient. The spectral responses are used to determine an R value from $L_{\lambda 1}/L_{\lambda 2}$, wherein $\lambda 1$ has a high absorption coefficient for NO and is in a UV range, e.g. from 380 nm to 410 nm and preferably in a range from 390-395 nm. The second wavelength $\lambda 2$ has a lower absorption coefficient for NO than the first wavelength $\lambda 1$ and may be in a range equal to or greater than 660 nm.

The R value may be non-invasively and quickly and easily obtained using the biosensor 100 in a physician's office or other clinical setting or at home. In one aspect, the R value may be compared to one or more predetermined thresholds to determine a risk for a health condition. When the R value exceeds one or more predetermined thresholds, the biosensor 100 may trigger a visible or audible alert. The alert may then be used to determine whether further testing for the health condition needs to be performed. For example, upon detection of a high R value of greater than 8, the biosensor 100 may issue an alert of a risk of sepsis, and a clinician may then determine to perform further testing and monitoring for sepsis.

In one or more aspects herein, a processing module or circuit includes at least one processing device, such as a microprocessor, micro-controller, digital signal processor, microcomputer, central processing unit, field programmable gate array, programmable logic device, state machine, logic circuitry, analog circuitry, digital circuitry, and/or any device that manipulates signals (analog and/or digital) based on hard coding of the circuitry and/or operational instructions. A memory is a non-transitory memory device and may be an internal memory or an external memory, and the memory may be a single memory device or a plurality of memory devices. The memory may be a read-only memory, random access memory, volatile memory, non-volatile memory, static memory, dynamic memory, flash memory, cache memory, and/or any non-transitory memory device that stores digital information.

As may be used herein, the term "operable to" or "configurable to" indicates that an element includes one or more of circuits, instructions, modules, data, input(s), output(s), etc., to perform one or more of the described or necessary corresponding functions and may further include inferred coupling to one or more other items to perform the described or necessary corresponding functions. As may also be used herein, the term(s) "coupled", "coupled to", "connected to" and/or "connecting" or "interconnecting" includes direct connection or link between nodes/devices and/or indirect connection between nodes/devices via an intervening item (e.g., an item includes, but is not limited to, a component, an element, a circuit, a module, a node, device, network element, etc.). As may further be used herein, inferred connections (i.e., where one element is connected to another element by inference) includes direct and indirect connection between two items in the same manner as "connected to".

As may be used herein, the terms "substantially" and "approximately" provides an industry-accepted tolerance for its corresponding term and/or relativity between items. Such an industry-accepted tolerance ranges from less than one percent to fifty percent and corresponds to, but is not limited to, frequencies, wavelengths, component values, integrated circuit process variations, temperature variations, rise and fall times, and/or thermal noise. Such relativity between items ranges from a difference of a few percent to magnitude differences.

Note that the aspects of the present disclosure may be described herein as a process that is depicted as a schematic, a flowchart, a flow diagram, a structure diagram, or a block diagram. Although a flowchart may describe the operations as a sequential process, many of the operations can be performed in parallel or concurrently. In addition, the order of the operations may be re-arranged. A process is terminated when its operations are completed. A process may correspond to a method, a function, a procedure, a subroutine, a subprogram, etc. When a process corresponds to a function, its termination corresponds to a return of the function to the calling function or the main function.

The various features of the disclosure described herein can be implemented in different systems and devices without departing from the disclosure. It should be noted that the foregoing aspects of the disclosure are merely examples and are not to be construed as limiting the disclosure. The description of the aspects of the present disclosure is intended to be illustrative, and not to limit the scope of the claims. As such, the present teachings can be readily applied to other types of apparatuses and many alternatives, modifications, and variations will be apparent to those skilled in the art.

In the foregoing specification, certain representative aspects of the invention have been described with reference to specific examples. Various modifications and changes may be made, however, without departing from the scope of the present invention as set forth in the claims. The specification and figures are illustrative, rather than restrictive, and modifications are intended to be included within the scope of the present invention. Accordingly, the scope of the invention should be determined by the claims and their legal equivalents rather than by merely the examples described. For example, the components and/or elements recited in any apparatus claims may be assembled or otherwise operationally configured in a variety of permutations and are accordingly not limited to the specific configuration recited in the claims.

Furthermore, certain benefits, other advantages and solutions to problems have been described above with regard to particular embodiments; however, any benefit, advantage, solution to a problem, or any element that may cause any particular benefit, advantage, or solution to occur or to become more pronounced are not to be construed as critical, required, or essential features or components of any or all the claims.

As used herein, the terms "comprise," "comprises," "comprising," "having," "including," "includes" or any variation thereof, are intended to reference a nonexclusive inclusion, such that a process, method, article, composition or apparatus that comprises a list of elements does not include only those elements recited, but may also include other elements not expressly listed or inherent to such process, method, article, composition, or apparatus. Other combinations and/or modifications of the above-described structures, arrangements, applications, proportions, elements, materials, or components used in the practice of the present invention, in addition to those not specifically recited, may be varied or otherwise particularly adapted to specific environments, manufacturing specifications, design parameters, or other operating requirements without departing from the general principles of the same.

Moreover, reference to an element in the singular is not intended to mean "one and only one" unless specifically so stated, but rather "one or more." Unless specifically stated otherwise, the term "some" refers to one or more. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is intended to be construed under the provisions of 35 U.S.C. § 112(f) as a "means-plus-function" type element, unless the element is expressly recited using the phrase "means for" or, in the case of a method claim, the element is recited using the phrase "step for."

The invention claimed is:

1. A biosensor for detecting a sepsis condition, comprising:
a photoplethysmography (PPG) circuit configured to:
obtain at least a first spectral response of light reflected from skin tissue of a patient, wherein the light includes a first wavelength in an ultraviolet (UV) range;
obtain at least a second spectral response of light reflected from the skin tissue of the patient; and
a processing circuit configured to:
obtain a value $L_{\lambda 1}$ using the first spectral response, wherein the value $L_{\lambda 1}$ isolates the first spectral response due to pulsating blood flow;
obtain a value $L_{\lambda 2}$ using the second spectral response, wherein the value $L_{\lambda 2}$ isolates the second spectral response due to pulsating blood flow;
obtain a value $R_{\lambda 1, \lambda 2}$ from a ratio of the value $L_{\lambda 1}$ and the value $L_{\lambda 2}$, wherein the value $R_{\lambda 1, \lambda 2}$ is a measurement of nitric oxide (NO); and
compare the value $R_{\lambda 1, \lambda 2}$ to one or more predetermined thresholds; and generate an indication of a risk of sepsis based on the comparison.

2. The biosensor of claim 1, wherein the biosensor is implemented on a disposable patch.

3. The biosensor of claim 2, wherein the disposable patch comprises at least one of:
a visible indicator of the risk of sepsis; or
an audible indicator for providing an audible indication of the risk of sepsis.

4. The biosensor of claim 1, wherein the PPG circuit is further configured to:
obtain the second spectral response of light reflected from the skin tissue of the patient, wherein the light includes a second wavelength of 660 nm or greater.

5. The biosensor of claim 1, further comprising:
a memory configured with the one or more predetermined thresholds, wherein at least one of the predetermined thresholds is an R value indicative of a risk of sepsis.

6. The biosensor of claim 5, wherein the one or more predetermined thresholds include different values depending on a pre-existing condition of the patient.

7. The biosensor of claim 5, wherein the one or more predetermined thresholds include different values depending on a position of the biosensor or underlying skin tissue characteristics.

8. The biosensor of claim 1, the processing circuit is further configured to:
obtain a concentration level of NO using the value $R_{\lambda 1, \lambda 2}$ and a calibration database, wherein the calibration database is used to correlate the value $R_{\lambda 1, \lambda 2}$ and the concentration level of NO.

9. The biosensor of claim 1, wherein the first wavelength has a high absorption coefficient for nitric oxide in blood flow and is in a UV range of approximately 380 nm to 410 nm.

10. The biosensor of claim 1, wherein the processing circuit is further configured to:
obtain a concentration level of a plurality of hemoglobin species; and
compensate for the concentration level of the plurality of hemoglobin species to determine the value $R_{\lambda 1, \lambda 2}$.

11. The biosensor of claim 10, wherein the concentration level of the one or more hemoglobin species is determined by:
analyzing spectral responses of a plurality of wavelengths to determine differential absorption signals for each hemoglobin species; and
using a Beer-Lambert matrix equation for determining the concentration levels of the one or more hemoglobin species.

12. The biosensor of claim 1, further comprising:
a transceiver configured for communicating data to a remote device, wherein the data includes the measurement of NO and the indication of the risk of sepsis.

13. The biosensor of claim 1, wherein the processing circuit is further configured to:
obtain a measurement of heart rate and respiration rate using the first spectral response.

14. The biosensor of claim 1, further comprising:
a temperature sensor configured to measure a skin temperature; and
wherein the processing circuit is further configured to:
compare the skin temperature to one or more predetermined thresholds; and
activate a health alert indicator when the skin temperature exceeds the one or more predetermined thresholds.

15. A biosensor configured to monitor one or more health conditions, comprising:
a sensor circuit configured to:
generate at least a first spectral response for light with a first wavelength in an ultraviolet (UV) range reflected from skin tissue of a patient; and
generate at least a second spectral response for light detected around a second wavelength reflected from the skin tissue of the patient; and
a processing circuit configured to:
determine a first mode of operation for monitoring a risk of sepsis;
obtain a measurement of nitric oxide (NO) in pulsating blood flow using the first spectral response and the second spectral response, wherein the measurement of NO is determined by:
obtaining a value $L_{\lambda 1}$ using the first spectral response, wherein the value $L_{\lambda 1}$ isolates the first spectral response due to pulsating blood flow;
obtaining a value $L_{\lambda 2}$ using the second spectral response, wherein the value $L_{\lambda 2}$ isolates the second spectral response due to pulsating blood flow;
obtaining a value $R_{\lambda 1, \lambda 2}$ from a ratio of the value $L_{\lambda 1}$ and the value $L_{\lambda 2}$ wherein the value $R_{\lambda 1, \lambda 2}$ is the measurement of NO;
compare the measurement of NO to one or more predetermined thresholds based on the first mode of operation; and
generate an indication of the risk of sepsis based on the comparison.

16. The biosensor of claim 15, wherein the processing circuit is further configured to:
determine a second mode of operation for determining a diabetic risk indicator;
compare the measurement of NO to one or more predetermined thresholds based on the second mode of operation; and
obtain a base insulin resistance factor that indicates a diabetic risk indicator.

17. The biosensor of claim 15, wherein the processing circuit is further configured to:
determine a third mode of operation for monitoring a blood glucose concentration level detected from an insulin response; and
obtain the blood glucose concentration level detected from the insulin response using the measurement of NO and a calibration table.

18. The biosensor of claim 15, further comprising:
a user interface circuit configured to select one or more modes of operation of the biosensor.

19. The biosensor of claim 15, wherein the processing circuit is further configured to obtain a measurement of heart rate using a spectral response from a wavelength in the UV range; and
wherein the biosensor further comprises a heart rate indicator.

20. The biosensor of claim 19, wherein the wavelength in the UV range is 400 nm or less.

21. The biosensor of claim 19, wherein the processing circuit is further configured to:
compare the measurement of heart rate to one or more predetermined thresholds for heart rate; and
activate the heart alert indicator when the measurement of heart rate exceeds the one or more predetermined thresholds for heart rate.

22. The biosensor of claim 15, wherein the processing circuit is further configured to:

obtain a measurement of respiration rate using at least one of: the first spectral response or the second spectral response; and compare the respiration rate obtained to one or more predetermined thresholds; and activate a health alert indicator then the respiration rate exceeds the one or more predetermined thresholds.

23. A method for detecting a sepsis condition, comprising:

obtaining a first spectral response of light reflected from skin tissue of a patient, wherein the light includes a first wavelength in an ultraviolet (UV) range;

obtaining a second spectral response of light reflected from skin tissue of a patient, wherein the light includes a second wavelength of 530 nm or greater;

obtaining a value $L_{\lambda,1}$ using the first spectral response, wherein the value $L_{\lambda,1}$ isolates the first spectral response due to pulsating blood flow;

obtaining a value $L_{\lambda,2}$ using the second spectral response, wherein the value $L_{\lambda,2}$ isolates the second spectral response due to pulsating blood flow;

obtaining a value $R_{\lambda 1, \lambda 2}$ from a ratio of the value $L_{\lambda,1}$ and the value $L_{\lambda,2}$, wherein the value $R_{\lambda 1, \lambda 2}$ is a measurement of nitric oxide (NO);

comparing the value $R_{\lambda 1, \lambda 2}$ to one or more predetermined thresholds; and generating an indication of a risk of sepsis based on the comparison.

24. The method of claim 23, wherein the one or more predetermined thresholds includes an R value indicative of a risk of sepsis.

* * * * *